US012758716B2

(12) United States Patent
Draper et al.

(10) Patent No.: US 12,758,716 B2
(45) Date of Patent: Oct. 13, 2026

(54) ELECTRONIC SYSTEM FOR A DRUG DELIVERY DEVICE AND DRUG DELIVERY DEVICE

(71) Applicant: Sanofi, Paris (FR)

(72) Inventors: Paul Richard Draper, Warwick (GB); Zoë Georgina Eardley, Warwick (GB); Oliver Charles Gazeley, Warwick (GB); William Geoffrey Arthur Marsh, Warwick (GB); Anthony Paul Morris, Warwick (GB); David Aubrey Plumptre, Warwick (GB); Ronald Antony Smith, Warwick (GB); Robert Veasey, Warwick (GB)

(73) Assignee: SANOFI, Paris (FR)

( * ) Notice: Subject to any disclaimer, the term of this patent is extended or adjusted under 35 U.S.C. 154(b) by 1011 days.

(21) Appl. No.: 17/914,507

(22) PCT Filed: Mar. 25, 2021

(86) PCT No.: PCT/EP2021/057665

§ 371 (c)(1),
(2) Date: Sep. 26, 2022

(87) PCT Pub. No.: WO2021/191322

PCT Pub. Date: Sep. 30, 2021

(65) Prior Publication Data

US 2023/0128892 A1 Apr. 27, 2023

(30) Foreign Application Priority Data

Mar. 27, 2020 (EP) .................................... 20315066

(51) Int. Cl.
*A61M 5/315* (2006.01)
*A61M 5/24* (2006.01)

(52) U.S. Cl.
CPC .......... *A61M 5/31568* (2013.01); *A61M 5/24* (2013.01); *A61M 5/3155* (2013.01); *A61M 2205/581* (2013.01)

(58) Field of Classification Search
CPC ............ A61M 5/31568; A61M 5/3255; A61M 5/31556; A61M 5/3156; A61M 5/31563; A61M 5/31573
See application file for complete search history.

(56) References Cited

U.S. PATENT DOCUMENTS

2021/0146061 A1* 5/2021 Byerly .............. A61M 5/31568
2023/0001098 A1* 1/2023 Friedlander ....... A61M 5/31553

FOREIGN PATENT DOCUMENTS

CN 106470716 A 3/2017
CN 109414548 A 3/2019
(Continued)

OTHER PUBLICATIONS

Notification of Reasons for Rejection, JP Patent Application No. 2022-558016, dated Jan. 10, 2025, pp. 1-7 (with pp. 1-3 being a translation).
(Continued)

*Primary Examiner* — Courtney Fredrickson
*Assistant Examiner* — Kayla M. Turkowski
(74) *Attorney, Agent, or Firm* — Bond, Schoeneck & King, PLLC

(57) ABSTRACT

An electronic system for a drug delivery device is provided. The electronic system comprises a dose setting and drive mechanism comprising a first member and a second member, wherein in the dose delivery operation and/or in the dose setting operation, the first member moves, e.g. rotates, relative to the second member; an electronic control unit; an electrical use detection unit operatively connected to the electronic control unit, and configured to generate a use
(Continued)

signal in response to the relative movement, e.g. a relative rotational movement, between the first member and the second member, preferably during the dose delivery operation. The electronic system is configured such that it is switched from a first state into a second state by the electronic control unit in response to the use signal, wherein the electronic system has an increased electrical power consumption in the second state as compared to the first state.

20 Claims, 23 Drawing Sheets

(56) References Cited

FOREIGN PATENT DOCUMENTS

| | | | | |
|---|---|---|---|---|
| CN | 110035785 A | 7/2019 | | |
| JP | 2016514249 A | 5/2016 | | |
| JP | 2016540555 A | 12/2016 | | |
| JP | 2019500142 A | 1/2019 | | |
| WO | WO 2015/028439 | 3/2015 | | |
| WO | WO 2015/071354 | 5/2015 | | |
| WO | WO 2019/040313 | 2/2019 | | |
| WO | WO-2019077094 A1 * | 4/2019 | ........ | A61M 5/31568 |
| WO | 2019101962 A1 | 5/2019 | | |
| WO | WO 2019/219825 | 11/2019 | | |

OTHER PUBLICATIONS

International Preliminary Report on Patentability in International Appln. No. PCT/EP2021/057665, mailed on Oct. 6, 2022, 7 pages.
International Search Report and Written Opinion in International Appln. No. PCT/EP2021/057665, mailed on Jun. 10, 2021, 9 pages.
Search Report for Chinese Patent Application No. 2021800245488 dated Oct. 24, 2025 in English (2 pages).

* cited by examiner

ELECTRONIC SYSTEM FOR A DRUG DELIVERY DEVICE AND DRUG DELIVERY DEVICE

CROSS-REFERENCE TO RELATED APPLICATIONS

The present application is the national stage entry of International Patent Application No. PCT/EP2021/057665, filed on Mar. 25, 2021, and claims priority to Application No. EP 20315066.9, filed on Mar. 27, 2020, the disclosures of which are incorporated herein by reference.

BACKGROUND

The present disclosure relates to an electronic system for a drug delivery device. The present disclosure further relates to a drug delivery device, which preferably comprises the electronic system.

Drug delivery devices using electronics are becoming increasingly popular in the pharmaceutical industry as well as for users or patients. However, especially if the device is designed to be self-contained, that is to say without a connector for a connection to an electrical power source which is necessary to provide electrical power for the operation of the device, the management of the resources of a power supply integrated into the device is particularly important.

SUMMARY

The present disclosure relates to improvements for drug delivery devices comprising an electronic system or electronic systems for drug delivery devices.

One aspect of the disclosure relates to an electronic system for a drug delivery device. Another aspect of the disclosure relates to a drug delivery device comprising the electronic system. Accordingly, the features described herein with relation to the drug delivery device should be considered as being disclosed for the electronic system and vice versa.

In one embodiment, the electronic system or drug delivery device comprises a dose setting and/or drive mechanism. The dose setting mechanism may be configured to perform a dose setting operation for setting a dose to be delivered by the drug delivery device. The dose which can be set in the drug delivery device may be a variable dose, i.e. the size of the dose which can be set is not fixed by the design of the mechanism but rather can be chosen by the user. Preferably, the user can choose the set dose between a minimum settable dose and a maximum settable dose. The drive mechanism may be configured to perform a dose delivery operation for delivering the dose, e.g. the dose which has been previously set.

In one embodiment, the electronic system of the drug delivery device comprises a housing. The housing may house components of the dose setting and/or drive mechanism and/or one or more further components of the electronic system or the drug delivery device. The housing may be an outer housing. That is to say, the housing may present an outer surface of the electronic system or the drug delivery device. Members which are described to move herein may move relative to the housing during operation of the electronic system and/or the dose setting and/or drive mechanism.

In one embodiment, the dose setting and/or drive mechanism comprises a user interface member, e.g. dose and/or injection button. The user interface member may be arranged to be operated by the user to operate the mechanism.

In one embodiment, the dose setting and/or drive mechanism comprises a first member and a second member. The first member and/or the second member may be configured to move during the dose setting operation and/or the dose delivery operation relative to a housing of the electronic system or the drug delivery device. The first member may be a dose member or dial member of the dose setting and/or drive mechanism which is moved to set a dose, e.g. a dial sleeve or a number sleeve. The second member may be a drive member, e.g. a member engaged with a piston rod of the dose setting and/or drive mechanism, or a user interface member, such as a dose and/or injection button. The first member and/or the second member may be movably coupled to or retained in the housing. In the dose setting operation, the first member and/or the second member may be displaced axially relative to the housing, for example away from a proximal end of the housing. The distance by which the first member and/or the second member is displaced during the dose setting operation relative to the housing axially may be determined by the size of the set dose. In other words, the drug delivery device may be of the dial extension type, i.e. the device increases its length during the dose setting operation in an amount proportional to the size of the set dose.

In one embodiment, in the dose setting operation and/or in the dose delivery operation, the first member moves, e.g. rotates and/or moves axially, relative to the second member. For example, the first member may rotate relative to the second member during the dose delivery operation. The first member and the second member may both move axially during the dose delivery operation. The first member may rotate relative to the second member and relative to the housing during the dose setting operation and/or the dose delivery operation. The second member may be rotationally locked or guided with respect to the housing during the dose delivery operation, e.g. by a delivery clutch. The first member and the second member may be rotationally locked relative to one another during the dose setting operation. Accordingly, the first member and the second member may rotate relative to the housing in the dose setting operation. During the dose setting operation the first member and the second member may be coupled to one another, e.g. via a coupling interface, e.g. a setting clutch. The coupling interface may rotational lock the first member and the second member to one another during the dose setting operation. When the coupling interface is engaged, the first member and the second member may be rotationally locked with one another, such as by direct engagement of coupling interface features. The first member and the second member may comprise mating coupling interface features. The coupling interface may be released during the dose delivery operation. Particularly the use signal which is explained in more detail below may be generated only when the coupling interface, e.g. the delivery clutch and/or the setting clutch, has changed its state, e.g. from engaged to released or vice versa, and/or after the first member has already rotated relative to the second member.

In one embodiment, the first member and the second member rotate relative to one another during only one of the dose setting operation and the dose delivery operation. One of the first member and the second member may rotate relative to the housing during both operations. One of the first member and the second member may rotate relative to the housing during only one of the operations, e.g. during dose setting or during dose delivery.

In one embodiment, the device or the electronic system comprises an electronic control unit, e.g. comprising a microprocessor or microcontroller. The electronic control unit may be configured to control operation of the drug delivery device or the electronic system. The electronic control unit may be arranged on a conductor carrier and electrically conductively connected with conductors on the conductor carrier. The conductor carrier may be a circuit board such as a printed circuit board. The conductor carrier may be retained in the interior of the user interface member of the system or the device.

In one embodiment, the device or the electronic system comprises an electrical power supply. The power supply may be arranged in the interior of the electronic system such as in the interior of the user interface member.

In one embodiment, the electronic system has a first state and a second state. The first state and the second state may be different states of operation of the electronic system. In the first state, the system may be in an idle state, where the system does not operate with the desired functionality assigned to the electronic system, e.g. dose recording functionality, during a dose setting and/or dose delivery operation. In the second state, the system may be ready to operate with the desired functionality, especially when in the second state a dose setting operation and/or a dose delivery operation is being performed. The electronic system may have an increased electrical power consumption in the second state as compared to the first state. For example, in the second state, one or more electrical or electronic units of the electronic system may be switched to a state of higher power consumption, e.g. an on state, as compared to the first state, where the respective unit may be in a sleep state with low power consumption or an off state with no power consumption at all, e.g. because the connection to an electrical power supply is interrupted.

In one embodiment, the electronic system comprises an electrical use detection unit. The use detection unit may be operatively connected to the electronic control unit, e.g. electrically conductively, such as via a conductor on the conductor carrier. The electrical use detection unit may be configured to generate or trigger a use signal, e.g. an electrical signal. The use signal may be indicative that the user has commenced the dose setting operation or the dose delivery operation. Commencement of the dose setting operation or the dose delivery operation may require relative movement between the first member and the second member, e.g. relative rotational movement. Accordingly, the use signal may be generated only after the dose setting operation or the dose delivery operation has been commenced or initiated. In this way, it can be ensured that, when the use signal is generated, an operation it should be indicative for such as the dose setting operation or the dose delivery operation has already been commenced.

In one embodiment, the electronic system is configured such that the electronic system is switched from the first state into the second state by the electronic control unit in response to the use signal. Accordingly, generation of the use signal may be responsible and causal for switching the electronic system to the second state of increased power consumption. The electronic control unit may, in response to reception of the use signal issue a command, e.g. a signal, to another unit of the electronic system such that this unit is switched on or rendered operational. This unit may be a motion sensing unit which is configured to measure by how much the first member moves relative to the second member during the dose setting operation and/or the dose delivery operation. The movement may be indicative for the currently set or delivered dose.

In one embodiment, the use detection unit is configured to generate the use signal in response to the relative movement, e.g. relative rotational movement, between the first member and the second member, expediently during the dose delivery operation. Thus, the relative movement may be required between the first of the second member for generating the use signal. This implies that the dose setting or dose delivery operation is actually being performed and, consequently, it is very likely that system is operated intentionally. This is even more true when the use signal is generated only during the dose delivery operation, e.g. when the delivery operation has commenced.

In one embodiment, the first member is a member different from a user interface member. Specifically, the first member may not have any surface which is intended to be touched by the user for operating the drug delivery device or the system. The first member may be an interior member of the drug delivery device or the system. The first member may be arranged within the housing of the drug delivery device.

In one embodiment, the dose setting and/or drive mechanism comprises a dose member, e.g. a number sleeve or a dial sleeve. The dose member may be rotatable in the dose setting operation, e.g. in whole-number multiples of a unit setting increment relative to the housing. During the dose setting operation, the dose member may be operatively coupled, e.g. rotationally locked, to the user interface member and/or the second member. The unit setting increment may be an angle which is constant. Accordingly, the unit setting increment may define the smallest dose settable with the dose setting and/or drive mechanism. One unit setting increment may correspond to a rotation of greater than or equal to 10° and/or a rotation of less than or equal to 20°, e.g. 15°. The electronic system may comprise an incremented setting interface which defines the unit setting increment. The setting interface may be a ratchet interface. The ratchet interface may operate between the dose member and the housing, for example.

In one embodiment, the rotation axis around which one, more, or all of the rotations discussed herein take place may be a longitudinal axis of the housing and/or the rotation axis around which the first member and/or the second member rotate, e.g. relative to the housing, during dose setting and/or dose delivery.

In one embodiment, one of the first member and the second member is the dose member. Alternatively, the first member and the second member are different from the dose member.

In one embodiment, at least a portion of the second member is received within the first member.

In one embodiment, the first member and/or the second member or a portion of the respective member has a sleeve-like configuration.

In one embodiment, the electronic system is configured such that the use signal is generated, preferably only, after rotation of the first member relative to the housing and/or the second member has been commenced. The use signal may be generated before the first member is rotated relative to the second member and/or the housing by two unit setting increments, preferably before the first member has rotated relative to the second member and/or the housing by more than one unit setting increment.

In one embodiment, the electronic system is configured such that the switching of the electronic system from the first state into the second state has been completed before the relative rotation between the first member and the second member reaches two unit setting increments, preferably before one unit setting increment. Consequently, the wake-up process for switching the system to the second state of higher power consumption may be completed quickly. This implies that the motion sensing unit, for example can be operated very soon after the initiation of the dose setting operation or the dose delivery operation.

In one embodiment, the electronic system is configured such that switching the system from the first state into the second state is completed within a time span of less than or equal to one of the following values: 5 ms, 4 ms, 3.5 ms, 3.2 ms, 3 ms, 2.8 ms, 2.7 ms, 2.5 ms (ms: milliseconds). Alternatively or additionally, the electronic system is configured such that switching the system from the first state into the second state is completed within a time span of greater than or equal to one of the following values: 1 ms, 1.5 ms, 1.7 ms, 2.0 ms, 2.2 ms, 2.5 ms. Particularly, the time span required for switching the system from the first state to the second state may be between 1 ms and 5 ms. The time span required for switching may be determined from the generation of the use signal or from the commencement of a movement of the user interface member for performing a dose setting operation or dose delivery operation up to the time when the motion sensing unit and/or the communication unit has become operational.

In one embodiment, the relative rotation of the first member and the second member during the dose delivery operation may be indicative for the size of the dose being dispensed in the dose delivery operation or being set in the dose setting operation. Accordingly, as the use signal is generated only after the rotation has been commenced, an offset as to be taken into account, when the dose should be calculated from the relative rotation which has been measured. The offset may be one unit setting increment which has to be added to the measured dose as this dose is needed to activate the electronic system and, particularly, its set and/or dispensed dose measuring and/or recording capability.

In one embodiment, the electronic system comprises a use signal generation interface, for example comprising a ratchet interface such as a radial ratchet interface or an axial ratchet interface. The use signal generation interface may be configured to generate one or more use signals in response to relative rotation between the first member and the second member. The use signal generation interface may be configured to generate one, e.g. only one, or more use signals during the dose delivery operation. In case more than one use signal is generated, preferably the first use signal which is generated is the one which is used to trigger switching of electronic system from the first state into the second state. The use signal generation interface may be an incremented interface. The use signal generation increment may be an angle. The use signal generation increment may be adjusted to the unit setting increment. Preferably the use signal generation increment is equal to or smaller than the unit setting increment. That is to say, the pitch of the use signal generation increments and the unit setting increments may be equal or the use signal generation increments may be finer pitched. With a finer pitch, a rotation by one unit setting increment may cover more than one use signal generation increments.

In one embodiment, the electronic system comprises a use signal generation interface member. A ratchet, e.g. with ratchet teeth and/or ratchet pockets, for the use signal generation interface may be provided on the use signal generation interface member. The ratchet teeth of the ratchet and/or the ratchet pockets may be axially or radially oriented. That is to say, a free end of the teeth may point into the radial direction. The use signal generation interface member may be a separate member from the first and second members. Alternatively, the use signal generation interface member may be one of the first and second members, e.g. the first member. The use signal generation interface member may be rotationally locked to one of the first member and the second member. The use signal generation interface member may be axially movable relative to the member to which it is connected, e.g. rotationally locked, e.g. in a limited manner. The use signal generation interface member may be axially locked to the other one of the first member and the second member, e.g. to the second member.

In one embodiment, the electronic system or the drug delivery device comprises a movable switching feature. The switching feature may be movable along the rotation axis or the main longitudinal axis of the housing and/or transversely or radially to the rotation axis or the main longitudinal axis of the housing. The switching feature may be rotationally locked to one of the second member in the first member, preferably to the second member. The switching feature may be arranged to move either only radially or only axially or radially and axially. The switching feature may be rigid or, preferably elastically, deformable. The switching feature may be operatively coupled to one of the first member and the second member, e.g. via the use signal generation interface member. For example, the switching feature may engage the ratchet, e.g. the one which defines the use signal generation increment. The switching feature may be operatively coupled to the first member and/or the second member such that rotation of the first member relative to the second member causes movement of the switching feature relative to the first member, relative to the second member and/or relative to the housing. For example, rotation of the first member relative to the second member, relative to the switching feature and/or relative to the housing may be converted into movement of the switching feature, e.g. by an operative coupling between the switching feature and a ratchet. Alternatively, rotation of the first member relative to the switching feature may remove a mechanical block which blocks movement of the switching feature in a direction into which the switching feature is biased. The movement of the switching feature may be used to trigger generation of the use signal. In other words, movement of the switching feature in response to the movement of the first member relative to the second member may be required to generate the use signal. For example, to generate or trigger the use signal movement of the switching feature may be used to and/or cause a change in the state of an electrical connection, e.g. from open to closed or vice versa, and/or to trigger an electrical switch. The switching feature may be electrically insulating, e.g. of plastic, or it may be electrically conductive, e.g. of metal. If the switching feature is electrically conductive, it may form part of an electrical switch, e.g. of a contact feature of the switch, which is brought into electrical contact with another contact feature of the switch in order to generate the use signal.

In one embodiment, the switching feature engages a ratchet, e.g. a ratchet which may be associated with the first or second member. The switching feature may be biased into engagement with the ratchet, e.g. when it has been displaced out of a ratchet pocket defined between two adjacent ratchet teeth of the ratchet. A biasing force acting on the switching feature may act counter to the direction of movement of the switching feature which causes generation of the use signal.

For generating the use signal, the switching feature may be moved radially inwardly, for example. In an initial state, before the dose setting operation or the dose delivery operation is commenced, the switching feature may be engaged with the ratchet pocket defined by adjacent ratchet teeth, such as teeth of the ratchet defining the use signal generation interface.

In one embodiment, before the first member is moved relative to the second member and/or before the dose setting operation or the dose delivery operation is commenced, the switching feature is, preferably resiliently, biased into engagement with a block feature with a biasing force. The block feature may block movement of the switching feature relative to the housing in the direction of the biasing force, the first member and/or the second member. The biasing force may be provided by an electrical contact feature, e.g. of a switch, which is resiliently displaced before the dose setting operation and/or the dose delivery operation is commenced. The block feature may be provided by a ratchet tooth between two adjacent ratchet pockets. The biasing force may act in the direction of movement which causes generation of the use signal. For example, the switching feature in cooperation with the block feature may maintain a switch in an open condition. When the block feature is removed from the switching feature, the bias may release and the switch may be closed. In order to generate the use signal when the dose setting operation or the dose delivery operation is commenced, the switching feature may move in the radially outward direction, for example.

In one embodiment, the electronic system or the drug delivery device is configured such that movement of the switching feature is used to trigger an electrical switch, e.g. by contacting and/or moving a trigger feature of the switch. When the switch is triggered, the use signal may be generated. In response to the use signal, the electronic control unit may switch the electronic system from the first state into the second state.

In one embodiment, the switching feature is linearly guided. For example, the switching feature may be received in a guide slot. The switching feature may move only linearly, e.g. radially or axially, as it is linearly guided. This provides a comparatively simple movement type when triggering the use signal. The guide slot may be provided in the second member, for example.

In one embodiment, the switching feature is oriented axially, particularly along the rotation axis, or radially or transversely, particularly with respect to the rotation axis.

In one embodiment, the switching feature is pivotally mounted, particularly within the electronic system or the drug delivery device. The movement of the switching feature which causes generation of the use signal may be a pivoting movement. The switching feature may be pivotally mounted to the second member.

In one embodiment, the switching feature is moved transversely to and/or along the rotation axis around which the first member rotates relative to the second member and/or to the housing in the dose setting operation and/or the dose delivery operation.

In one embodiment, the switching feature is pin-like and/or has a main extension direction.

In one embodiment, the switching feature has a portion with a U-like cross-section, especially when the cross-section is taken parallel to the rotation axis.

In one embodiment, one of the first member and the second member is provided with a ratchet. The switching feature may be arranged to cooperate mechanically with the ratchet. The ratchet may be provided on the first member. The ratchet may be provided on the use signal generation interface member. The ratchet may comprise circumferentially or angularly disposed ratchet teeth. The ratchet teeth may be evenly distributed in the circumferential or angular direction. Two adjacent teeth may be separated by a ratchet pocket. The ratchet teeth may be axially, e.g. proximally, or radially, e.g. inwardly, oriented.

In one embodiment, the switching feature is biased into engagement with a ratchet pocket when it is attempted to be disengaged from the ratchet pocket. The bias may be provided by a resiliently displaceable feature and/or by an electrical contact feature of a switch.

In one embodiment, the electronic system or the drug delivery device comprises a plurality of switching features, e.g. a first switching feature and a second switching feature. The switching features may be arranged to cooperate with the ratchet. The switching features may be radially aligned, e.g. angularly offset by 180°, or may be oriented in different radial directions, e.g. offset by an angle different from 180°. The switching features may be arranged to cooperate with the ratchet at distinct locations along the ratchet. That is to say, locations where the two switching features engage the ratchet may be angularly separated from each other, especially by a plurality of pairs of ratchet teeth and ratchet pockets between the two locations. When the first member is rotated relative to the second member, at least one of the first and second switching features may be displaced relative to the first member and/or the second member. Preferably, both switching features are displaced. The two switching features may be displaced in the same direction or in different directions during the rotation. For example, both switching feature may be displaced inwardly, e.g. radially. The switching features may be displaced towards each other, e.g. such that the distance between the two switching features is reduced, e.g. the radial distance. Alternatively to being displaced in the same direction, one switching feature may be displaced outwardly and the other one may be displaced inwardly.

Having a plurality of switching features which cooperate with the same ratchet at different locations has the advantage that the relative movement of the switching features with respect to each other can be tuned by choosing the type of engagement with the ratchet. The two switching features may be in phase relative to the ratchet. That is to say, in a given stable rotational or angular position of the first member relative to the second member both switching features either engage a ratchet pocket or they both engage a ratchet tooth. This has the advantage that the two teeth may contribute to the radial displacement and the height of the teeth may be reduced to achieve a particular desired relative radial displacement of the switching features. Alternatively, the two switching features may be out of phase relative to the ratchet. That is to say in a given stable rotational or angular position of the first member relative to the second member one of the switching features engages a ratchet tooth and the other one engages a ratchet pocket.

In one embodiment, one deformable switching feature is engaged with the ratchet at distinct locations. The deformable switching feature may engage a radial ratchet. Rotation of the first member relative to the second member may cause a portion of the deformable switching feature to be axially displaced, e.g. on account of the switching feature cooperating with ratchet teeth of the ratchet. The axial displacement of the portion may be directed proximally. The axial displacement of the portion may be relative to the ratchet. The axial displacement may be used to trigger generation of the use signal. Particularly, the portion may protrude from the ratchet when axially displaced. The switching feature may be elastically deformable such that, when elastically deformed, it tends to resume its original shape on account of an elastic restoring force. The switching feature may bridge a free space within the member with the ratchet engaged by the switching feature. The switching feature may be continuous. Before the dose setting operation or dose delivery operation is commenced, the deformable switching feature, particularly opposite ends thereof, may be engaged with ratchet pockets of the ratchet. When the first member is rotated relative to the second member the engagement with ratchet teeth tends to deform, e.g. to compress, the switching feature. This may result in an axial displacement of a portion of the switching feature, e.g. a central portion. The switching feature may be configured as a wishbone or toggle mechanism component. The portion of the switching feature may be displaced axially in a direction away from the ratchet.

In one embodiment, the switching feature is rotationally locked to that member of the first and second member which is not provided with the ratchet.

In one embodiment, the electronic system or the drug delivery device comprises a motion sensing unit. The motion sensing unit may be an electronic unit. The motion sensing unit may be an optoelectronic unit. The motion sensing unit may be configured to measure and/or quantify movement of the first member relative to the second member. An encoder component may move relative to the motion sensing unit, e.g. an encoder ring. The encoder component may be or may be connected to the first member or the second member, preferably the first member. The encoder component may be the use signal generation interface member. The encoder component may comprise circumferentially spaced detection regions which trigger a signal generation in the motion sensing unit when they are moved into a detection position relative to the unit. The motion sensing unit may comprise at least one sensor, preferably a plurality of sensors. The respective sensor may be contactless. The respective sensor may be a radiation detector, for example. The motion sensing unit may comprise an electromagnetic radiation emitter, e.g. an LED, and a radiation detector. The radiation emitter may emit radiation towards the encoder component and the radiation detector may be arranged and configured to detect radiation reflected from the encoder component. In the first state the motion sensing unit may be non-operational or switched off. In the second state of the electronic system motion sensing unit may be operational or switched on. Motion sensing units for measuring relative movement of members such as for determining the currently set dose or the already dispensed dose during a dispensing operation may have a particularly high power consumption. The currently set dose or currently dispensed dose may depend on the amount of relative movement, e.g. rotation, between the first member and the second member from the onset of the respective operation. In the present disclosure, the motion sensing unit may be activated only after the respective operation during which the motion sensing unit should operate, e.g. the dose delivery operation and/or the dose setting operation, has already been commenced. The electronic system preferably considers the offset between the initiation or commencement of the dose setting operation or dose delivery operation and the operability of the motion sensing unit, e.g. by adding a value to the determined dose, e.g. constant value, such as one unit setting increment or two unit setting increments. The electronic control unit may be configured to issue a command to render the motion sensing unit operational in response to the use signal.

In one embodiment, the switching feature is configured to move a first electrical contact feature of an electrical switch into electrical and/or mechanical contact with a second electrical contact feature of the electrical switch when the first member is rotated relative to the second member. When the first electrical contact feature contacts the second electrical contact feature, the use signal may be generated. During rotation of the first member relative to the second member, the switching feature may be arranged to displace the second electrical contact feature. The switching feature may displace both the first contact feature and the second contact feature during the rotation, particularly in the same direction. In this way, it can be achieved that the use signal is generated in all tolerance conditions as after the contact has been established both contact features are moved together.

In one embodiment, the electronic system or the drug delivery device comprises a coupling interface, e.g. a clutch, which selectively locks the first member and the second member rotationally. The coupling interface, when established, may rotationally lock the two members and, when released may permit relative rotational movement. In the dose setting operation the coupling interface may be established. In the dose delivery operation, the coupling interface may be released.

In one embodiment, in order to switch from a dose setting configuration of the dose setting and drive mechanism in which the dose setting operation may be performed to a dose delivery configuration of the dose setting and drive mechanism in which the dose delivery operation may be performed, the first member and the second member may be axially displaceable relative to one another. The axial displacement may be a displacement of the second member in the distal direction relative to the first member. During the relative axial displacement, the state of a coupling interface may be switched, e.g. from established to released or vice versa. The relative axial displacement to change the state of the coupling interface may be mandatory before the dose delivery operation can be commenced. The relative axial displacement may be performed by movement of a user interface member of the device or system which may be connected to one of the first and second members or integral with one of these members, e.g. a dose or injection button. When the user presses a surface on the button, e.g. in the distal direction, the axial displacement may be effected. In other words, in the dose setting operation and in the dose delivery operation the first member and the second member may have different axial positions relative to one another.

In one embodiment, the ratchet, e.g. the one in the use signal generation interface member, is designed to permit relative rotation between the first member and the second member in two opposite directions or in only one direction. In other words, the ratchet may be unidirectional or bidirectional. In case a unidirectional ratchet is provided, the ratchet may provide resistance against or prevent a rotation of the first member relative to the second member in a direction which would increase the set dose when in a dose delivery configuration, e.g. when the second member has been axially displaced relative to the first member.

In one embodiment, generation of the use signal is independent of a change in the axial position of the user interface member or the second member relative to the first member. That is to say, merely pressing the user interface member dose not result in a use signal generation. Rather a rotational movement of the first member is required relative to the second member to generate a use signal.

In the dose setting configuration and/or in the dose delivery configuration, the relative relations or positions between the switching feature and the ratchet, e.g. the one in the use signal generation interface member, may be different and/or vary.

For example, the switching feature may engage the ratchet only in the initial stage of the dose setting operation or the dose delivery operation, particularly before the relative axial movement between the first member and the second member is completed. In this way, after the use signal has been generated, the switching feature may be disengaged from the ratchet and, for example, engage a plane surface with accordingly smaller frictional losses which may result in a smaller torque or force required to operate the device. Accordingly, the switching feature may engage the ratchet and may disengage from it after the initial relative rotation to generate the use signal has been completed, e.g. after the dose delivery operation has been commenced. After the operation, e.g. the dose delivery operation, has been completed, the switching feature may be reengaged with the ratchet, e.g. by a spring. The spring may be a coupling spring, which reestablishes the clutch interface between the first member and the second member.

In one embodiment, the power consumption, in particular the maximum power consumption, in the first state, e.g. prior to generation of the use signal, may be less than or equal to one of the following values: 300 nA, 250 nA, 200 nA (nA: nanoampere). Alternatively or additionally, in the second state, the power consumption, in particular the minimum power consumption, may be greater than or equal to one of the following values: 0.5 mA, 0.6 mA, 0.8 mA (mA: milliampere). The difference may result from the power consumption of the motion sensing unit and/or of a communication unit which may be active or operable in the second state and switched off or in a sleep state in the first state of the electronic system.

In one embodiment, the motion sensing unit, when it is active, e.g. in the second state of the system, may be operable to gather motion data or measurement data relating to the relative movement of the first and second members. The electronic control unit may be configured to convert this data into dose data, e.g. characteristic for the size of the dose which has been set or has been delivered already in the respective operation. The dose data may be calculated from the measurement data. The communication unit may be configured to transmit the dose data to an external unit, e.g. a mobile phone, tablet or personal computer.

In one embodiment, the amount or distance of the relative movement between the first and second members is characteristic for the currently set dose in a dose setting operation or for the currently dispensed dose in a dose delivery operation. The size of the dose delivered may be determined by or correspond to the distance by which a piston rod of the dose setting and/or drive mechanism is displaced distally relative to the housing during the dose delivery operation.

In one embodiment, the power consumption P2 in the second state may be greater than or equal to at least one of the following values: 2*P1, 3*P1, 4*P1, 5*P1, 10*P1, 20*P1, 30*P1, 40*P1, 50*P1, 100*P1, 500*P1, 1000*P1, 2000*P1, 5000*P1, 10000*P1 where P1 is the power consumption in the first state. In the second state, the motion sensing unit may be active and/or a communication unit, e.g. for wireless communication.

In one embodiment, the electronic system may be configured such that it is switched back to the first state of lower power consumption after a predetermined time has elapsed.

In one embodiment, the drug delivery device comprises a reservoir with a drug or a reservoir retainer configured to receive a reservoir with drug. The drug may be a liquid drug. The reservoir may comprise an amount of drug sufficient to deliver a plurality of doses. The reservoir may comprise an amount of drug sufficient to deliver a plurality of maximum settable doses. The reservoir may be a cartridge. The device may be a device for self-administration by the user, e.g. a medically trained or untrained user such as a patient. The device may be a pen-type device. The device may be a needle-based device or may be needle free. The drug delivery device may be a reusable device and/or the electronic system may be a reusable electronic system. Specifically, the electronic system is preferably designed to be used either with a plurality of disposable drug delivery devices or in a reusable drug delivery device with one or more replacement reservoirs provided once a reservoir has been emptied. The drug delivery device may be a carry-on or portable device. Consequently, the device may be a device which is carried by the user to potentially remote locations and, consequently the device may not be configured to be connected to a power supply.

It should be noted, that features which are disclosed above and below in conjunction with different embodiments and/or aspects can be combined with one another and also with other features of other aspects or embodiments.

In a particularly advantageous embodiment, an electronic system for a drug delivery device is provided, the electronic system comprising:

a dose setting and drive mechanism which is configured to perform a dose setting operation for setting a dose to be delivered by the drug delivery device and a dose delivery operation for delivering the set dose, the dose setting and drive mechanism comprising a first member and a second member wherein the dose setting and drive mechanism is configured such that, in the dose delivery operation and/or in the dose setting operation, the first member moves, e.g. rotates and/or moves axially, relative to the second member, an electronic control unit configured to control an operation of the electronic system, the electronic system having a first state and a second state, wherein the electronic system has an increased electrical power consumption in the second state as compared to the first state, an electrical use detection unit, the electrical use detection unit being operatively connected to the electronic control unit, the electrical use detection unit being configured to generate a use signal which is indicative that the user has commenced the dose setting operation or the dose delivery operation, wherein the electronic system is configured such that it is switched from the first state into the second state by the electronic control unit in response to the use signal, and wherein the electrical use detection unit is configured to generate the use signal in response to the relative movement, e.g. relative rotational movement, between the first member and the second member, preferably during the dose delivery operation.

Further aspects, embodiments and advantages will become apparent from the following description of the exemplary embodiments in conjunction with the drawings.

DETAILED DESCRIPTION

Figure 1:
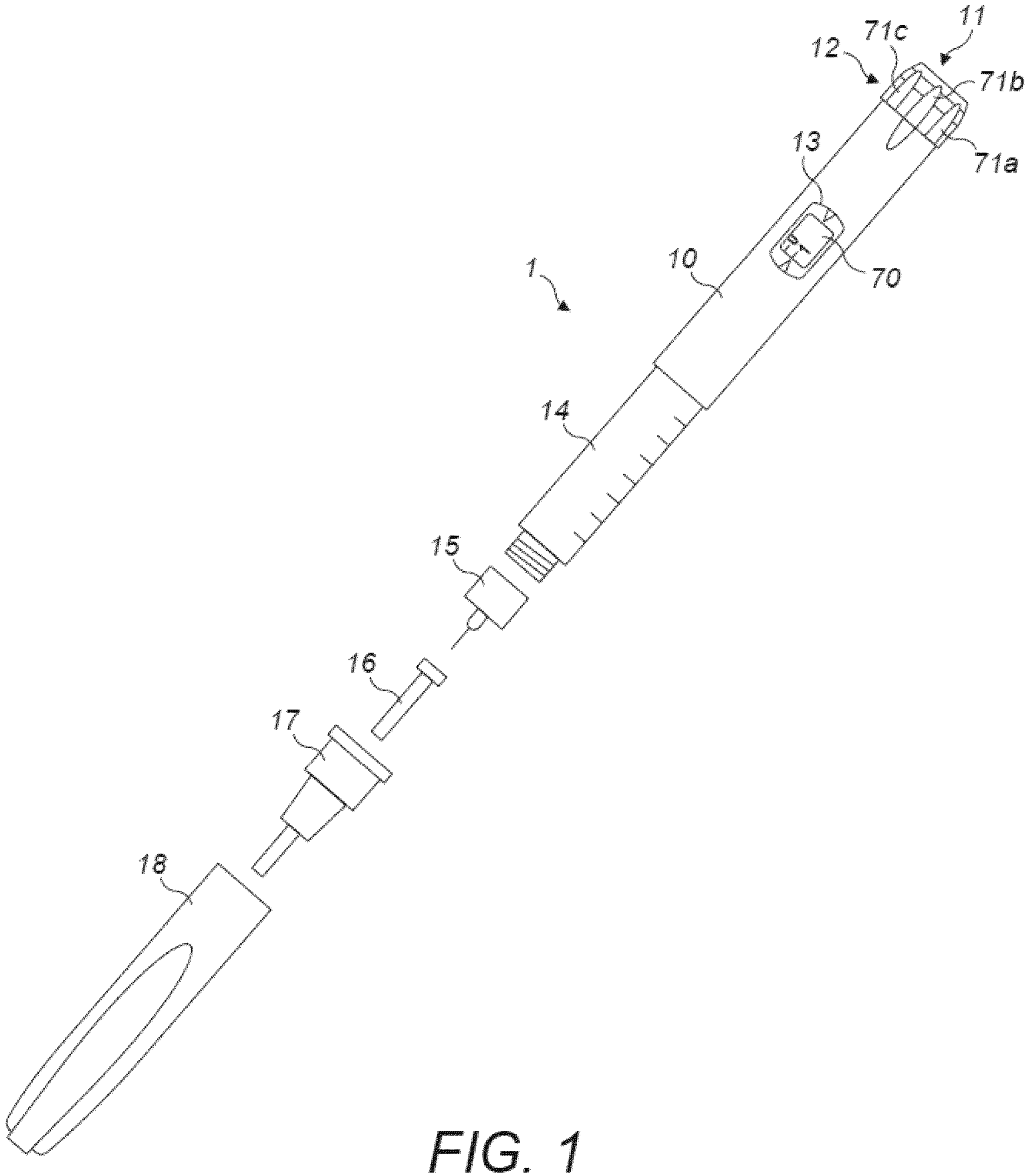
FIG. 1 shows an embodiment of a drug delivery device.

In the figures, identical elements, identically acting elements or elements of the same kind may be provided with the same reference numerals.

In the following, some embodiments will be described with reference to an insulin injection device. The present disclosure is however not limited to such application and may equally well be deployed with injection devices that are configured to eject other medicaments or drug delivery devices in general, preferably pen-type devices and/or injection devices.

Embodiments are provided in relation to injection devices, in particular to variable dose injection devices, which record and/or track data on doses delivered thereby. These data may include the size of the selected dose and/or the size of the actually delivered dose, the time and date of administration, the duration of the administration and the like. Features described herein include the arrangement of sensing elements and power management techniques (e.g. to facilitate small batteries and/or to enable efficient power usage).

Certain embodiments in this document are illustrated with respect to Sanofi's AllSTAR® injection device where an injection button and grip (dose setting member or dose setter) are combined. The injection button may provide the user interface member for initiating and/or performing a dose delivery operation of the drug delivery device. The grip or knob may provide the user interface member for initiating and/or performing a dose setting operation. Both devices are of the dial extension type, i.e. their length increases during dose setting. Other injection devices with the same kinematical behaviour of the dial extension and button during dose setting and dose expelling operational mode are known as, for example, the Kwikpen® or Savvio® device marketed by Eli Lilly and the FlexPen®, FlexTouch® or Novopen® device marketed by Novo Nordisk. An application of the general principles to these devices therefore appears straightforward and further explanations will be omitted. However, the general principles of the present disclosure are not limited to that kinematical behaviour. Certain other embodiments may be conceived for application to Sanofi's SoloSTAR® injection device where there are separate injection button and grip components/dose setting members. Thus, there may be two separate user interface members, one for the dose setting operation and one for the dose delivery operation.

"Distal" is used herein to specify directions, ends or surfaces which are arranged or are to be arranged to face or point towards a dispensing end of the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example.

FIG. 1 is an exploded view of a medicament delivery device or drug delivery device. In this example, the medicament delivery device is an injection device 1, e.g. a pen-type injector.

The injection device 1 of FIG. 1 is an injection pen that comprises a housing 10 and contains a container 14, e.g. an insulin container, or a receptacle for such a container. The container may contain a drug. A needle 15 can be affixed to the container or the receptacle. The container may be a cartridge and the receptacle may be a cartridge holder. The needle is protected by an inner needle cap 16 and either an outer needle cap 17 or another cap 18. An insulin dose to be ejected from injection device 1 can be set, programmed, or 'dialed in' by turning a dosage knob 12, and a currently programmed or set dose is then displayed via dosage window 13, for instance in multiples of units. The indicia displayed in the window may be provided on a number sleeve or dial sleeve. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a dial sleeve 70 that is configured to move when the dosage knob 12 is turned, to provide a visual indication of a currently programmed dose. The dosage knob 12 is rotated on a helical path with respect to the housing 10 when turned during programming.

In this example, the dosage knob 12 includes one or more formations **71*a*, 71*b*, 71*c*** to facilitate attachment of a data collection device.

The injection device 1 may be configured so that turning the dosage knob 12 causes a mechanical click sound to provide acoustical feedback to a user. In this embodiment, the dosage knob or dose button 12 also acts as an injection button 11. When needle 15 is stuck into a skin portion of a patient, and then dosage knob 12/injection button 11 is pushed in an axial direction, the insulin dose displayed in display window 13 will be ejected from injection device 1. When the needle 15 of injection device 1 remains for a certain time in the skin portion after the dosage knob 12 is pushed home, the dose is injected into the patient's body. Ejection of the insulin dose may also cause a mechanical click sound, which is however different from the sounds produced when rotating the dosage knob 12 during dialing of the dose.

In this embodiment, during delivery of the insulin dose, the dosage knob 12 is returned to its initial position in an axial movement, without rotation, while the dial sleeve 70 is rotated to return to its initial position, e.g. to display a dose of zero units. As noted already, the disclosure is not restricted to insulin but should encompass all drugs in the drug container 14, especially liquid drugs or drug formulations.

Injection device 1 may be used for several injection processes until either the insulin container 14 is empty or the expiration date of the medicament in the injection device 1 (e.g. 28 days after the first use) is reached.

Furthermore, before using injection device 1 for the first time, it may be necessary to perform a so-called "prime shot" to ensure fluid is flowing correctly from insulin container 14 and needle 15, for instance by selecting two units of insulin and pressing dosage knob 12 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user.

As explained above, the dosage knob 12 also functions as an injection button 11 so that the same component is used for dialling/setting the dose and dispensing/delivering the dose.

Figure 2:
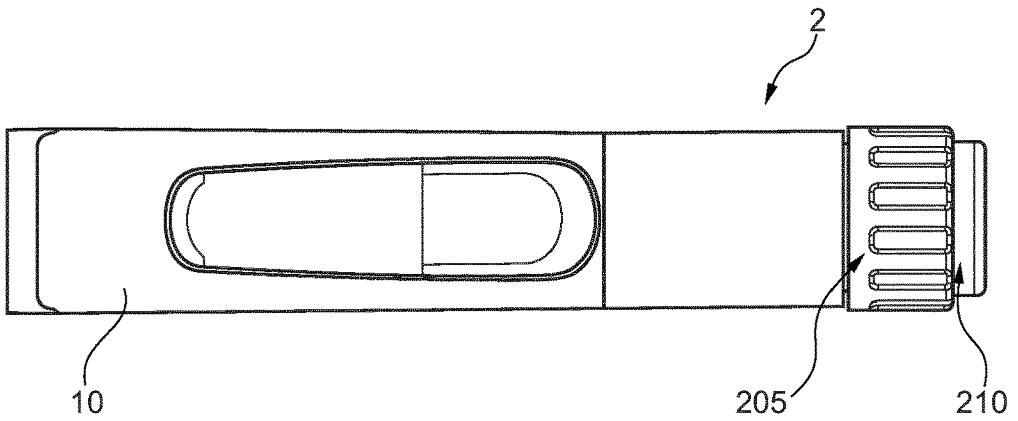
FIG. 2 shows a proximal end of a drug delivery device according to another embodiment.
Figure 3A:
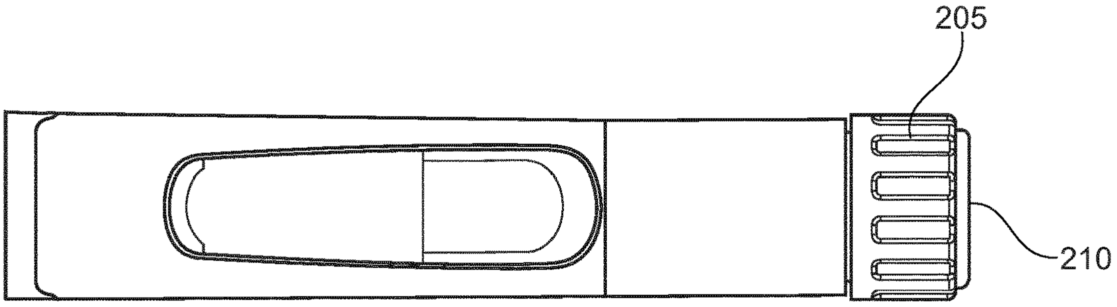
FIG. 3A shows a proximal end of the injection device of FIG. 2 after actuation of an injection button.
Figure 3B:
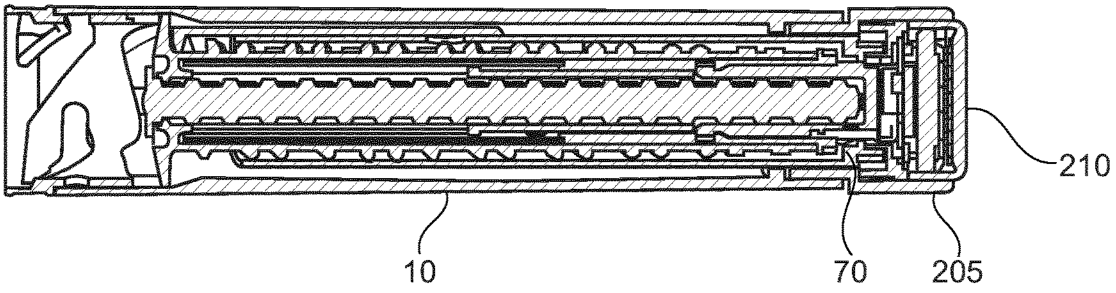
FIG. 3B is a cross-sectional view of the device of FIG. 2 after actuation of the injection button.

FIGS. 2, 3A and 3B show the proximal end of a device 2 according to a second embodiment. The device 2 comprises a grip 205 and injection button 210. Unlike the device 1 shown in FIG. 1, the injection button 210 is separate from the grip 205 which is used to dial the dosage.

The dial sleeve 70 and injection button 210 are located partially inside the grip 205. The grip 205 and dial sleeve 70 may be considered functionally as elements of the same component. Indeed, the grip 205 and dial sleeve 70 may only be separate components for assembly reasons. Aside from the differences described herein, the device 2 shown in FIG. 2 operates in substantially the same way as the device 1 shown in FIG. 1.

Similarly to the device 1, the dial sleeve 70, grip 205 and injection button 210 extend helically from the device 2. During a dose-dialling mode of operation (as shown in FIG. 2) there is no relative rotation between the injection button 210 and the dial sleeve 70. The dose is dialled by rotating the grip 205 (thereby also rotating the dial sleeve 70 and injection button 210) with respect to the rest of the device 2.

To initiate dispensing of a medicament, the injection button 210 is pressed axially, as shown in FIGS. 3A and 3B. This action changes the mode of the device 2 to a dispensing mode. In dispensing mode the dial sleeve 70 and grip component 205 retract along a helical path into the rest of the device 2, whereas the injection button 210 does not rotate and only retracts with axial motion. Thereby, in dispensing mode, there is a disengagement of the injection button 210 leading to relative rotation of the injection button 210 with respect to the dial sleeve 70. This disengagement of the injection button 210 with respect to the dial sleeve 70 is caused by a clutch arrangement or interface described in more detail in relation to FIGS. 8A-C.

Figure 4:
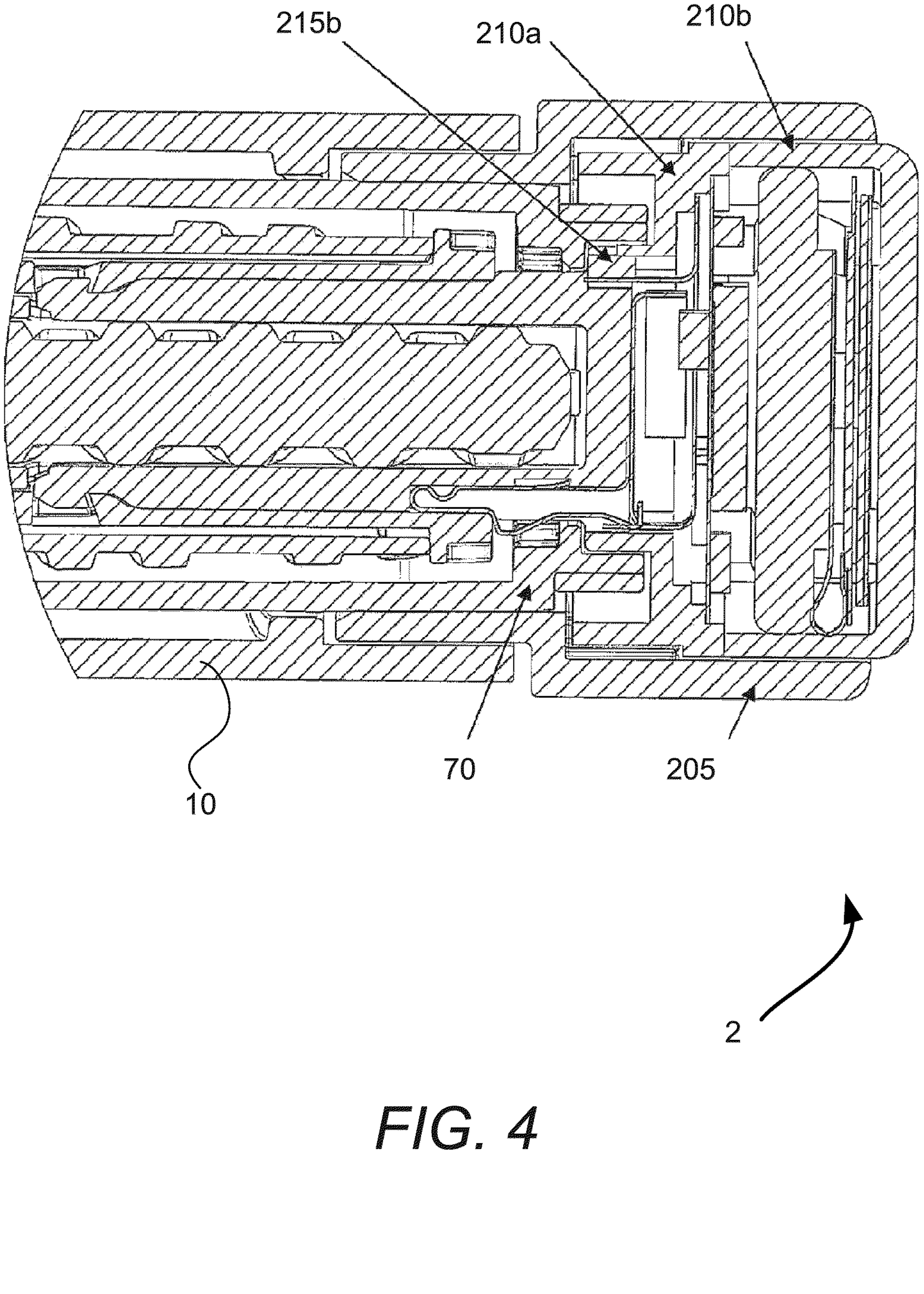
FIG. 4 is a zoomed-in cross-sectional view of the device of FIG. 2.

FIG. 4 is a close-up cross sectional view of the proximal end of the device 2 shown in FIG. 3 after the injection button 210 has been pressed. As shown in FIG. 4, the injection button 210 is configured as two separate sub-components, namely a distal or lower button part **210*a* and a proximal or upper button part 210*b*. The injection button 210 may be configured in this way to aid the assembly process. The distal button part 210*a* and proximal button part 210*b* may be fixed together and act functionally as a single component, i.e. the injection button 210**.

A sensor arrangement 215 comprising one or more sensors is mounted in the injection button 210 which is configured to sense the relative rotational position of the dial sleeve 70 relative to the injection button 210. This relative rotation can be equated to the size of the dose dispensed and used for the purpose of generating and storing or displaying dose history information. The sensor arrangement 215 may comprise a primary sensor 215*a* and a secondary sensor 215*b*. In FIG. 4, only the secondary sensor 215*b* is shown. In the following discussion, these sensors are optical sensors however multiple alternative options are equally applicable to various embodiments such as photoelectric sensors, inductive sensors, capacitive sensors, contact sensors, contactless sensors, magnetic sensors and so forth.

Figure 5:
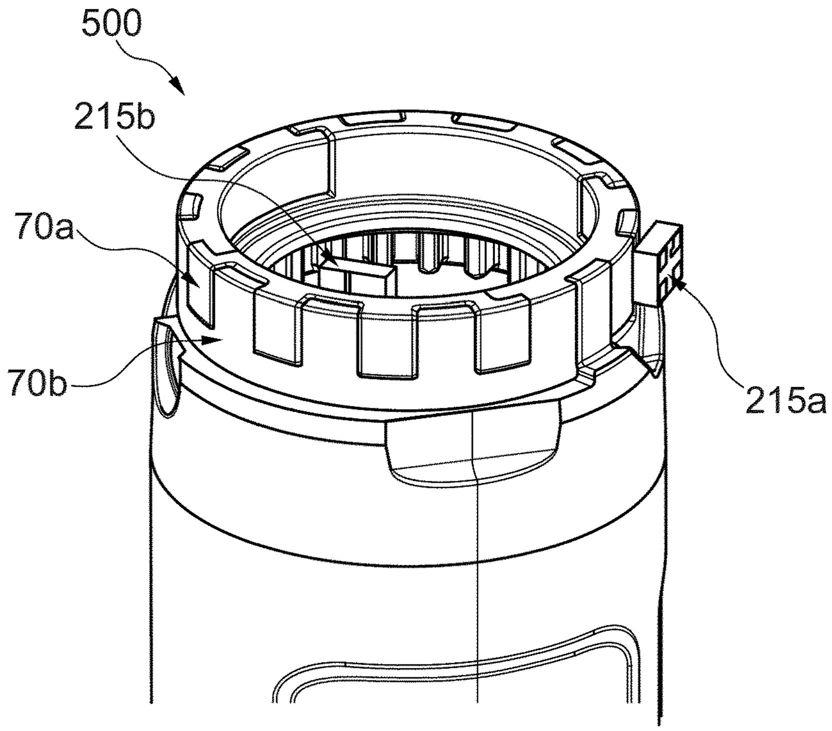
FIG. 5 is an elevated side view of a first type of encoder system.
Figure 6:
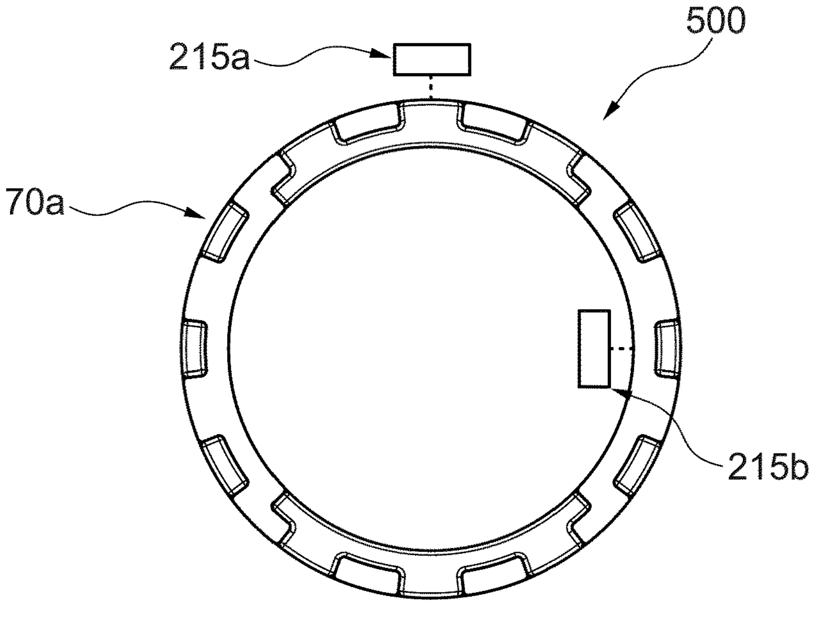
FIG. 6 is a plan view of the encoder system shown in FIG. 5.

FIGS. 5 and 6 show an encoder system 500 according to certain embodiments. The encoder system is configured for use with the device 2 described above. As shown in FIG. 5 and FIG. 6, the primary sensor 215*a* and secondary sensor 215*b* are configured to target specially adapted regions at the proximal end of the dial sleeve 70. In this embodiment, the primary sensor 215*a* and secondary sensor 215*b* are infrared (IR) reflective sensors. Therefore, the specially adapted proximal regions of the dial sleeve 70 are divided into a reflective area 70*a* and a non-reflective (or absorbent) area 70*b*. The part of the dial sleeve 70 comprising the reflective area 70*a* and a non-reflective (or absorbent) area 70*b* may be termed an encoder ring.

To keep production costs to a minimum, it may be favourable to form these areas 70*a*, 70*b* from injection moulded polymer. In the case of polymer materials, the absorbency and reflectivity could be controlled with additives, for example carbon black for absorbency and titanium oxide for reflectivity. Alternative implementations are possible whereby the absorbent regions are moulded polymer material and the reflective regions are made from metal (either an additional metal component, or selective metallisation of segments of the polymer dial sleeve 70).

Having two sensors facilitates a power management technique described below. The primary sensor 215*a* is arranged to target a series of alternating reflective regions 70*a* and non-reflective regions 70*b* at a frequency commensurate with the resolution required for the dose history requirements applicable to a particular drug or dosing regime, for example, 1 IU. The secondary sensor 215*b* is arranged to target a series of alternating reflective regions 70*a* and non-reflective regions 70*b* at a reduced frequency compared to the primary sensor 215*a*. It should be understood that the encoder system 500 could function with only a primary sensor 215*a* to measure the dispensed dose. The secondary sensor 215*b* facilitates the power management technique described below.

The two sets of encoded regions 70*a*, 70*b* are shown in FIGS. 5 and 6 concentrically with one external and the other internal. However, any suitable arrangement of the two encoded regions 70*a*, 70*b* is possible. Whilst the regions 70*a*, 70*b* are shown as castellated regions, it should be borne in mind that other shapes and configurations are possible.

Figure 7:
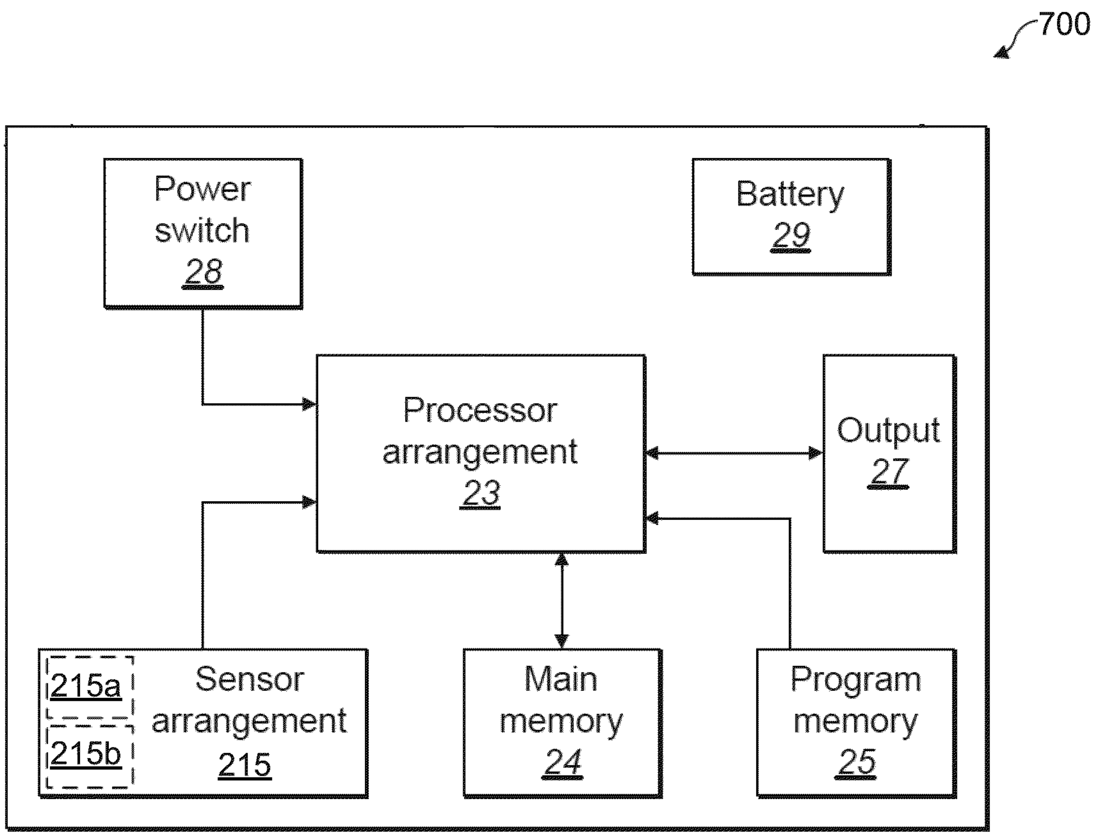
FIG. 7 is a schematic block diagram of a device controller.

The devices 1, 2 also include a controller 700, as shown schematically in FIG. 7. The controller 700 comprises a processor arrangement 23 including one or more processors, such as a microprocessor, a Digital Signal Processor (DSP), Application Specific Integrated Circuit (ASIC), Field Programmable Gate Array (FPGA) or the like, together with memory units 24, 25, including program memory 25 and main memory 24, which can store software for execution by the processor arrangement 23.

The controller 700 controls a sensor arrangement 215, comprising one or more sensors 215*a*, 215*b*.

An output 27 is provided, which may be a wireless communications interface for communicating with another device via a wireless network such as Wi-Fi or Bluetooth®, or an interface for a wired communications link, such as a socket for receiving a Universal Series Bus (USB), mini-USB or micro-USB connector. For example, data may be output to a data collection device attached to the device 1, 2.

A power switch 28 is also provided, together with a battery 29 as power supply.

It is advantageous to be able to minimise the power usage of the encoder system 500 so that the size of a battery 29 needed to be packaged into the device 1, 2 can be minimised. The sensors 215*a*, 215*b* used in this embodiment require a certain amount of power to operate. This embodiment is arranged such that the sensors 215*a*, 215*b* can be switched on and off intermittently at a controlled frequency (i.e. in a strobe-sampling mode). There is inherently a limit to the maximum rotational speed that can be counted by a sampled encoder system before aliasing occurs. Aliasing is the phenomenon where the sampling rate is less than the rate at which sensed regions pass the sensor which means that a miscount could occur when a region change is missed. The secondary sensor 215*b* with a reduced frequency compared to the primary frequency 215*a* can tolerate a higher rotational speed before it too becomes aliased. Whilst the secondary sensor 215*b* is not able to resolve the dose dispensed to the same resolution as the primary sensor 215*a*, the output of the secondary sensor 215*b* remains reliable at higher speeds. Therefore both sensors 215*a*, 215*b* are used in combination to be able to accurately determine dose delivered up to a first threshold rotational (dispensing) speed. The sensors 215*a*, 215*b* can then be used to determine an approximate dose delivered up to a second (higher) threshold dosing speed. At speeds above the second threshold speed the sensors 215*a*, 215*b* will not be able to accurately or approximately determine the dose delivered, therefore the second threshold is set above a speed which is not physically possible when ejecting fluid from the injection device 1, 2.

The first speed threshold is determined by the sampling rate of primary sensor 215*a* and the frequency of encoder region transitions, which is fixed at the resolution required by the intended drug or dosing regime (for example one transition per 1 IU). The second speed threshold is determined by the sampling rate of the secondary sensor 215*b* and the frequency of encoder region transitions. The first threshold is set such that the largest range of dispensing speeds can be covered by the system for accurate reporting of dose dispensed.

The example embodiment shown in FIG. 6 has primary sensor 215*a* targeting region transitions at 1 transition per 1 IU of dose delivered and the secondary sensor 215*b* targeting region transitions at 1 transition per 6 IU of dose delivered. Other options are possible which include 1 transition per 2 IU, 1 transition per 4 IU, 1 transition per 8 IU and 1 transition per IU units. These options are each possible because there are 24 separate regions 70*a*, 70*b* per revolution in the encoder system 500 shown in FIG. 6. In general, if the number of separate regions 70*a*, 70*b* per revolution were n units then there would be options at one region transition per m units where m was any integer factor of n greater than 1 and less than n.

The slower the sampling frequency of both sensors 215*a*, 215*b*, the lower the power consumption required and therefore the smaller the required size of the battery 29. It is therefore optimal to minimise, by design, the sampling frequency as far as is practical.

In order to further limit the battery capacity requirement, it is advantageous to be able to have the device 2 in a low power state when the sensors 215*a*, 215*b* are not required to be energised. This may be achieved with a switch activated by the displacement of the injection button 210.

Figure 8A:
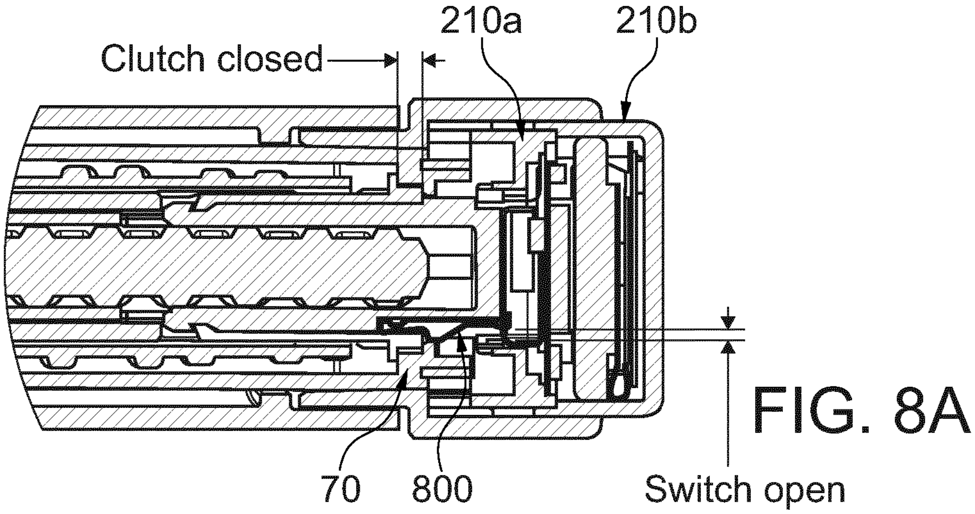
FIG. 8A is a cross-sectional view of the proximal end of a device before actuation of an injection button.
Figure 8B:
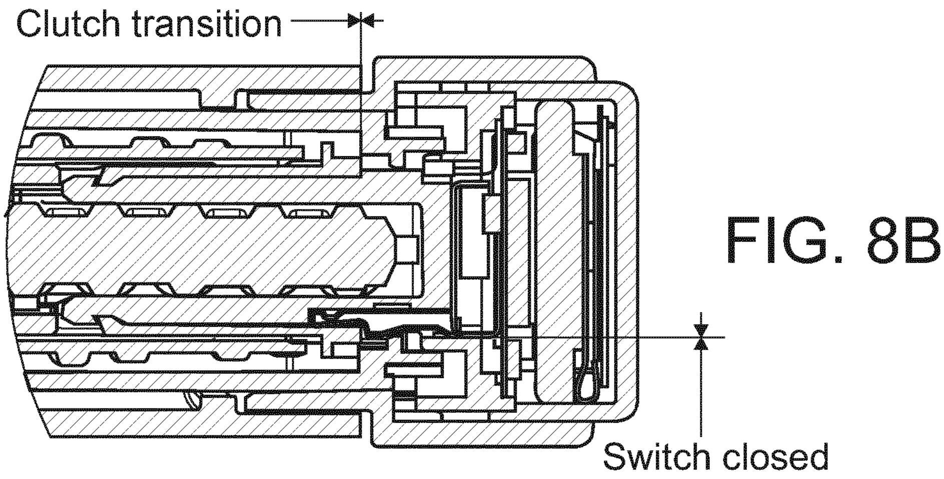
FIG. 8B is a cross-sectional view of the proximal end of a device during partial actuation of an injection button.
Figure 8C:
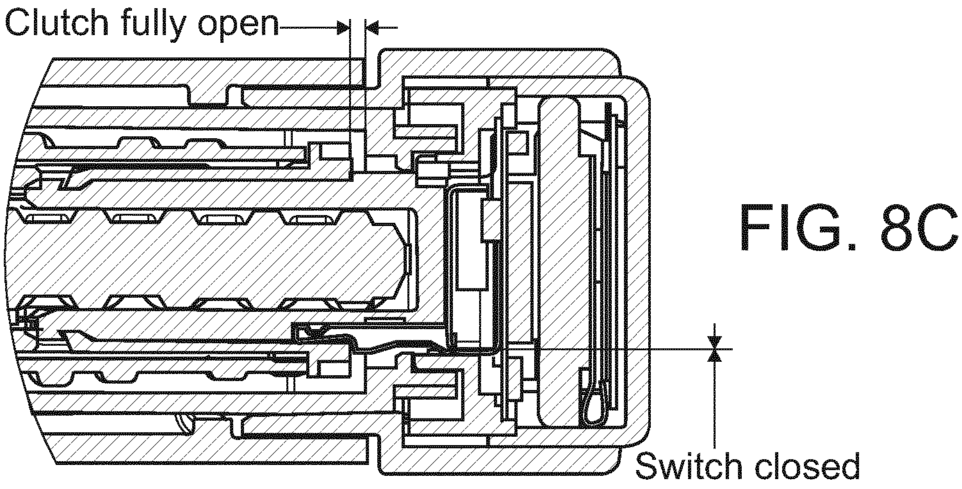
FIG. 8C is a cross-sectional view of the proximal end of a device during full actuation of an injection button.

As shown in FIG. 8A, a switch 800 is mounted in the injection button 210. In the configuration shown in FIG. 8A, an arm of the switch 800 is deflected by the dial sleeve 70 so that the switch 800 is in an open state. In this configuration a clutch between a clutch component and the dial sleeve 70 is engaged with the device 2 in its dialling mode. As the injection button 210 is pressed the injection button 210 is displaced axially with respect to the dial sleeve 70, therefore the switch 800 is displaced axially relative to the dial sleeve 70. This displacement causes a part on the dial sleeve 70 to ride down a cam surface on the switch 800, allowing the switch arm to deflect towards its free state. This deflection in the switch arm has the effect of changing the electrical state of the switch 800 (for example to electrically closed). The design is arranged such that the electrical change of state of the switch 800 happens before the state change in the clutch between the clutch component and dial sleeve 70. FIG. 8B shows the transition point of the clutch and shows that the switch 800 has already changed state. FIG. 8C shows the state of the device 2 with the injection button 210 fully pressed. In this condition, the clutch is fully separated allowing the clutch component and dial sleeve 70 to rotate relative to each other in the dispense mode.

This sequence operates in reverse when the injection button 210 is released.

The change in electrical state that occurs when the injection button 210 is pressed thereby allowing the device 2 to be powered down into a low energy consumption state when the injection button 210 is not pressed. Relative rotation between the injection button 210 and dial sleeve 70 is not possible in this state, therefore the encoder system 500 is not required.

It is possible for the mechanical configuration between the dial sleeve 70 and the switch 800 to operate in the opposite sense such that the arm of the switch 800 is deflected during dispensing rather than during dialling.

The following embodiments relate to an alternative sensing technique to determine the number of medicament units that have been dispensed from the device 1, 2.

As with the embodiments described above, two sensors 215 are mounted in the injection button 210 and are configured to sense the relative rotational position of the dial sleeve 70 relative to the injection button 210 during the dispensing of a dose. This relative rotation can be equated to the size of the dose dispensed and used for the purpose of generating and storing or displaying dose history information.

Figure 9:
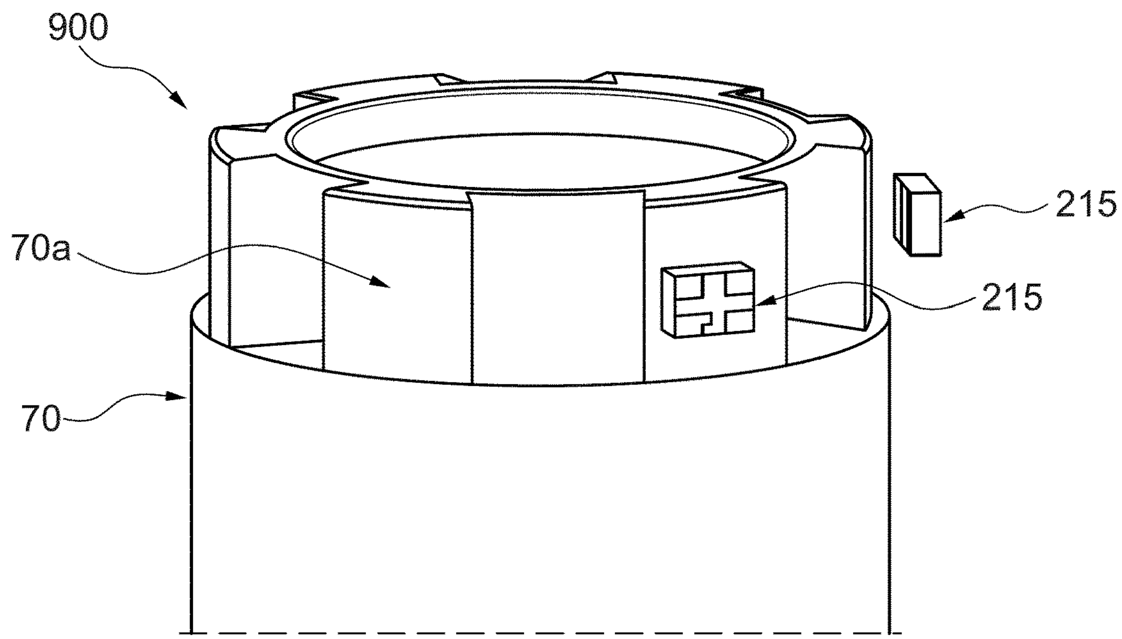
FIG. 9 is an elevated side view of a second type of encoder system.

As shown in FIG. 9, the two sensors 215 from this embodiment are configured to target specially adapted regions 70*a*, 70*b* of the dial sleeve 70. In this embodiment IR reflective sensors are used, therefore the regions of the dial sleeve 70 are divided into reflective and absorbent segments 70*a*, 70*b*. The segments 70*a*, 70*b* may also be referred to herein as flags or detection regions.

Figure 10:
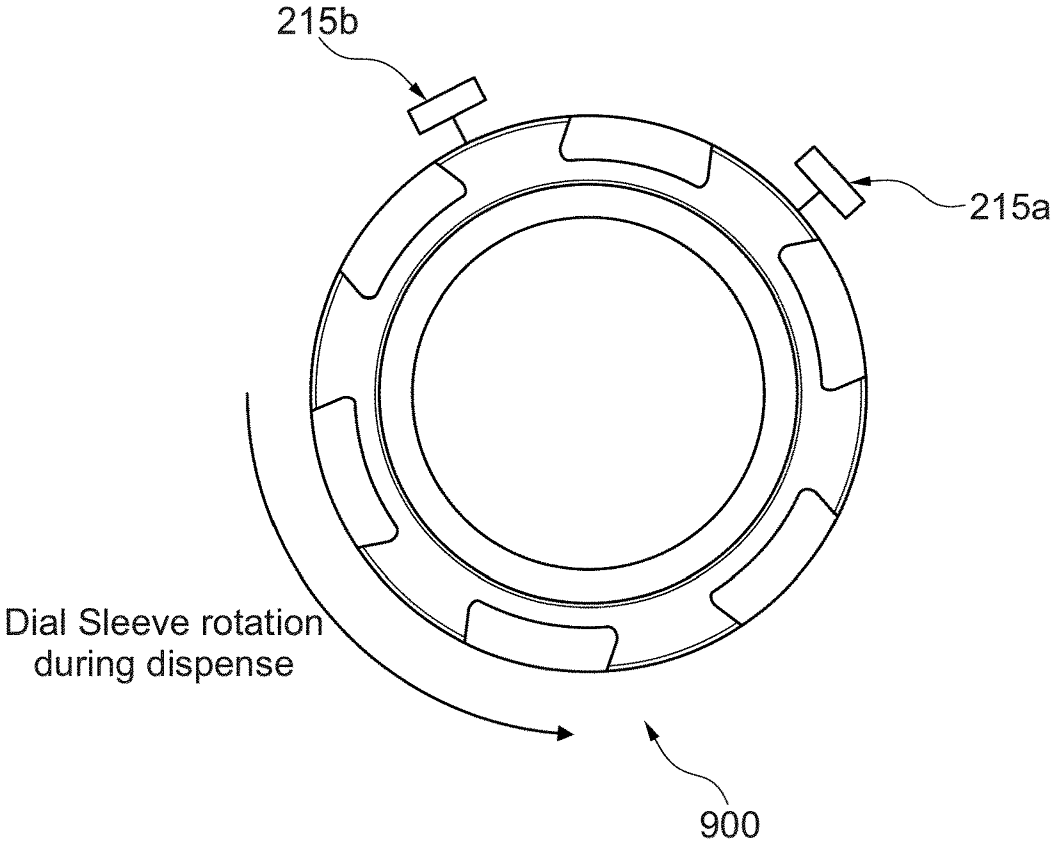
FIG. 10 is a plan view of the encoder system shown in FIG. 9.

Unlike the encoder system 500 described above in relation to FIGS. 5 and 6, the encoder system 900 shown in FIGS. 9 and 10 has both IR sensors 215 target the same type of region 70*a*, 70*b*. In other words, the sensors 215 are arranged so that they face reflective regions 70*a* and absorbent regions 70*b* on the same surface. The sensors 215 may be arranged such that, at the same time, one sensor faces a reflective region 70*a* and one sensor faces an absorbent region. During the dispensing of a dose, the dial sleeve 70 rotates anti-clockwise 15° relative to the injection button 210 for every medicament unit that has been dispensed. The alternate flag elements are in 30° (or two unit) sections. The sensors 215 are arranged to be out of phase with each other, such that the angle between them equates to an odd number of units (e.g. 15°, 45°, 75°, etc.), as shown in FIG. 10.

The encoder system 900 shown in FIG. 10 has 12 segments per revolution, i.e. 12 alternating regions 70*a*, 70*b*. In general, embodiments work with any multiple of 4 units per revolution. The angle, a, between sensors 215 can be expressed by Equation 1, where both m and n are any integers and there are 4m units dispensed per revolution.

$$\alpha = (2n-1)\frac{360}{4m} \qquad \text{Equation 1}$$

Angle between sensors

Figure 11:
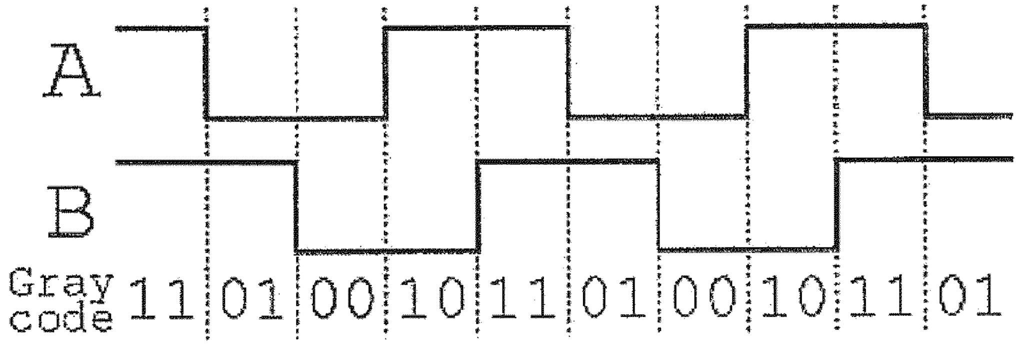
FIG. 11 illustrates a gray code output.

FIG. 11 shows how the outputs for a Sensor A and Sensor B change as the dial sleeve 70 rotates anti-clockwise during dispensing of a medicament.

In combination, the two sensors A, B produce a 2-bit Gray code output (11, 01, 00, 10). The 2-bit code sequence repeats every four units dispensed. This coded output facilitates the detection of positive (anticlockwise) and negative (clockwise) rotations. For example, when the sensors read '11' a change to '01' would be a positive rotation and the change to '10' would be a negative rotation. This directionally sensitive system has advantages over a purely incremental system, in the ability to accurately determine true dispensed dose volume in the cases where negative rotations can occur. For example, in mechanisms that over rotate at the end of dose stop before 'backing-off' when the user releases the injection button 210.

Figure 12:
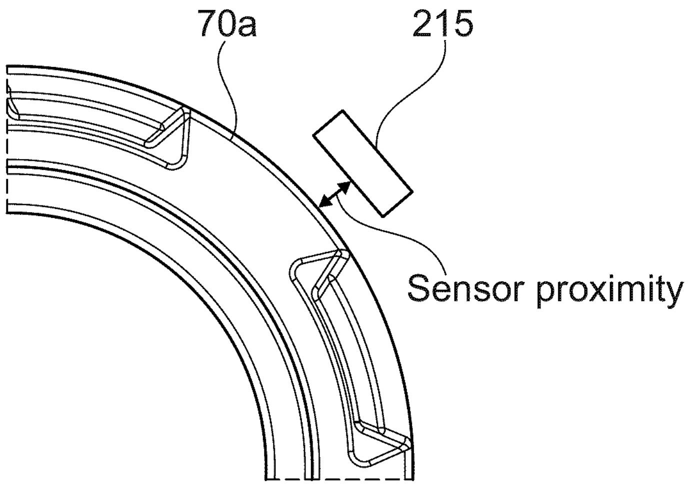
FIG. 12 is a partial plan view of an encoder system.

Referring to FIG. 12, the IR sensors 215 emit IR light from an LED. The IR reflective regions 70*a* of the encoder system 900 reflect the light and the sensors detect the reflected light. The sensors 215 then convert the detected light to an electrical output. The strength of the IR light that is detected by the sensor 215 after reflecting off the encoder ring is proportional to the proximity of the sensor to the encoder ring. Therefore it is desirable for the sensor 215 to be as radially close to the encoder ring as possible without contacting the encoder ring, which would add frictional losses to the dispense mechanism.

Figure 13:
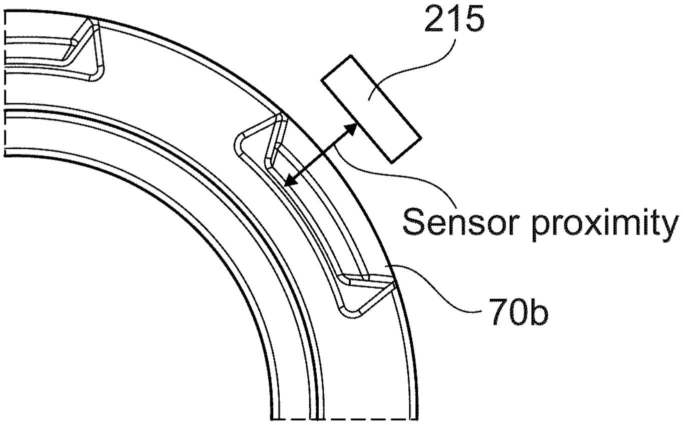
FIG. 13 is a partial plan view of an encoder system.

Referring to FIG. 13, the IR absorbent regions 70*b* of the dial sleeve 70 do not completely absorb all the IR light emitted from the sensor 215. Testing shows that when the sensor 215 is aligned with the absorbent regions 70*b* of the dial sleeve 70 the sensors 215 have some electrical output due to the low level of IR light reflected by the dial sleeve 70. Therefore, the dial sleeve flags have been designed to maximise the distance between the sensor 215 and any intentionally IR absorbent parts of the encoder ring. This ensures a high contrast ratio and signal sharpness.

As a dose is dispensed, the software of the device 1, 2 monitors the electrical output of the sensors 215. The software detects changes between high and low outputs to determine when the relative rotation between the dial sleeve 70 and injection button 210 has reached an additional 15° (i.e. an additional one unit has been dispensed). Therefore it is beneficial to the function of the device for the contrast ratio between the high and low outputs to be as large as possible.

According to various embodiments, the design of the dial sleeve 70 and encoder ring flags 70a, 70b has been developed to increase the contrast ratio. The design shown in FIG. 14 has the absorbent dial sleeve flags 70b removed to leave gaps 140 between adjacent encoder ring flags 70a. This maximises the distance between the sensor 215 and any material which could reflect any of the IR light emitted from the sensor.

Figure 15A:
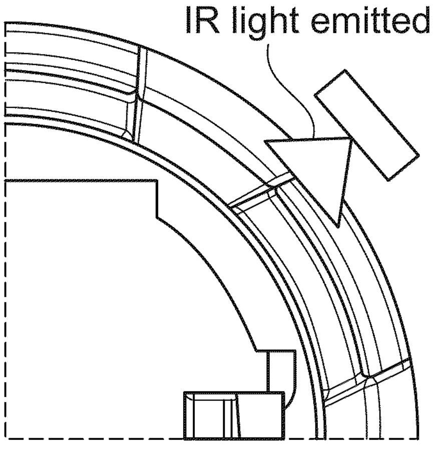
FIG. 15A is a partial plan view of an encoder system.

This design increases the contrast ratio between the low and high sensor electrical outputs. However, as FIG. 15A shows, the IR light emitted by the sensor 215 is not a beam, such that as the dial sleeve 70 rotates between a reflective encoder ring flag 70a and a gap 140, there is overlap where the sensor 215 detects some of the light emitted by the sensor 215. During this period, the sensor output gradually decreases from high to low, rather than an immediate step change between high and low. This gradual decrease is more difficult for the software to determine as a 15° rotation (i.e. one medicament unit dispensed), than an immediate step change.

Figure 14:
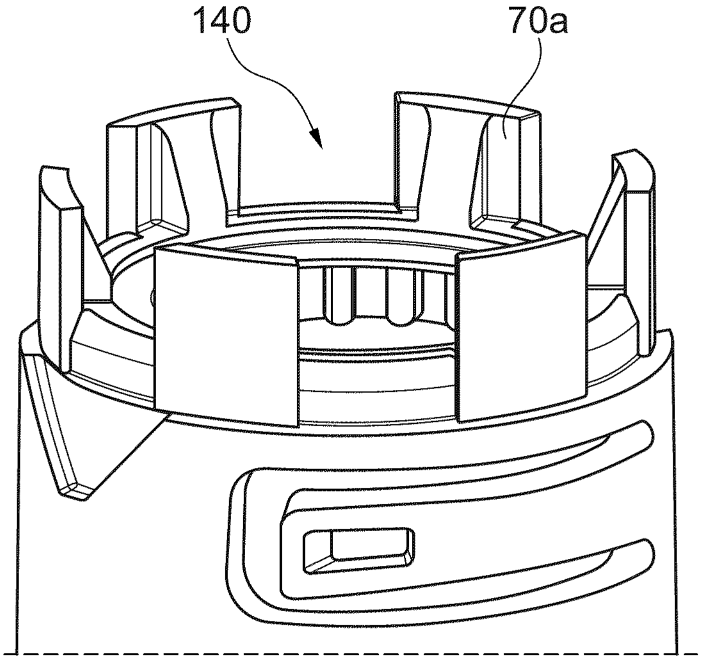
FIG. 14 is an elevated side view of a third type of encoder system.
Figure 15B:
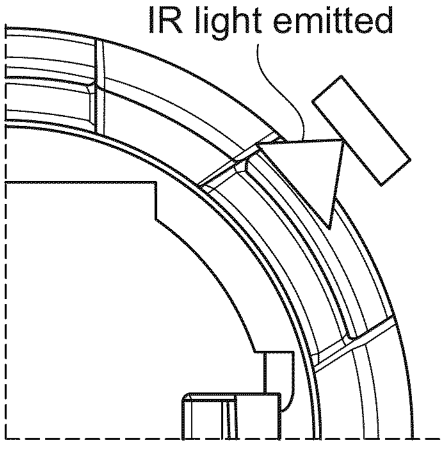
FIG. 15B is a partial plan view of an encoder system.

This phenomenon occurs with various embodiments of the encoder flags (as shown in FIG. 9 and FIG. 14). However, as shown in FIG. 15B, in accordance with certain embodiments, the rotation of the dial sleeve 70 that is required before the sensor output completely switches to a low output is increased due to the visibility of the sides of the reflective encoder ring flags 70a.

Figure 16:
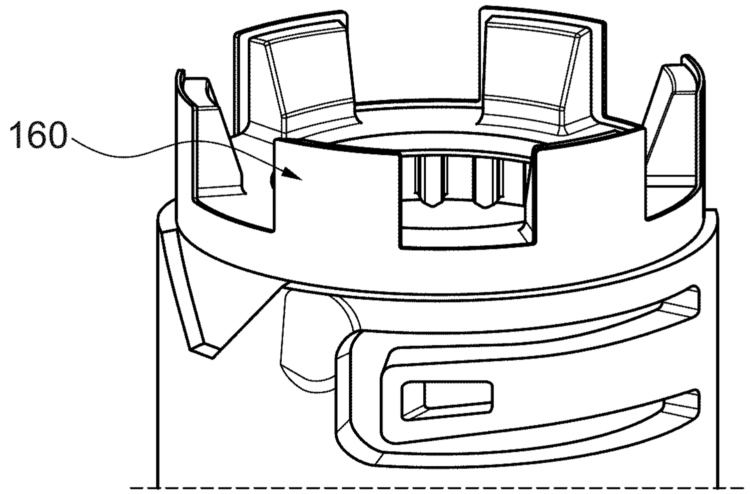
FIG. 16 is an elevated side view of a fourth type of encoder system.
Figure 17:
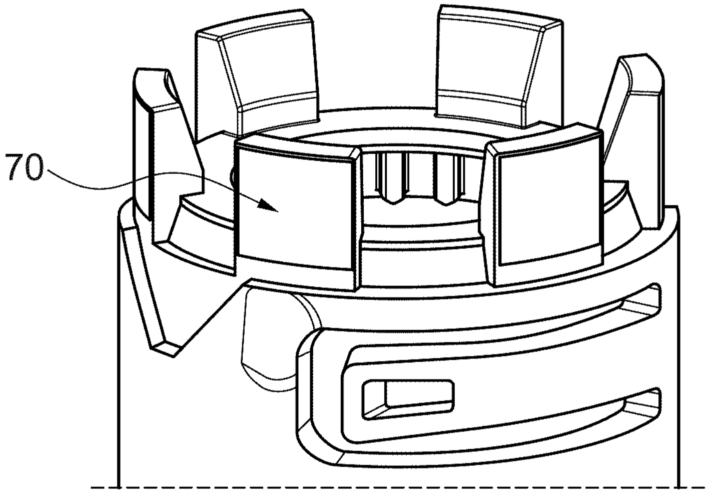
FIG. 17 is an elevated side view of a fifth type of encoder system.

Therefore, it is advantageous to reduce the thickness at the edges of the IR reflective flags 70a on the encoder ring. FIG. 16 and FIG. 17 show two possible embodiments to reduce the thickness at the lateral edges of the IR reflective flags 70a on the encoder ring so that the reflective surfaces are inclined inwardly for preventing or reducing scattered reflection, thereby enhancing contrast transition and signal sharpness.

FIG. 16 shows an embodiment where the moulded polymer encoder ring has been replaced with a formed metal ring 160.

FIG. 17 shows an embodiment where the moulded polymer encoder ring has been replaced by sections of the dial sleeve 70 that have been printed, painted or coated with IR reflective material.

Figure 18A:
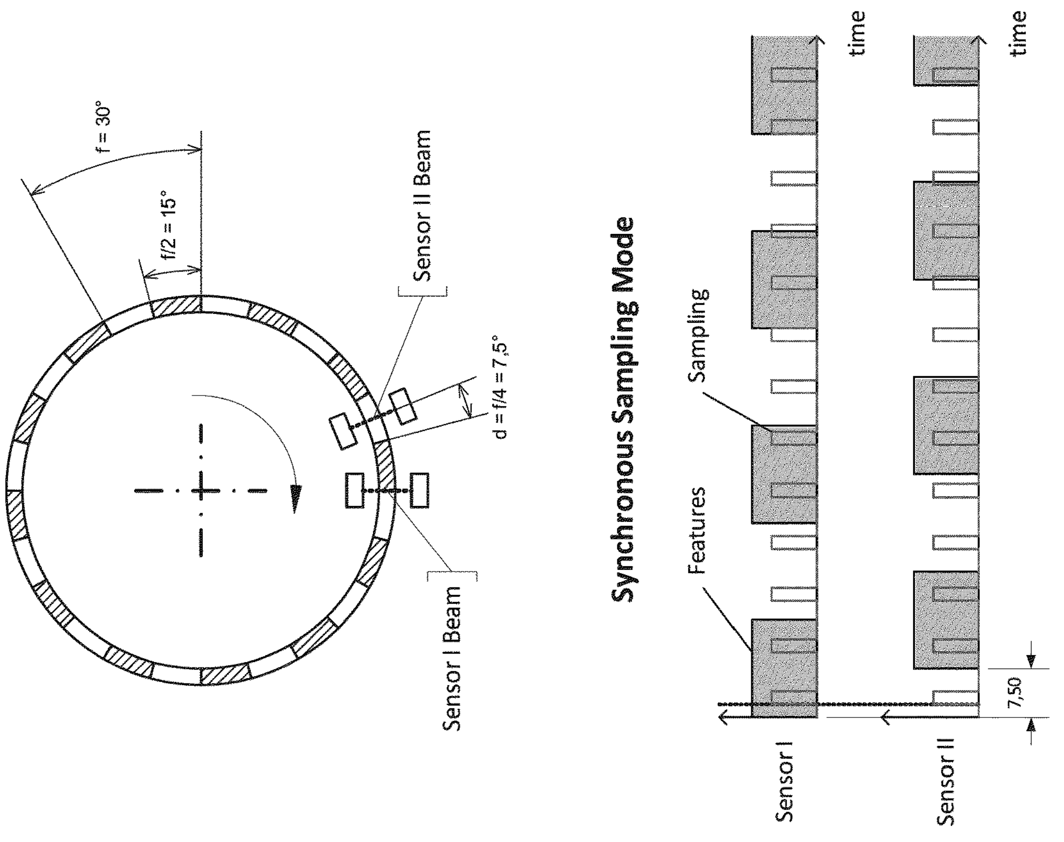
FIG. 18A is a plan view of a sixth type of encoder system.
Figure 18B:
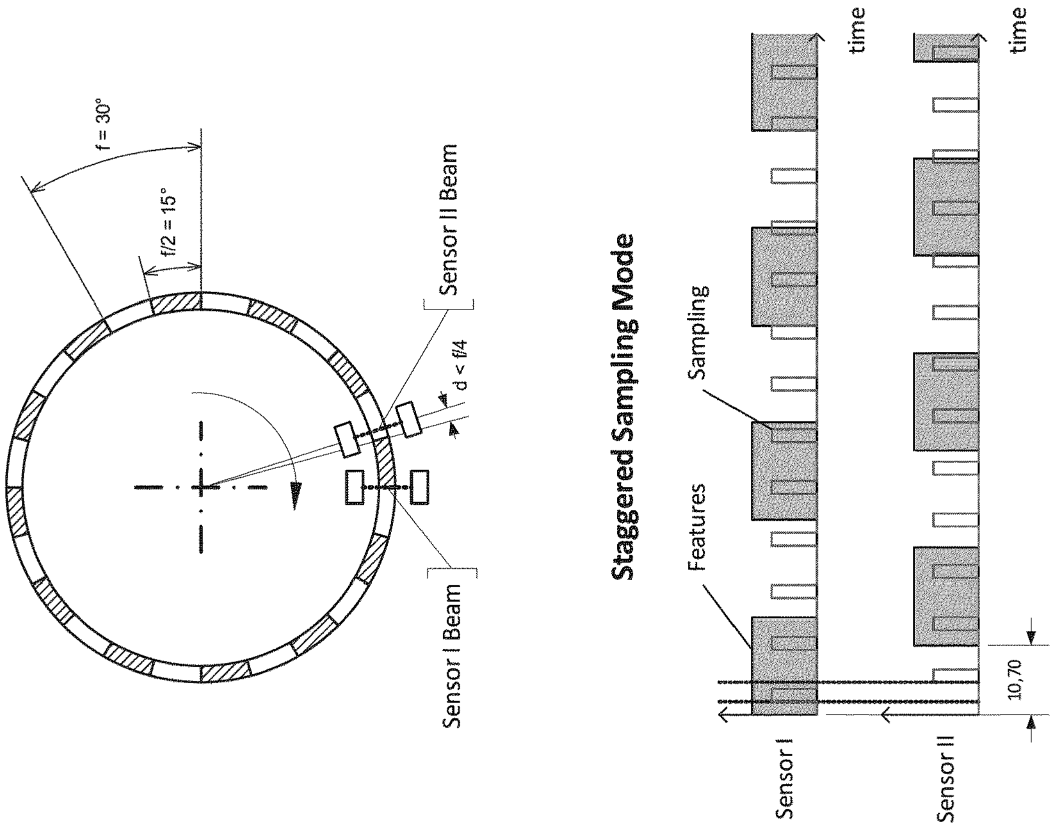
FIG. 18B is a plan view of a seventh type of encoder system.

FIGS. 18A and 18B illustrate two alternative modes of operation in accordance with various embodiments. Referring to FIG. 18A, Sensor I and Sensor II are provided having an angular offset (δ) is half of the periodicity (ϕ) of the encoded regions of the encoder ring. In this embodiment, the sensors are operated to sample synchronously, i.e. at the same times ($t_1$, $t_2$, $t_3$, . . . ).

FIG. 18A illustrates an embodiment where the angular offset (δ) differs from half of the feature periodicity (ϕ/2) and the sensors are operated in a staggered mode with an offset in time (Δt) between samplings. This may be used to achieve more balanced overall system LED power consumption than available in synchronous operation.

In the configuration shown in FIG. 18B, the amount of the angular offset (δ) may be decreased below half of the feature periodicity (ϕ) in order to compensate for the relative angular travel during the offset in time (Δt) between the sampling operations of the different sensors.

The offset in time (Δt) may be adjusted according to an estimated value for the relative rotational speed (ω) of the encoder ring which may be calculated from the sensor measurements. In particular, the offset time (Δt) may be decreased when an increase in rotational speed (ω) is determined.

Figure 19A:
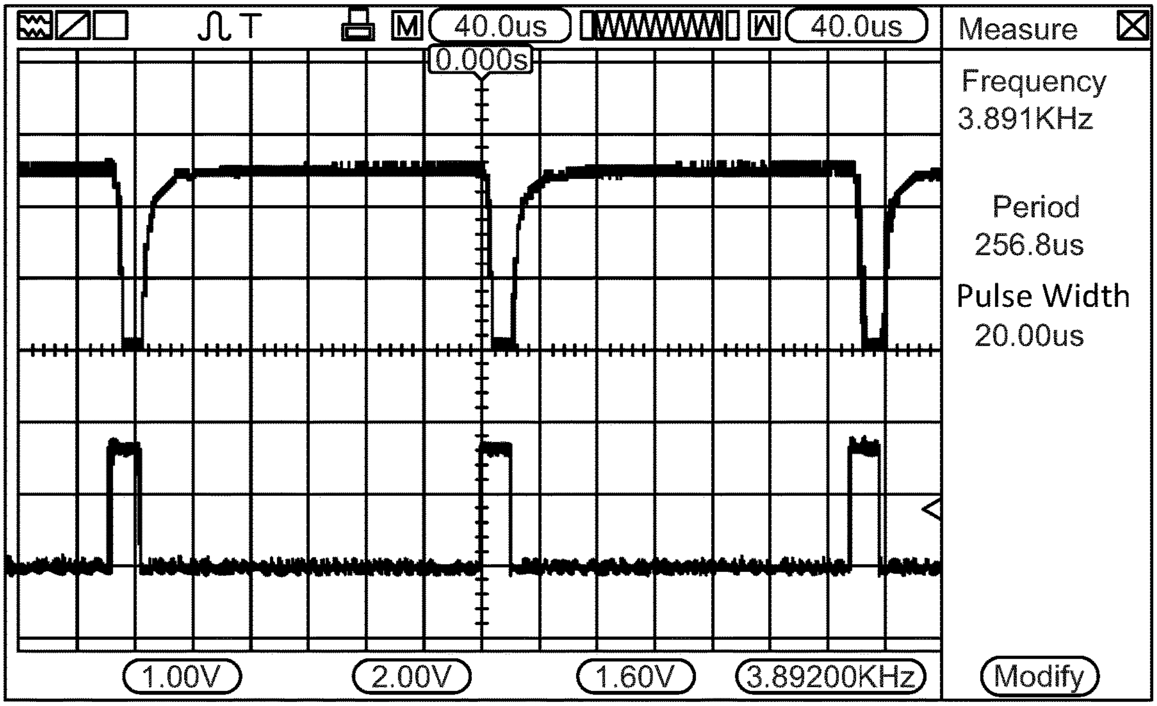
FIG. 19A is a screenshot showing scope traces obtained from various embodiments.

FIG. 19A shows scope traces obtained by embodiments of the disclosure. The lower trace is the LED driving signal and the upper trace is the output from the current mirror before the Schmitt trigger.

Figure 19B:
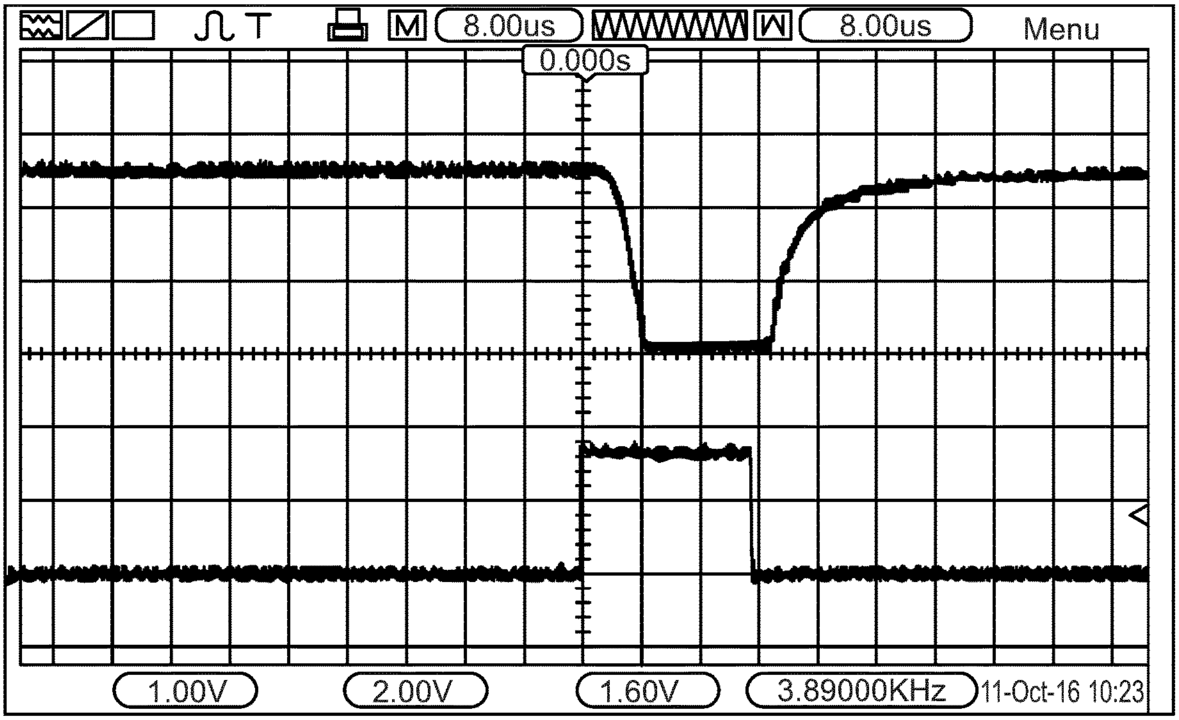
FIG. 19B is a close-up view of the screenshot of FIG. 19A.

FIG. 19B is a zoomed-in view of the scope traces shown in FIG. 19A. Results show that it is possible to sample at 256 μs with a nearly 12-to-1 duty cycle (meaning the average current is $1/12^{th}$ of the 4 mA LED drive, thereby saving power and cell capacity. This is equivalent to a sample rate of over 3900 Hz and with one unit per segment and a minimum of two samples per segment a detection speed in excess of 1950 units per second is achieved without violating the Nyquist criterion. As such, no anti-aliasing detector is required.

While the embodiments above have been described in relation to collecting data from an insulin injector pen, it is noted that embodiments of the disclosure may be used for other purposes, such as monitoring of injections of other medicaments, for example, or drug delivery devices in general.

As has been discussed above, managing electrical power consumption or the resources of a power supply (e.g. a rechargeable or non-rechargeable battery 29) in drug delivery devices comprising electronic systems, such as the injection devices discussed further above, is a problem which needs to be addressed, e.g. in order to optimize the use of the capacity of the power supply and/or in consideration of the sometimes considerable shelf time of a drug delivery device before the device reaches the user or patient. It needs to be ensured that the device including the electronic system still functions properly for the duration of its intended use.

The present disclosures presents various concepts which can be implemented in drug delivery devices or electronic systems thereof or therefore, e.g. for improving the power management in the devices. Some concepts rely on providing electrical power to certain units of the device only when needed or when it is very likely that the power will be needed. The device which has been discussed above, for example, energizes a motion sensing unit (the sensor system) of the device only when the injection button (as user interface member) is being pressed for performing a dose delivery (injection) operation. The encoder component or encoder ring, after the motion sensing unit has been energized, can be used to gather data on movements which are indicative for the dose which has been delivered during the delivery operation. From the measured movement data, it can be calculated, how much of the drug has actually been delivered. The amount of the actually delivered drug does not necessarily coincide with the dose which was previously set in a dose setting operation, e.g. when the user interrupts the delivery operation before it has been actually completed. Accordingly it is advantageous to measure movements occurring during the dose delivery operation which are correlated to the amount of drug which has been delivered already, e.g. to get insight on the current status or the progress of the delivery operation. The determined delivered dose may be communicated, preferably wirelessly to an external or remote device, e.g. a hand-held device such as a smartphone. In this way a dose log on the doses delivered by the user may be established, which may be accessed by the user easily.

The proposed concepts are suitable for a large variety of drug delivery devices comprising electronic systems or for electronic systems for such devices not only for the devices described further above. The device may be an injection device and/or a pen-type device. The device may be configured to receive or comprise a medicament container or cartridge. The container or cartridge may be filled with liquid drug to be delivered by the device. The device may be designed to deliver a plurality of doses of the drug. Consequently, the container or cartridge may comprise drug in amount sufficient for several doses to be delivered by the device. The device may be re-usable or disposable, where a re-usable device may be provided with a replacement medicament container or cartridge when the current container or cartridge is considered empty or needs to be replaced for different reasons. A disposable device may be a single use device which is disposed after the medicament container has been emptied. The device may be a device of a dial extension type, that is to say a device which increases in length during the dose setting operation, where the increase in length is proportional to the size of the set dose. During the associated dose delivery operation, the length of the device may be decreased again, e.g. until the device resumes its original length, i.e. the length it had before the dose setting operation has been commenced. Alternatively, the length of the device may be independent of the size of the set dose, e.g. constant or substantially constant during dose setting and/or dose delivery. The dose setting operation may involve a, preferably rotational, movement, of a dose setting member as user interface member, e.g. a knob, button or grip component (as discussed further above already). The dose delivery operation may involve a, preferably axial, movement of a dose delivery member as user interface member, e.g. a button such as the injection button discussed further above. As already discussed further above, the dose setting member and the dose delivery member may be formed by a single, e.g. unitary, component, where, preferably, different surfaces of the component are manipulated during the dose setting operation and the dose delivery operation or, alternatively, the dose setting member and the dose delivery member may be separate components/interface members or parts with relative movement being possible between these members, e.g. to switch the dose setting and drive mechanism between a dose setting configuration and a dose delivery configuration. There may be relative movement between these components either during dose setting or dose delivery or during both operations. During the dose setting operation a lateral or side surface, i.e. a radially facing surface, of the dose setting member may be gripped by the user, e.g. with the thumb and index finger. During the dose delivery operation an axially, e.g. proximally, facing surface of the dose delivery member may be touched by the user, e.g. with the thumb. During the dose delivery operation, an axial force may be transferred by the user to the dose delivery member in order to initiate and/or to continuously drive the dose delivery operation using a dose setting and drive mechanism of the device which aside, from the user interface member may comprise further members, such as a drive member and a piston rod, for example. The drive member may engage the piston rod. In one embodiment, the dose delivery member may be the drive member which engages the piston rod, e.g. threadedly. The device may be a device as disclosed, for example, in WO 2015/028439 A1 which is incorporated herein by reference in its entirety.

The device may be a needle-based device, i.e. the drug may be delivered into the body via a needle piercing the skin or may be needle-free. The device may be a device with a delivery assist, e.g. a spring-assisted or spring-driven device. In such devices, the dose delivery operation by the user is assisted or entirely driven by energy provided by an energy storage member such as a spring. The energy in the storage member may be increased during the dose setting operation by the user or the energy storage member may be provided with the entire energy required to empty the medicament container pre-stored in the member by the manufacturer. In the latter case, the user does not need to provide energy to increase the energy stored in the energy storage member such as during the dose setting operation.

Figure 20:
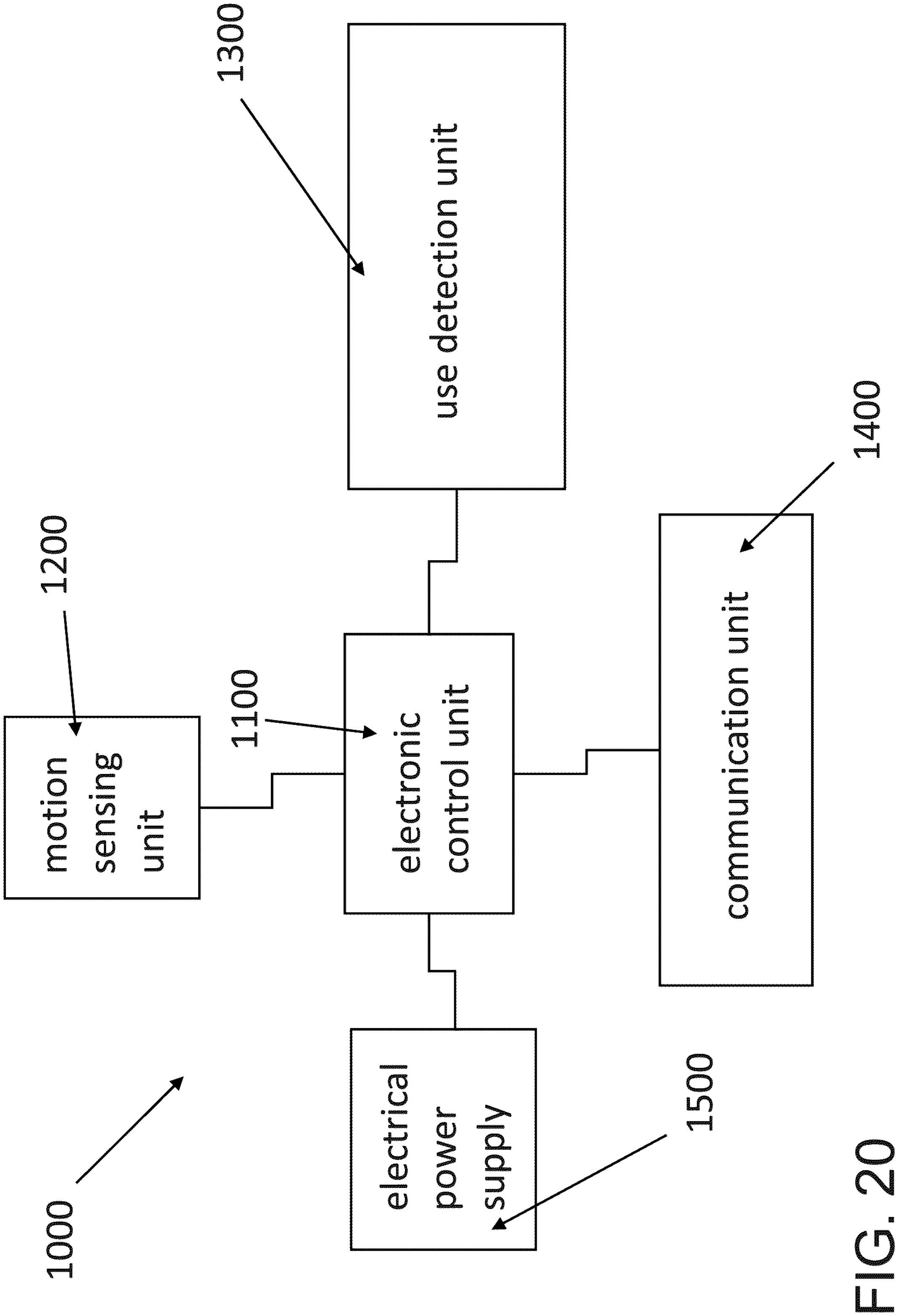
FIG. 20 illustrates schematically an embodiment of an electronic system for a drug delivery device.

FIG. 20 illustrates a general configuration of elements of an electronic system 1000 which can be used in a drug delivery device, for example one of the devices discussed further above or other devices.

The electronic system 1000 comprises an electronic control unit 1100. The control unit may comprise the controller 700 as discussed further above. Specifically, the control unit may comprise a processor arrangement 23 as discussed further above. Also, the control unit 1100 may comprise one, or a plurality of memory units, such as program memory 25 and main memory 24 discussed further above in conjunction with FIG. 7. The control unit 1100 is expediently designed to control operation of the electronic system 1000. The control unit 1100 may communicate via wired interfaces or wireless interfaces with further units of the electronic system 1000. It may transmit signals containing commands and/or data to the units and/or receive signals and/or data from the respective unit. The connections between the units and the electronic control unit are symbolized by the lines in FIG. 20. However, there also may be connections between the units which are not illustrated explicitly. The control unit may be arranged on a conductor carrier, e.g. a (printed) circuit board. The other unit(s) of the electronic system may comprise one or more components which are arranged on the conductor carrier as well.

Electronic system 1000 may further comprise a motion sensing unit 1200. The motion sensing unit 1200 may comprise one or a plurality of sensors, e.g. the sensors 215*a* and 215*b* described further above. In case optoelectronic sensors which detect electromagnetic radiation, such as IR sensors, are used, the motion sensing unit may additionally comprise a radiation emitter which emits the radiation to be detected by the sensor. However, it should be noted that other sensor systems, e.g. magnetic sensors could be employed as well. A motion sensing unit which has an electrically operated sensor and an electrically operated source for stimulating the sensor—such as a radiation emitter and an associated sensor—the power consumption may be particularly high and, hence, power management may have particular impact. Each sensor may have an associated radiation emitter. Motion sensing unit 1200 may be designed to detect and preferably measure relative movement of two movable members of a dose setting and drive mechanism of or for the drug delivery device during a dose setting operation and/or during a dose dispensing operation. For example, the motion sensing unit may measure or detect relative rotational movement of two movable members of the dose setting and drive mechanism with respect to one another. Based on movement data received from or calculated from the signals of the unit 1200, the control unit may calculate the dose data.

Electronic system 1000 may further comprise a use detection unit 1300. The use detection unit may be associated with the user interface member or members such that manipulation of the member for setting and/or delivering a dose thereof may be detected. When the manipulation is detected, the use detection unit generates or triggers generation of a use signal. The use signal can be transmitted to the electronic control unit 1100. The electronic control unit may, in response to the signal, issue a command or signal to one of, an arbitrarily selected plurality of, or all of the other electrically operated units of the system. For example, the control unit may cause that the respective unit is switched from a first state, e.g. a sleeping state or idle state with a lower power consumption or an off state with no power consumption, to a second state with an increased power consumption. The switching may be done by an according switching command or signal issued by the electronic control unit to the respective unit. In response to the use signal all units may be switched to the second state or just selected units. If only selected units are switched to the second state with higher power consumption, it is expedient that these units are intended to be used during the operation which is intended to be commenced by the user or which has been commenced.

For example, typical times required to switch the motion sensing unit to the second state are between 2.5 ms and 3.2 ms, e.g. after generation of the use signal or actuation of the user interface member to initiate the operation of the system, e.g. the dose delivery operation.

The electronic system 1000 may further comprise a communication unit 1400, e.g. an RF, WiFi and/or Bluetooth unit. The communication unit may be provided as a communication interface between the system or the drug delivery device and the exterior, such as other electronic devices, e.g. mobile phones, personal computers, laptops and so on. For example, dose data may be transmitted by the communication unit to the external device. The dose data may be used for a dose log or dose history established in the external device. The communication unit may be provided for wireless or wired communication.

Electronic system 1000 may further comprise an electrical power supply 1500, such as a rechargeable or non-rechargeable battery. The power supply 1500 may provide electrical power to the respective units of the electronic system.

When the system is in the first state, e.g. with neither the motion sensing unit being active nor the communication unit, the current consumption may be 200 nA. When (only) the motion sensing unit is active, the power consumption may be 0.85 mA. When the communication unit is active, e.g. in addition to the motion sensing unit or only the communication unit, the power consumption may be 1.85 mA.

Although not explicitly depicted, the electronic system may comprise a, preferably permanent and/or non-volatile, storage or memory unit, which may store data related to the operation of the drug delivery device such as dose history data, for example.

In one embodiment, the electronic control unit 1100 may be configured to reduce the power consumption of the respective unit, i.e. to switch the unit back to the first state. This is suitable, for example if an event which is relevant for that unit, e.g. a motion sensing event for the motion sensing unit, has not occurred in a predetermined time interval after the unit has been switched from the first state into the second state and/or after the use signal has been generated. The monitoring of the time interval may be achieved by a timer unit which is operatively connected to the electronic control unit (not explicitly shown). In case, after the use signal, there is no signal generated by the motion sensing unit within the predetermined time interval, the entire system may be switched again to the first state. This time interval may be greater than or equal to one of the following values 0.2 s, 0.5 s, 1 s, 5 s, 10 s, 15 s, 20 s, 25 s, 30 s.

It goes without saying that the electronic system 1000 may comprise further electronic units other than the ones shown such as other sensing units, which sense or detect different quantities or events than the relative movements which the motion sensing unit detects.

The respective unit may be integrated into a user interface member 1600, e.g. a dose setting and/or delivery button (e.g. knob 12 of the device discussed previously) of the electronic system which is discussed in further details below in conjunction with the embodiment depicted in FIGS. 31A and 31B in more detail but is preferably present in any one of the embodiments discussed below.

The use detection unit 1300, when it is operational to generate the use signal, e.g. the setting signal and/or the delivery signal, expediently has a lower power consumption than the motion sensing unit 1200 when it is active.

When investigating the operation of the trigger switch arrangement with switch 800 which has been discussed further above, it has been noticed that designing such a trigger switch arrangement is challenging, e.g. as an axial movement is used to trigger the switch. For example, it needs to be ensured that the switch is triggered before the delivery operation is commenced, e.g. before a clutch is disengaged. Furthermore, the switch may be subject to considerable axial displacement as the clutch needs to be disengaged by relative axial movement after the switch has been triggered, which may put considerable load onto the switch. These considerations render the design of an axial trigger switch pretty complex and, potentially, unreliable.

In the following, a couple of embodiments are discussed which may address drawbacks of existing systems. Also, it may be desirable to provide further embodiments of systems which are configured to wake up further electronic components of the systems (only) when the operation of the respective component is needed. In general, systems which have a configuration to allow one or more further electronic components to be woken from a low power state or sleeping state will be discussed below.

Figure 21:
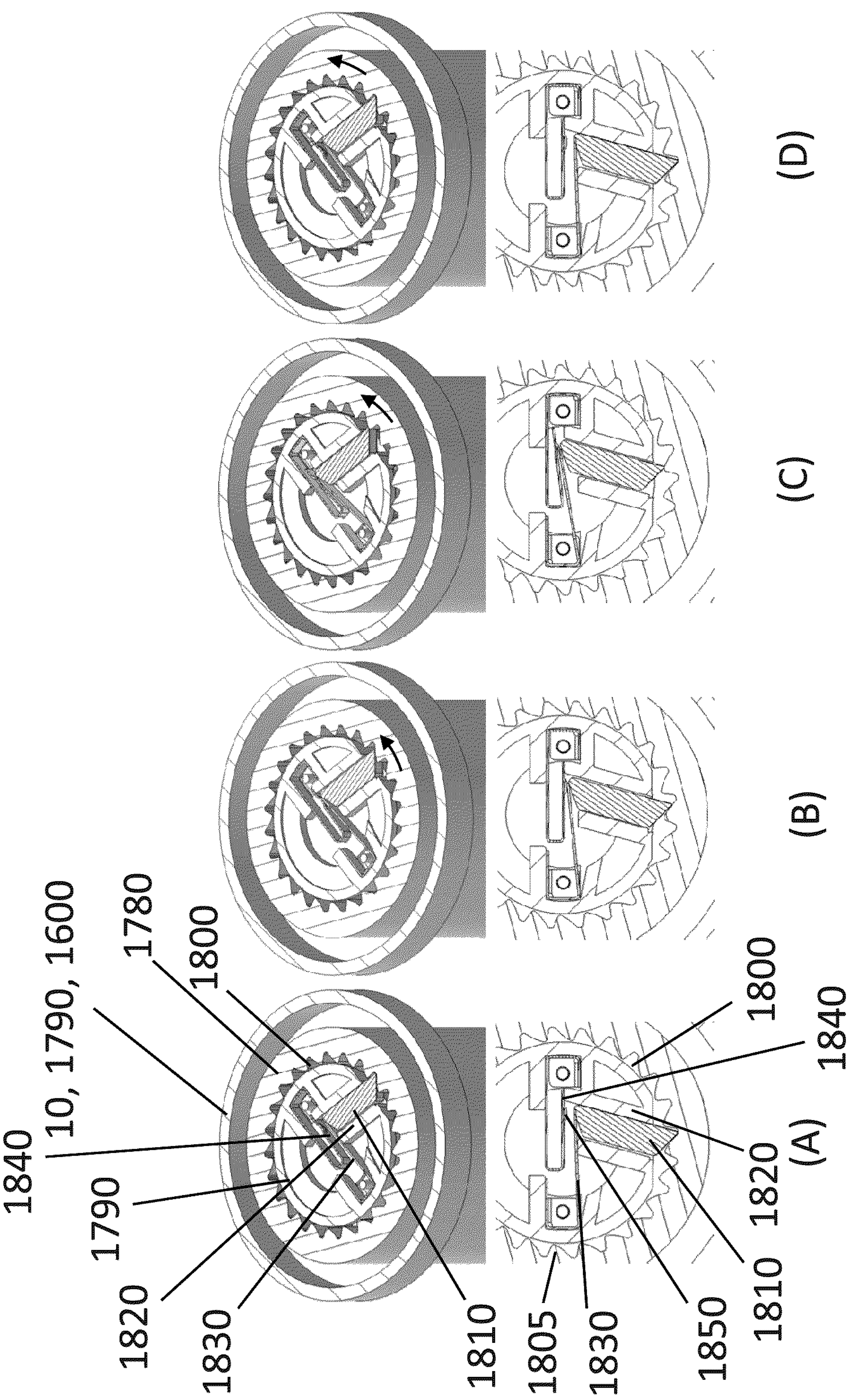
FIG. 21 illustrates an embodiment of the electronic system and particularly its use detection unit to generate the use signal.

FIG. 21 illustrates an embodiment of an electronic system on the basis of four different representations A through D during operation of the device utilizing the electronic system. In this embodiment, when the use signal is generated it is ascertained that the respective operation—in this example the dose delivery operation but likewise possible for the dose setting operation—has already been initiated or commenced. This is advantageous over triggering the wake-up process for the motion sensing unit via axial movement of the user interface member, e.g. an injection button. The axial trigger movement of the user interface member could happen inadvertently e.g. by parts in a handbag hitting and moving the button while the user is walking around, whereas the relative movement which is required for actually performing the desired operation is less likely to occur inadvertently. The present embodiment uses a relative movement of two members occurring during the dose delivery operation to switch the electronic system from the first state of lower power consumption to the second state of higher power consumption where, for example, the motion sensing unit and/or the communication unit are powered up. Integrating the switching process into the dose delivery operation has the advantage that, in case the currently dispensed dose should be monitored via the motion sensing unit, the activation of the motion sensing unit may occur immediately when it is needed—actually only after when the operation it should monitor has been commenced already. It should be appreciated that, of course, similar switching operations or the same switching operations can also be performed during the dose setting operation. However, the following description focuses on the dose delivery operation. FIG. 21, in the upper portion, shows a perspective view on members of the electronic system relevant in connection with the disclosed concept and the lower portion shows a top view onto these members. The different representations A through D illustrate different relative positions of the members during the dose delivery operation.

Representation A illustrates the situation when a dose has been set and before the dose delivery operation is commenced. Depicted are schematical representations of a housing 10, a first member 1780 and a second member 1790. Instead of a portion of the housing 10, the outer portion may also be a portion of the first member and/or a portion of the user interface member 1600 as will become apparent from a brief look on the representation in FIGS. 31A and 31B. The first member and the second member are part of a dose setting and drive mechanism of or for the drug delivery device. For example, the first member 1780 may be the dial sleeve or number sleeve or a member axially and/or rotationally locked thereto and the second member 1790 may be the drive sleeve or the user interface member, e.g. a dose and/or injection button. At least a section of the second member 1790 may be received in the first member 1780.

For dose delivery, the first member 1780 moves, e.g. rotates, relative to the second member 1790. The second member may be directly or indirectly engaged with a piston rod to drive the dose delivery operation. During dose setting, the first member 1780 and the second member 1790 may co-rotate relative to the housing 10. Thus, these members may be rotationally locked relative to one another such as by a clutch interface which is established during dose setting (e.g. via mating teeth on the two members, not shown). During and/or for dose delivery, the clutch interface may be released. The length of the device may be increased by an amount which is proportional to the size of the set dose by the first member and/or the second member protruding from the housing during the dose setting procedure. However, the disclosed concept would also work without such a dial extension during dose setting. During dose setting, a dose setting member, e.g. the user interface member 1600 which may be integrated into the second member may be rotated relative to the housing 10 in an incremented manner, e.g. in whole-number multiples of a unit setting increment. This may be achieved via a dose setting interface, e.g. a ratchet interface (not explicitly shown), which is pitched in accordance with the unit setting increment. Such an interface may be formed between the first member 1780 and the housing or another member which is stationary during the dose setting procedure and a member movable, e.g. rotatable, relative to that member stationary during setting. The dose setting interface may define stable positions of the respective member with respect to the housing which are separated in the angular direction by one unit setting increment. For example, one unit setting increment may correspond to a rotation angle of 15°. Thus, two stable rotational positions may be separated by 15° in the angular direction.

In order to switch the electronic system from the first state into the second state, this concept utilizes a use signal generation interface to generate a use signal before the first member and the second member have rotated relative to one another by one unit increment, which will be discussed further below. The use signal generation interface is also an incremented interface and, preferably, is incremented or pitched in the same manner as the dose setting interface or may have even finer pitch or smaller increments. In the depicted embodiment, the first member 1780 is provided with circumferentially disposed ratchet pockets 1800. Two adjacent ratchet pockets are separated by a ratchet tooth 1805. The respective teeth 1805 are circumferentially disposed. In the depicted embodiment, the ratchet pockets 1800 define 24 stable positions distributed over 360°, i.e. two stable positions are separated by an angle 15°. The respective ratchet pocket or the teeth 1805 defining the pockets may be radially oriented, i.e. the teeth may have a radial free end. The teeth may point inwardly. Alternatively to the first member comprising the ratchet, a use signal generation interface member 1880 may be provided with the ratchet, which is at least rotationally locked to the first member 1780, which may be the dial sleeve or number sleeve, for example. In the depicted embodiment, two adjacent ratchet pockets are delimited by differently sloped surfaces, a steep surface and the less steep surface. This ratchet interface is provided to define a unidirectional interface where relative rotation between the two components is only possible in one rotational direction. Thus, the interface can be used to block rotation in the other direction which may increase the safety of the device employing the system. In the present configuration, rotation of the first member 1780 with respect to the second member 1790 in the counterclockwise direction is allowed. Expediently, the allowed rotation is the one which occurs during the dose delivery operation. Thus, the clutch interface has to be released before the system is switched into the second state and also a part of the dose delivery operation has to be performed already.

Moreover the system comprises a switching feature 1810, e.g. a pin-like component. The switching feature 1810 is movable, e.g. radially, relative to the ratchet pockets 1800 in response to rotation of the first member 1780 relative to the second member 1790. The switching feature expediently shuttles between two different positions. In a first position, e.g. a radially outward position, the feature engages the ratchet pocket 1800 and in a second position, e.g. an inward position, it engages an end surface of the ratchet tooth. If the first member 1780 is rotated relative to the second member 1790, on account of the sloped surface delimiting the ratchet pocket in the angular direction which is opposite to the rotational direction, the switching feature 1810 is inwardly displaced, e.g. radially inwardly, from the first position to the second position. The switching feature 1810 may be guided such that, in response to rotation of the first member 1780 it moves only linearly, e.g. in the radial direction or predominantly in the radial direction. For this purpose, a guide slot 1820, e.g. a linear slot, is provided in the second member 1790. A free end of the switching feature may have a shape complementing the ratchet pockets. The switching feature 1810 may be tightly received in the respective ratchet pocket 1800. The switching feature 1810 may be rotationally locked to the second member 1790. The switching feature may be radially oriented or be arranged such that it defines an angle with the radial direction. The switching feature may be electrically insulating, e.g. of plastic.

The system further comprises a first electrical contact feature 1830, e.g. an elastically displaceable feature. The feature 1830 may be a metal feature and/or a contact strip. The system further comprises a second electrical contact feature 1840, e.g. an elastically displaceable feature. The feature 1840 may be a metal feature and/or a contact strip. The respective contact feature may be fixed to the second member 1790. The respective feature may have a free end and/or a portion which is displaceable relative to the portion where the respective feature is fixed to the second member 1790. The first contact feature 1813 is arranged to be moved towards the second feature 1840 when the switching feature 1810 is displaced inwardly.

In the situation depicted in representation A the first electrical contact feature 1810 may urge the switching feature 1810 outwardly to maintain the switching feature in engagement with that ratchet pocket 1800 which it is currently engaged with. Thus, in the representation A, the switching feature 1810 and the first electrical contact feature abut. The contact features 1840 and 1830, however, are separated and not conductively connected.

When, starting from the situation in representation A, the dose dispensing operation is commenced which involves relative rotation of the first member with respect to the second member, the switching feature 1810 will be displaced inwardly. The switching feature 8010 carries with it the first electrical contact feature 1830 and moves it towards a portion of the second electrical contact feature 1840 until the contract features are in mechanical and electrical contact with one another as depicted in representation B. By way of this contact, a use signal may be generated which can be used to trigger the switching of the electronic system into the second state of higher power consumption as has been discussed above already. For example both contact features may be conductively connected to the power supply 1500 and, current as the use signal can only flow if the contact features are conductively connected. The use signal is preferably generated when the first member has been rotated relative to the second member by less than one unit increment as depicted in representation B. Preferably, a piston rod of the dose setting and drive mechanism has been displaced already to begin dispense of a first unit increment of drug from a container of the device before the use signal has been generated, e.g. drive by user force transferred to the piston rod from the user via the second member 1790. The portions of the first and second contact feature 1830 and 1840 which abut are displaced together by the switching feature 1810 as is depicted in representation C. This ensures that the use signal is generated in all tolerance conditions. When the rotation is continued, the switching feature 1810 is again allowed to move outwardly into engagement with the next ratchet pocket 1800. This movement is driven by the resilient force provided by the first contact feature 1830. Thus, after the rotation has been completed by one unit increment (signal generation increment), the switching feature 1810 again rests in a ratchet pocket. Also, the second contact feature 1840 returns to its initial position such that, after the rotation by one unit increment has been completed, the system is in the situation depicted in representation D which, aside from the relative rotation by one unit increment, corresponds to the situation in representation A. When dose delivery continues, the features are brought into contact again during the next increment, where a signal is generated again.

Accordingly, the use signal may be generated in an incremented fashion depending on the relative rotation between the two members 1780 and 1790. Also, it is ensured that the use signal has been generated before the rotation by one unit increment has been completed. Thus, if the motion sensing unit 1200 has been switched to a sensing state where the components of the motion sensing units, such as LED(s) and sensor(s), are supplied with electrical power and detects the relative rotation between the first and second members during the further course of the dose delivery operation, the offset by one unit increment may be taken into account, e.g. by adding the angle corresponding to one unit increment of the use signal generation interface to the result of the calculation of a rotation angle derived from the signal of the motion sensing unit. It is advantageous that the dose setting interface and the use signal generation interface are incremented in the same manner as has already been discussed above. However, different increments are also possible where the use signal generation interface is preferably finer pitched, i.e. with smaller increments in the angular direction, than the dose setting interface. It is, however, also possible to have a coarser pitch in the increments of the use signal generation interface than in the ones of the dose setting interface.

In the portions, where the first electrical contact feature and the second electrical contact feature are designed to abut to trigger the generation of the use signal, a protrusion or bulge may be arranged, which points from one of the portions towards the other one of the portions. In the depicted embodiment such a protrusion 1850 is provided on the second electrical contact feature 1840. This may also assist to guarantee a use signal even in extreme tolerance condition. However, such a protrusion need not be present. Alternatively, both contact features could be provided with such a protrusion 1850. Moreover, it is also conceivable to use a separate biasing member to drive the respective movement of the switching feature and/or any movement of the respective contact feature, wherein the biasing member is biased while the contact features are in abutment and/or moved together.

Having radially oriented ratchet features (pockets and teeth) and the radially/transversely oriented switching feature facilitates an axial relative movement between the first member and the second member which may be necessary to release/establish a clutch interface and/or in order to switch between the dose setting operation and the dose delivery operation. However, there may also be systems which do not involve such a switching of a clutch interface. For allowing the relative axial movement, the ratchet pockets may have an axial extension which is sufficient to permit this movement. That is to say, the switching feature may be axially guided within the ratchet pocket by a distance which corresponds to the distance which is required to switch the state of the clutch interface, e.g. from a coupled or established state to an uncoupled or released state or vice versa.

It is advantageous, if the force required to operate the switch which is established by the first electrical contact feature and the second electrical contact feature is as low as possible in order to avoid that the user has to exert too much force during the dose delivery operation.

In the depicted situation, use signals are generated throughout the entire dose delivery operation every time the switching feature 1810 is displaced inwardly when it changes position from one ratchet pocket into the next ratchet pocket.

In one embodiment the first member 1780 or the use signal generation interface member 1880 may be axially coupled, e.g. locked relative to the second member 1790, e.g. the dose button and/or drive sleeve. This configuration avoids relative axial movement of the member with the ratchet features (1800, 1805) relative to the member the rotation of which should be monitored and/or the switching feature 1810. In this case, the ratchet may be axially displaced relative to the member the rotation of which should be monitored. The relative axial position of switching feature 1810 and ratchet may be constant. Alternatively, the switching feature is axially displaced relative to the ratchet when the dose delivery operation is being initiated or commenced.

Apart from generating one or more use signals, the disclosed configuration, may be used in order to generate an audible and/or tactile feedback during the dispensing operation and/or to prevent relative rotation between the first and second members in an undesired direction.

In the present configuration, the generation of the use signal may be triggered without a direct contact from a user, i.e. a switch which does not have to be mechanically contacted by the user. Moreover, the event which causes the generation of the use signal is integrated into the regular operation procedure of the drug delivery device, particularly into the dose delivery operation after the user interface member/button has been moved into the position required for this operation and when the user interface member has reached that position, the relative movement between first and second member has been commenced. A separate user action is not necessary in order to switch the electronic system to the second state. Moreover the use signal increments can be matched to the dose unit increments which is advantageous, as the switching of the state of the electronic system can be precisely tuned to the dose unit increments.

In an alternative design, the switching feature may be pivotally mounted to the first member such that rotation of the first member causes a pivoting movement in a plane perpendicular to the rotation axis.

Figure 22:
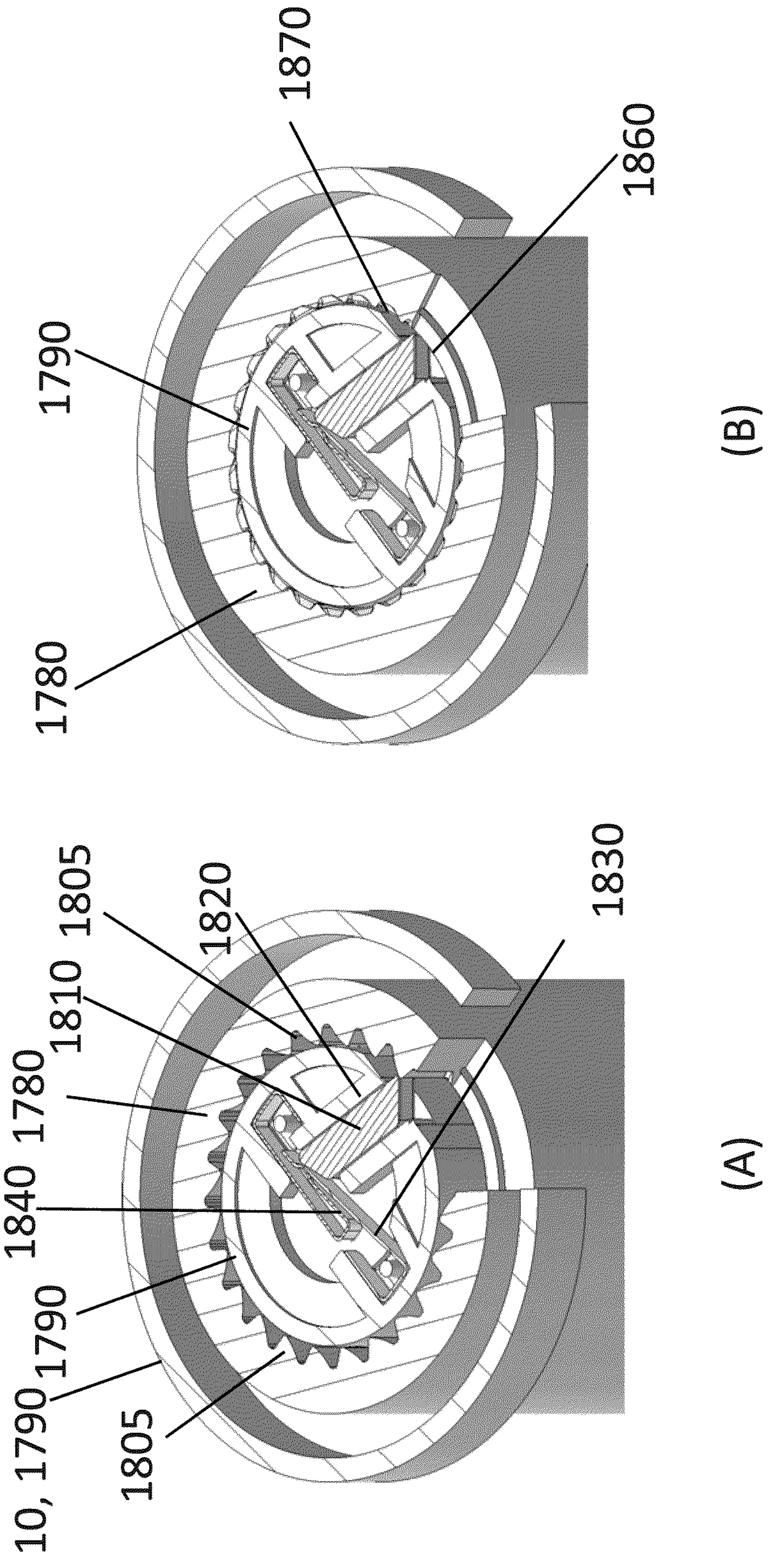
FIG. 22 illustrates another embodiment of the electronic system and particularly its use detection unit to generate the use signal.

FIG. 22 illustrates another embodiment of an electronic system on the basis of two representations A and B. As will be easily acknowledged, this embodiment is very similar to the one discussed in conjunction with FIG. 21. However, in this embodiment, the situation is a little different as regards engagement of the switching feature 1810 with the ratchet, which is defined by the ratchet pockets 1800 which are separated by ratchet teeth 1805. As has been discussed further above, in conjunction with the embodiment in FIG. 21, the switching feature 1810 may be engaged with the ratchet pockets and/or the ratchet teeth in a first axial relative position of the first member 1780 and the second member 1790 and in a second axial position of that movable members. The first and the second axial position may be the two extreme positions the first and second member may have relative to one another. For example, starting from an initial position the second member 1790 may be moved axially, e.g. distally, relative to the first member 1780 until it has reached an end position. Therefore, in FIG. 21, in the end position, the switching feature 1810 is also engaged with the ratchet teeth and/or the ratchet pockets. As there is relative rotational movement between the first member 1780 and the second member 1790 in the dose delivery operation, force or torque needs to be provided to continuously increment the ratchet, e.g. by the user when the device is user driven. However, after the initial use signal generation, a further use signal may not be necessary anymore as the electronic system has been switched to the state of higher power consumption already such that the dose recording via the dose recording or motion sensing unit can be performed.

Consequently, it may be advantageous to reduce the force. Therefore, in this embodiment shown in FIG. 22, in the first relative axial position of the first member 1780 and the second member 1790, the switching feature 1810 engages the ratchet and relative rotation between the first and the second member results in the switching feature being displaced to generate the use signal. However, when the first and the second members 1780 and 1790 have reached the second relative axial position, the switching feature 1810 has disengaged the ratchet. The use signal is still generated by the relative rotation of the first member and the second member. The first relative axial position may be the regular position of the two members, e.g. maintained by a biasing member such as the clutch spring. When in the second relative position a counterforce, e.g. by the user, is removed the first relative position may be established again by the spring.

Representation A illustrates an intermediate state during the relative movement between the first axial position and the second axial position of the members 1780, 1790 when the generation of the use signal has already been triggered (indicated by the abutting contact features 1830 and 1840). Specifically, the state in representation A in FIG. 22 corresponds to the state in representation C of FIG. 21. However, at the end of the relative axial movement the switching feature 1810 has disengaged the ratchet. For example, it may be axially offset from the ratchet, e.g. distally offset. This situation is shown in representation B of FIG. 22. Here, the second relative axial position between the first member 1780 and the second member 1790 is illustrated. As is immediately apparent, the switching feature 1810 now engages, in particular radially, a surface 1860. The surface may be smooth, in particular as compared to that area where the ratchet pockets 1800 and the ratchet teeth 1805 are disposed. The surface 1860 may be cylindrical. Axially between the surface 1860 and the respective ratchet pockets 1800 or ratchet teeth 1805 a ramp 1870 is arranged. The ramp may be defined in an end section of the respective ratchet pocket 1800 which engages the switching feature 1810 during the relative movement of the first member and the second member from the first axial position into the second axial position. The ramp may be inclined in the axial direction, e.g. inwardly, when seen along the movement direction of the switching feature 1810 relative to the ratchet pocket 1800 to disengage the switching feature 1810 from the pocket. When engaged by the switching feature 1810, the ramp may guide the switching feature 1810 in the radially inward direction until the ratchet pocket 1800 is disengaged. Then the switching feature 1810 may engage the surface 1860. The surface 1860 may react the residual force provided by the elastically deformed first and/or second contact feature(s) 1830, 1840. Accordingly, in the second relative axial position between the first and second members, the contacts may be continuously closed and a use signal may be generated.

It is not necessary that the contact features 1830 and 1840 engage one another in the second relative axial position of the first and second members. This can be achieved by widening the interior of the system, e.g. of the first member 1780, in the region where the switching feature 1810 is disposed in the second relative axial position of the first and second members. This is not explicitly illustrated. In this case, a ramp which is inclined outwardly when seen along the movement direction, may be axially disposed between the ratchet pockets 1800 and the switching feature 1810. This ramp may serve to reengage the switching feature with the ratchet pockets 1800 when the first relative position between the first and second member is reestablished after the delivery operation has been completed. Here, the radial width in that portion of the first member, where the switching feature is axially arranged in the second relative axial position of the first member and the second member, is preferably greater than the radial width defined between the free ends of the ratchet teeth.

In this embodiment, the axial extension of the ratchet pockets and/or teeth may be greater than the distance required to release the clutch interface for rotationally decoupling the first member and the second member from each other. The axial extension of the ratchet pockets is expediently chosen such that it permits triggering of the use signal in even extreme tolerance conditions. The user interface member/button may be movable in the distal direction from an initial position to a dose delivery position. The distance may be greater than required to release the clutch interface.

In this embodiment, in case the contact features are in contact in the second relative axial position (as in representation B of FIG. 22), the user interface member could be used to generate the use signal without relative rotation being required as the contact is closed in the second position. Therefore, in terms of power drainage, the option where the contact is not closed in the second relative axial position may be advantageous.

Figure 23:
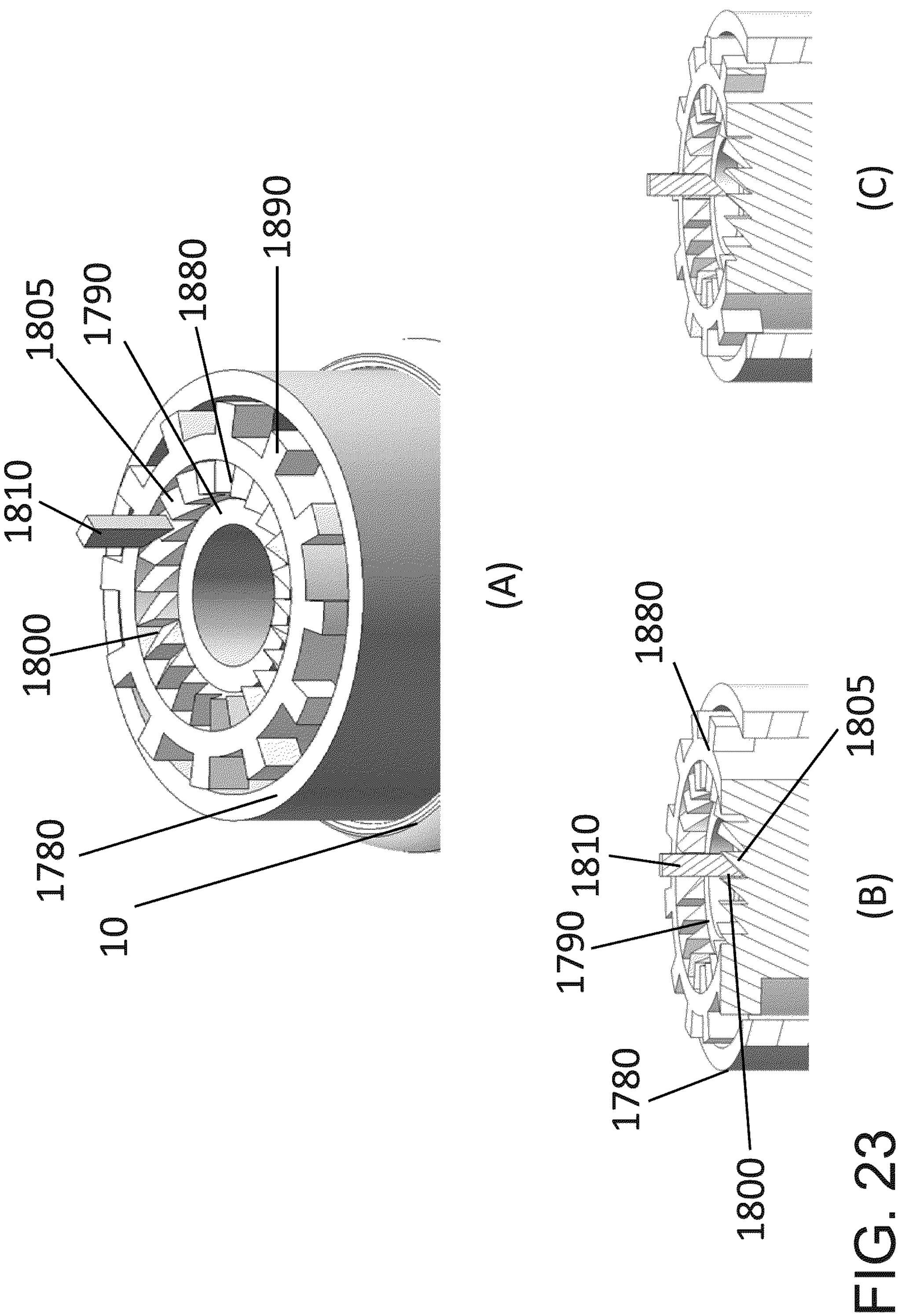
FIG. 23 illustrates another embodiment of the electronic system and particularly its use detection unit to generate the use signal.

FIG. 23 illustrates yet another embodiment of an electronic system on the basis of three different representations A through C. The general setting of the system is very similar to the systems disclosed further above in conjunction with FIGS. 21 and 22. Therefore, the following discussion will focus on the differences.

As in the previous embodiments, the first member 1780, e.g. the number sleeve, the dial sleeve and/or a component rotationally and/or axially attached thereto, and the second member 1790, e.g. a drive sleeve or a dose and/or injection button, are provided. The housing 10 is also depicted. The first member and the second member may be rotationally locked to one another during the dose setting operation but there is relative rotation during the dose delivery operation. For example, the first member 1780 may rotate relative to the second member 1790 and relative to the housing 10 during dose delivery. The second member 1790 may be rotationally locked to the housing during dose delivery. The angle of rotation of the first member relative to the second member may, as in the embodiments which have been discussed already, be indicative for the size of the dose which has been dispensed already.

In this embodiment, again, relative rotation between the first and second members 1780, 1790 is used to trigger the use signal generation. As in the embodiments described further above, for this purpose, the switching feature 1810 is provided. The switching feature 1810 in general is configured in the same way as discussed previously. However, its orientation is different, as it is axially oriented as can be seen in representation A which presents an oblique view onto the described elements of the system which, of course, may have additional elements. The switching feature 1810 moves axially in order to generate the use signal by triggering a sensor or switch which, contrary to the embodiments discussed previously is not explicitly illustrated. The sensor or switch could be implemented via electrically contacting features or via a force sensor or pressure sensor which is mechanically contacted by the switching feature in order to trigger the generation of the use signal. The use signal may be fed to the electronic control unit and may be used to trigger the switching of the system into the second state by the control unit.

The switching feature 1810 is again operatively coupled or engaged with ratchet pockets 1800 and/or ratchet teeth 1805. The ratchet teeth and pockets together define a ratchet. Contrary to the previous embodiments the ratchet pockets 1800 and/or the ratchet teeth are axially oriented. For example, free ends of the ratchet teeth 1805 may be oriented in the axial direction such as in the proximal direction. The ratchet teeth may have a helical configuration. That is to say an inclined side face of a tooth may extend helically when viewed in top view along the rotation axis, e.g. in the distal direction. When there is relative rotation between the ratchet teeth 1805 and the switching feature 1810, the switching feature may be displaced axially relative to the ratchet pocket and/or the ratchet teeth, e.g. away from the teeth and/or outwardly relative to the ratchet pockets. This axial movement may be used to trigger the use signal.

In the present embodiment, contrary to the preceding embodiments, a (separate) signal generation interface member 1880 is explicitly illustrated. Such a member may be provided in the preceding embodiments as well or may be dispensed with. The signal generation interface member 1880 or at least a portion thereof may be arranged radially or axially between the first member 1780 and the second member 1790. The ratchet may be provided on the signal generation interface member 1880. The signal generation interface member 1880 may be mechanically coupled to the first member 1780 and/or the second member 1790. For example, the signal generation interface member 1880 may be rotationally locked to that member which rotates relative to the housing and relative to the other member. For example, it may be rotationally locked to the first member 1780. The signal generation interface member may be axially locked or coupled to the other member which, preferably does not rotate relative to the housing 10, e.g. during dose delivery. For example, the member 1880 may be axially coupled to the second member 1790. The one of the first and the second member to which the signal generation interface member 1880, which may have a ring-like configuration, is axially secured, locked or coupled may be the member which carries the sensor or switch which is triggered by the movement of the switching feature 1810. When axially coupled to one of the members, e.g. the second member 1790, the signal generation interface member 1880 may follow axial movement of that member, especially in the distal direction and/or in the proximal direction.

When the signal generation interface member 1880 is rotationally locked to the other one of the members, e.g. the first member 1780, it may rotate together with that member relative to the housing and/or relative to the other member, e.g. relative to the second member 1790.

In the depicted embodiment, the signal generation interface member 1880 is preferably rotationally locked to the first member 1780 and may be axially locked to the second member 1790. Accordingly, when a clutch interface between the first member and the second member is released, e.g. by displacing the second member 1790 axially, e.g. distally, relative to the first member 1780, the rotational locking of member 1880 to the first member 1780 may be maintained and the signal generation interface member is moved together with the second member relative to the first member in the axial direction. The rotational locking may be effected by splines which provide a rotational lock between interface member 1880 and first member 1780 (not explicitly illustrated). The axial lock may be effected by a circumferential groove in the second member 1790.

The first member 1780 or the signal generation interface member 1880 may be provided with encoder surfaces or detection regions 1890 for the motion sensing unit such as the reflecting surfaces or regions **70*a* which have been described previously. The regions between the detection regions may be non-reflective regions 70*b*. The detection regions 1890 in the depicted embodiment are formed by protrusions protruding radially outwards where other configurations are possible. The regions are disposed circumferentially, preferably evenly, and/or aligned axially, i.e. arranged at the same axial position, where the axis is expediently the longitudinal axis of the system or the rotation axis of the first member 1780 relative to the housing 10. In other words, the regions 1890 may be evenly distributed. All regions 1890** may have the same configuration e.g. angular width and/or shape.

Representations B and C again show different stages during the relative movement of the first member 1780 relative to the second member 1790. As will be easily acknowledged, when the first member 1780 rotates, particularly in the clockwise direction, the switching feature 1810 will be displaced axially out of the ratchet pocket 1800 it currently resides in representation B on account of the interaction with the inclined side surface of the ratchet tooth 1805 until it disengages the ratchet pocket 1800 (see representation C). As rotation continues, the switching feature 1810 reengages the subsequent ratchet pocket 1800, e.g. on account of a biasing member and/or an elastically deformable contact feature (not explicitly shown), which biases the switching feature into engagement with the ratchet pockets 1800, e.g. by a biasing member which provides an axially, e.g. distally, directed force onto the switching feature 1810. In the situation in representation C the use signal is generated, e.g. by the feature 1810 triggering a switch such as a micro switch. Preferably, the operating force of the switch is small to keep the total increase in force required to drive system at a reasonable level. When from representation C the rotation is continued, the subsequent ratchet pocket is engaged by the switching feature.

Figure 24:
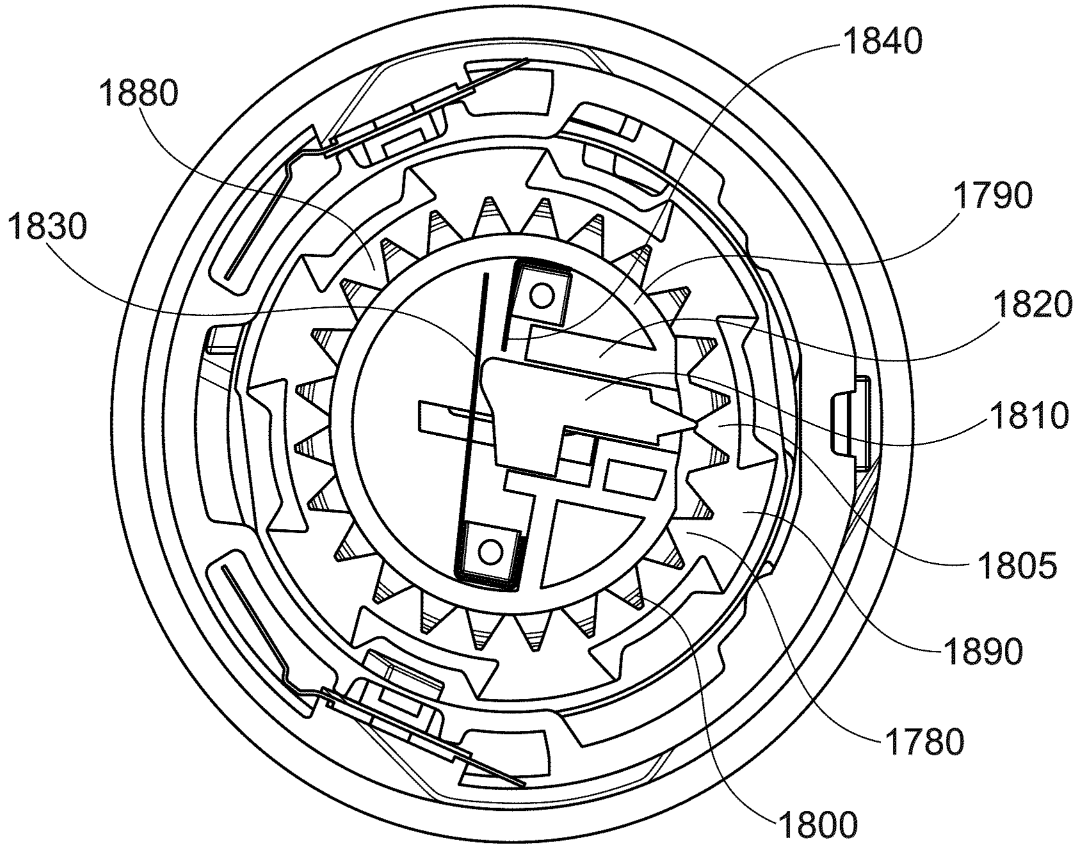
FIG. 24 illustrates another embodiment of the electronic system and particularly its use detection unit to generate the use signal.

FIG. 24 illustrates another embodiment of an electronic system. FIG. 24 represents a sectional view which, again shows the first member 1780 and the second member 1790 relative to which the first member rotates during dose delivery. Essentially, this embodiment corresponds to the previous embodiments, which is why the description in this respect applies as well to this embodiment as will be readily apparent for one of skill in the art. Consequently, the following description focuses on the differences.

The first member 1780, again, may be the use signal generation interface member 1880 with the ratchet with the ratchet pockets and the ratchet teeth 1800/1805 or another member to which the use signal generation interface member 1880 is connected, preferably rotationally locked. A limited relative axial movement between the use signal generation interface member 1880 and the first member may be allowed, if they are separate components. Alternatively or additionally, the use signal generation interface member 1880 may be axially locked to the second member 1790. A switching feature 1810 is, again, movably retained in the second member 1790. Switching feature 1810 is linearly guided, e.g. transversely and/or radially, relative to the rotation axis which, in the present embodiment, is perpendicular to the plane which is represented in the sectional view shown. The guide slot 1820 may receive the switching feature to guide linear movement of the switching feature.

FIG. 24 illustrates the situation when the first member 1780 and the second member 1790 co-rotate, e.g. because of a clutch coupling between the first member 1790 and the second member such as during dose setting. In this situation, the switching feature 1810 maintains a distance between contact features 1830 and 1840. Particularly, contact feature 1830 may be in the situation depicted in FIG. 24, elastically displaced or deformed such that the switching feature 1810 is biased towards the ratchet tooth 1805, in the depicted situation radially outwards. A radial end face, e.g. radially outward end face of the switching feature abuts a radial end face of a ratchet tooth 1805. The end face of the tooth may be flat. When relative rotation between the first member 1780 and the second member 1790 is allowed, the bias of contact feature 1830 moves the switching feature 1810 radially and closes the electrical connection with contact feature 1840. As rotation of member 1780 continues, the switching feature 1810 again displaces the contact feature 1830 away from the contact feature 1840. In this way, use signals are generated during dose delivery incremented fashion determined by the pitch of the teeth 1805.

As compared to the previously discussed embodiments, this embodiment has the advantage that the switching feature 1810 does not have to displace the contact features 1830 and 1840 into contact with one another, preferably with a small displacement of both of the contact features together in order to accommodate for tolerances. Rather, the switching feature 1810 is used to keep the contact features apart during dose setting. Also, only one of the contact features 1830 and 1840 has to be displaced during dose dispense, e.g. to open the electrical contact again, and the according force has to be provided, e.g. by the user.

The teeth 1805 may be configured symmetrically in this embodiment, particularly with respect to an axis oriented radially. As, during dose setting, the switching feature does not engage the ratchet pockets 1800, there is no option that this feature could be used to provide a resistance during dose setting. Likewise, in the dose dispensing configuration, when the first member and the second member are rotatable relative to one another, the interface between the feature 1810 and the ratchet cannot provide any significant resistance against decreasing the set dose which the other embodiments with unidirectional couplings may provide.

The symmetric configuration of the teeth facilitates a re-engagement of the radial end face of the switching feature 1810 with a radial end face of the teeth after the dose dispensing operation has been completed. The side faces of the teeth may define an angle which is less than or equal to 30° with the radial direction and/or an axis which is perpendicular with the rotation axis. Accordingly, the teeth may be steeper than in the previous embodiments in order to reliably open the connection between the contact features 1830 and 1840. The point of contact between the switching feature 1810 when the first member and the second member are rotationally locked to one another, such as during dose setting, and the respective ratchet tooth 1805 may be between the inclined side surfaces of the respective tooth. The point of contact may be in a flat region of the respective tooth. If the switching feature engages the free end of a tooth after the dose delivery operation has been completed, a force which is required to reengage a clutch after dose delivery need not account for a force required to slightly displace the switching feature, e.g. radially. Such a slight displacement might be necessary when the re-engagement of the clutch requires a small rotational movement of the ratchet with the switching feature being arranged between two adjacent teeth after the dose delivery movement of the piston rod has been completed.

It should be noted that this concept, of course, can also be applied for an axially oriented switching feature 1810. In this case, the switching feature may be axially biased into engagement with the ratchet.

Figure 25A:
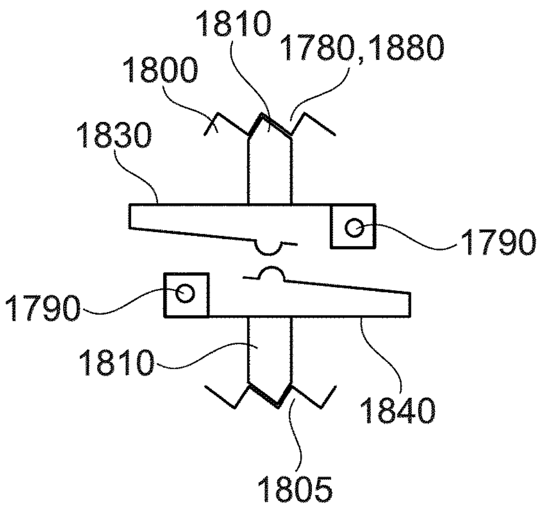
FIGS. 25A and 25B illustrate another embodiment of an electronic system and particularly its use detection unit to generate the use signal.
Figure 25B:
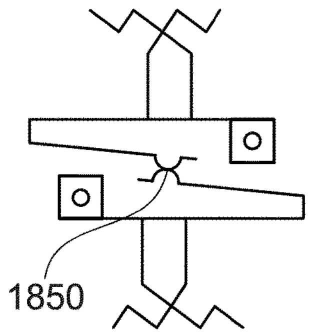

FIGS. 25A and 25B illustrate schematically another embodiment of an electronic system. The representation in the figures is very schematical and the principal set up should be understood as in the embodiments previously described with respect to the first member 1780 and the second member 1790. As the principal functionality is very similar to the one of the previously disclosed embodiments, the following description focuses on the differences but is not restricted thereto. The first and second contact features 1830 and 1840 are connected to the second member 1790 and/or are configured such that they can be moved into mechanical contact with one another. The contact features, preferably, are resiliently deflectable. A protrusion 1850, e.g. a bulge, is provided on the respective contact feature, where the protrusions 1850 of the contact features 1830 and 1840 face one another such that they may be brought into mechanical and electrical conductive contact with one another. The protrusions may facilitate definition of distinct mechanical contact points between the contact features but could also be dispensed with. The contact features may be of metal e.g. a strip bent to the desired shape. When the contact features are conductively connected, the use signal may be generated. The contact features may be electrically conductively connected to the power supply 1500 discussed previously.

In the depicted embodiment, a plurality of switching features 1810 is provided. One of the switching features is associated with the first contact feature 1830 and the other switching feature 1810 is associated with the second contact feature 1840. Both switching features do cooperate with the ratchet which comprises ratchet teeth 1805 and ratchet pockets 1800. Of course, as in the previously discussed embodiments, the ratchet extends circumferentially where only the portions thereof which are engaged by the switching features 1810 are shown in the drawings. The switching features, with respect to the ratchet, are "in phase". That is to say, both switching features either engage ratchet pockets or cooperate with ratchet teeth.

From the arrangement depicted in FIG. 25A, when the first member 1780 commences rotation relative to the second member 1790, such as during dose delivery, the first member rotates relative to the switching features and the switching features are radially, particularly inwardly, displaced, on account of their cooperation with the teeth. This displaces the contact features relative to one another such that they may be brought into mechanical cooperation with each other to generate the use signal. The situation when the use signal is generated and the contact features, e.g. their protrusions 1850, contact each other is depicted in FIG. 25B. As both features are displaced such that the contact features move towards each other, the absolute displacement of the respective contact feature relative to the ratchet may be less than the distance between the first contact feature 1830 and the second contact feature 1840 which has to be covered in order to establish mechanical contact between these features. This is because two switching features are provided which cooperate with the ratchet and both being displaced relative to the ratchet in phase with one another, e.g. both inwardly or both outwardly. The displacement may be converted into movement of the contact features towards each other. The two switching features 1810 may also be moved towards one another when cooperating with the ratchet teeth. The switching features 1810 may be aligned, e.g. radially. The switching features may be oriented along a common axis, e.g. such that the axis is radially offset from the rotation axis of the first member 1780 or intersects with the rotation axis. The respective switching feature 1810 is preferably linearly guided. This is not explicitly shown in the drawings. The respective switching feature is radially outwardly biased when cooperating with the associated ratchet tooth such that it is driven by the biasing force to reengage a ratchet pocket when rotation of the first member 1780 continues. Expediently, the bias is provided by the displaced contact feature(s).

The protrusion 1850 or contact area with the other contact feature may be disposed close to a free end of the respective contact feature.

Beginning from a mounting portion where the respective contact feature is connected to the second member 1790, the respective contact feature may have the following portions:

- a first contact feature portion extending away from the mounting portion towards a free end of the respective contact feature;
- a second contact feature portion which extends along the first contact feature portion, e.g. towards the mounting portion
- a bent or curved portion connecting the first and second contact feature portions.

The free end may be the end of the second contact feature portion. The protrusion 1850 may be disposed in the second contact feature portion.

Figure 26A:
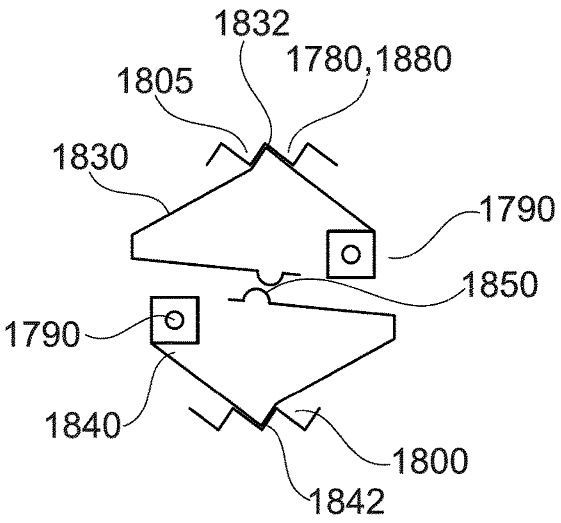
FIGS. 26A and 26B illustrate another embodiment of the electronic system and particularly its use detection unit to generate the use signal.
Figure 26B:
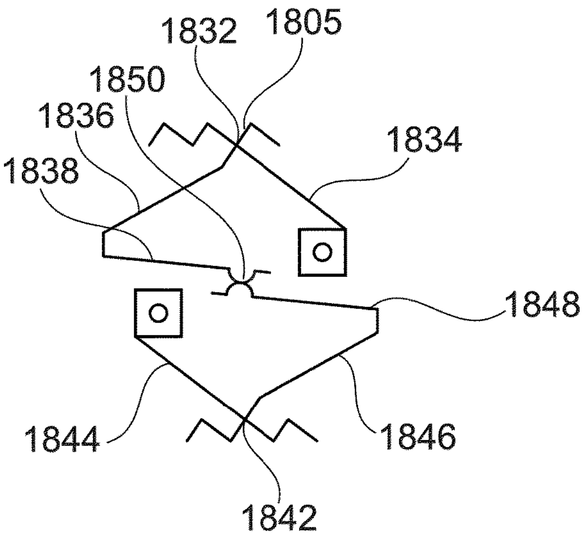

FIGS. 26A and 26B illustrate another embodiment of the electronic system. This embodiment largely corresponds to the one which was discussed in conjunction with FIGS. 25A and 25B. Therefore, the following description focuses on the differences. The most prominent difference is that this embodiment does not use separate switching features 1810 to displace the contact features 1830, 1840. Rather, the respective contact feature 1830, 1840 comprises a ratchet interaction portion 1832, 1842. The interaction portion directly engages the ratchet teeth and/or pockets.

From a mounting portion, where the respective contact feature 1830, 1840, is connected with the second member 1790, the respective contact feature may have the following portions:

- a first contact feature portion (1844, 1834) extending away from the mounting portion, preferably towards the ratchet and/or outwardly;
- the interaction portion (1842, 1832) to interact with the ratchet; in the interaction portion, the contact feature may be bent or kinked so as to enhance engagement with and/or to mimic the shape of a ratchet pocket;
- a second contact feature portion (1846, 1836) extending away from the ratchet, e.g. inwardly.
- a third contact feature portion (1848, 1838), which follows the second contact feature portion and/or which extends up to the free end of the contact feature; the third contact feature portion may extend along the first contact feature portion, along the interaction portion and/or the second contact feature portion. The third contact feature portion may comprise the free end and or a contact area designed to be contacted by the other contact feature.

Every one of these portions may be, preferably resiliently, deflectable relative to the mounting portion and/or relative to other portions. The third contact feature portions of the contact features 1840 and 1830 may face one another, especially in the region which is designed to make mechanical contact, e.g. the region with the protrusions 1850.

When the first member rotates relative to the second member, the contact features are deflected such that they are brought into contact with each other. For example, the contact areas in the third region may contact one another, e.g. the protrusions 1850. This situation is depicted in FIG. 26B. As rotation continues, the arrangement in FIG. 26A is resumed, e.g. on account of the resiliency of the contact features.

The embodiments depicted in FIGS. 25A to 26B use different engagements with the ratchet in order to effect a displacement in a synchronous manner that is to say if one switching feature or contact feature is displaced towards the other one so is the other contact feature or the associated switching feature. This implies that the depth of the ratchet pockets may be reduced as two different ratchet pockets or ratchet teeth contribute to the relative movement. Within the constraints of a consistent outer diameter of the use signal generation interface member, a reduced depth of the ratchet pockets may allow for a smaller ramp angle of the ramp surface of the teeth, especially at the surface delimiting the teeth in that direction in which the first member should rotate. This may be advantageous to further reduce the dispense force or torque required to exerted by the user. Also, if two engagements with the ratchets are employed and a relative movement of the switching features or contact features towards either other is used to generate the use signal, tolerance requirements may be lower and/or the entire stability and integrity of the system may be improved.

Moreover, having two distinct locations of engagement with the ratchet may also improve the resistance which the ratchet provides against rotation in a direction opposite to the one during dose delivery. This may improve the safety of the device. As far as a clicker functionality of the ratchet with the element engaging the ratchet such as the contact feature or the switching feature is concerned, having two engagements potentially increases the risk that, if the re-engagement with the ratchet pockets is not happening exactly at the same time, separate clicking noises or tactile feedbacks are generated although only one feedback should be noticeable. This risk could be reduced if one of the switching features or contact features is designed to generate a smaller or less noticeable feedback, e.g. by rounding the edges of that portion which engages the ratchet pocket. The feedback would then be dominated by the re-engagement of the other switching feature with the ratchet pocket. In summary, the feedbacks generated at the two locations may be designed to be different, e.g. one is more noticeable than the other one, which preferably is almost not noticeable or not noticeable.

Figure 27:
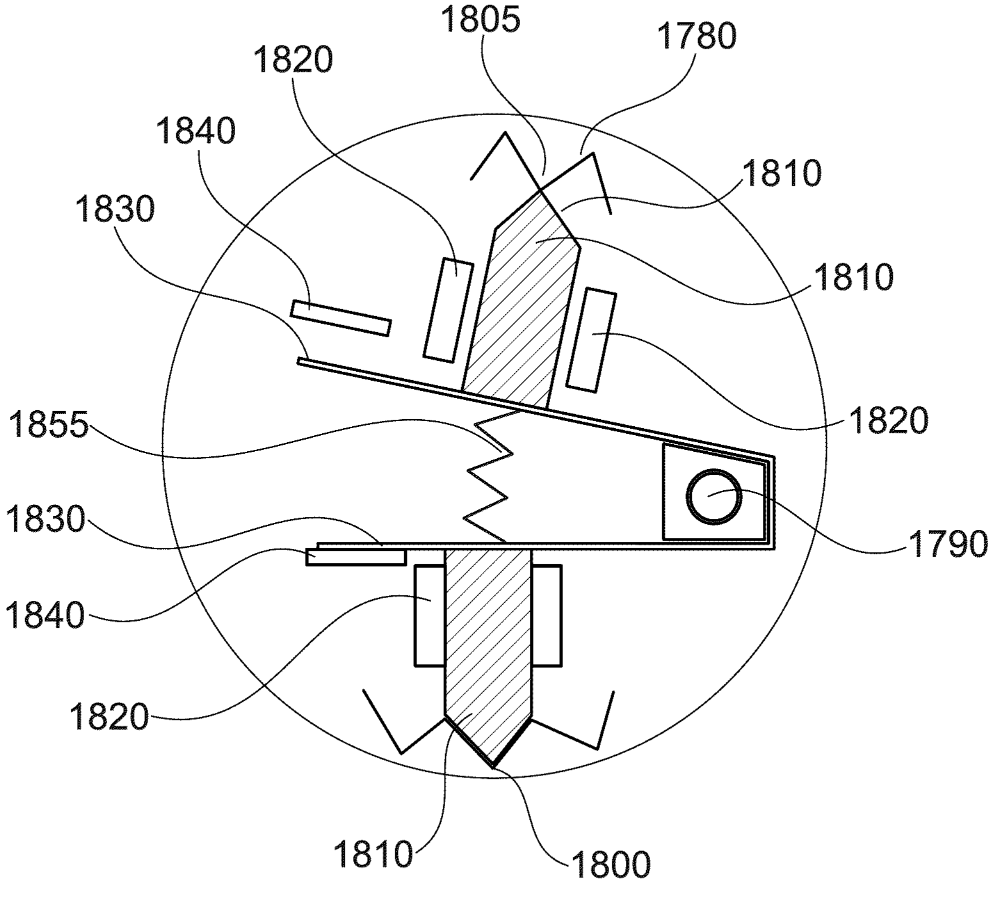
FIG. 27 illustrates another embodiment of the electronic system and particularly its use detection unit to generate the use signal.

FIG. 27 illustrates another embodiment of the electronic system. Again, the essential functionality corresponds to the embodiments which have been discussed previously where the following description focuses on the differences. In general, this embodiment is very similar to the one depicted in FIGS. 25A and 25B. However, in this embodiment, the two contact locations between the ratchet and the switching features 1810 are out of phase. That is to say one of the switching features 1810 interacts with a ratchet tooth in the position before relative movement between the first member 1780 and the second member 1790 is commenced, where the other one of the switching features 1810 interacts with a ratchet pocket or is arranged in the pocket in that position. Of course, if the contact features on their own engage the ratchet as in FIGS. 26A and 26B, the switching features 1810 could also be dispensed with in this arrangement.

Each of the switching features 1810 is associated with one contact feature 1830, respectively. Accordingly, if the switching feature 1810 is displaced, the contact feature may follow this displacement in one direction, e.g. radially and/or inward, and/or may bias the switching feature 1810 resiliently in the other direction, e.g. radially, such as radially outward, and/or due to its intrinsic resiliency or due to a biasing member such as a spring transferring a biasing force to the switching feature 1810 via the contact feature 1830. In the situation depicted in FIG. 27, the upper switching feature 1810 which is in cooperation with a ratchet tooth 1805 may be biased towards the ratchet tooth, e.g. by the contact feature 1830 or the biasing member, e.g. a spring.

Aside from the contact features 1830 which are displaced relative to the second member 1790 while the first member 1780 rotates relative to the second member, in this embodiment, at least one further contact feature 1840 is provided. The further contact feature 1840 may be static or immovable, particularly relative to the second member 1790. In the depicted embodiment, two further contact features 1840 are provided. Depending on the state of the switching feature 1810 or the state engagement of the ratchet, one of the contact features 1830, preferably only one of these contact features, mechanically contacts a further contact feature 1840. Preferably, one further contact 1840 feature is associated with each contact feature 1830. In the depicted situation, the lower contact feature 1830 mechanically contacts the associated lower further contact feature 1840.

In the depicted embodiment, the contact features 1830 associated with the switching features 1810 and/or the switching features are mechanically coupled with each other via a coupling member 1855. The coupling member 1855 may be arranged between the contact features 1830. In this way, movement of and/or force acting on one of the contact features 1830 or switching feature 1810 may be transferred to the other contact feature 1830 or switching feature 1810. The coupling feature 1855 may be rigid or a resilient member such as the biasing member mentioned above. The resilient member may be a spring such as a compression spring and/or a micro spring. The coupling member 1855 may be configured to exert a transversely or radially directed biasing force relative to the rotation axis, which in this embodiment as in the previous embodiment is directed perpendicular to the plane of the shown representation. The system may be designed such that in each stable relative rotational position between the first member and the second member, one contact feature 1830, preferably just one, is conductively connected to the associated further contact feature 1840. The pair of contact features 1830 may shuttle between two different further contact features 1840 as depicted. The respective switching feature 1810 is preferably guided, e.g. linearly guided, such as by a corresponding guide slot 1820, where the respective guide slot may be rotationally and/or axially locked to the second member 1790.

When, from the situation depicted in FIG. 27, the first member 1780 rotates, e.g. in the anti-clockwise direction, the lower switching feature 1810 is displaced radially, particularly inwardly. This disengages the lower contact feature 1830 from the associated further contact feature 1840 and transfers load towards the upper contact feature 1830 via the coupling member 1855, expediently after biasing this coupling member. As the upper switching feature 1810 may then engage the subsequent ratchet pocket 1800 which adjoins the ratchet tooth 1805 counter to the rotation direction, the upper contact feature 1830 may be moved into contact with the associated further contact feature 1840, e.g. via the relaxing coupling member 1855.

In the depicted embodiment, in each stable rotational position there is a closed contact connection between a pair of one contact feature 1830 and one further contact feature 1840. Expediently, the electronic system is configured such that the use signal is generated when the contact feature 1830 and further contact feature 1840 make mechanical contact with each other. Afterwards, the electrical connection between the power supply and this pair may be interrupted in order to avoid excessive power drain. The power supply may be conductively connected to that pair of contact feature 1830 and further contact feature 1840 which are currently not electrical conductively connected. This may be achieved by appropriate switching circuitry in the electronic control unit, for example.

This embodiment can be designed such that each of the ends of the shuttle which is formed by the switching features and the contact features 1830 together with the coupling member 1855 changes the position relative to the ratchet, i.e. the teeth and/or the pocket, only after a rotation by an angle corresponding to plurality of unit setting increments, e.g. two unit increments. However one of the two ends changes position relative to the ratchet every one unit setting increment such that the two ends may be moved in an alternating fashion increment-wise. In this case, a resilient coupling member 1855 is preferred as then the entire length variation in the shuttle is greater than when both ends of the shuttle change position relative to the ratchet, e.g. from engaging a tooth to engaging a pocket or vice versa during each unit setting increment or even in a finer pitch than the unit increments.

Figure 28:
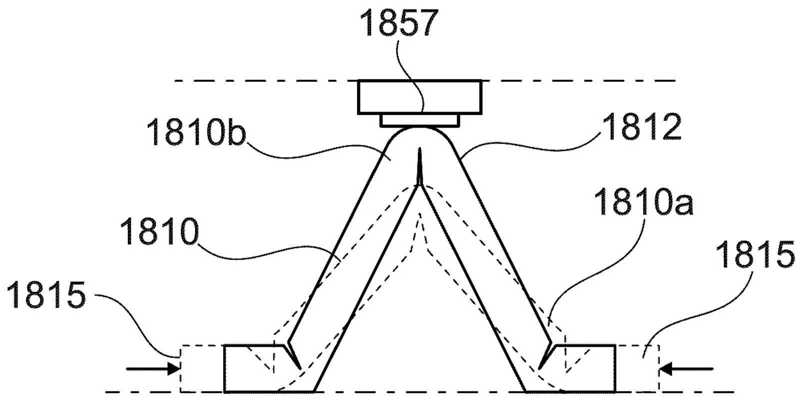
FIG. 28 illustrates another embodiment of the electronic system and particularly its use detection unit to generate the use signal.

FIG. 28 illustrates another embodiment of the electronic system. This embodiment is very schematically represented by its key component which is a switching feature 1810 which at its both ends 1815 interacts with a ratchet (not explicitly illustrated). The switching feature 1810 is, expediently, elastically deformable such that rotation of the first member 1780 relative to the second member 1790 is converted into axial movement of a portion 1812 of the switching feature, e.g. a central portion. The portion 1812 of the switching feature which is axially displaced may be axially guided, e.g. in a guide slot (not explicitly shown). The switching feature 1810 converts rotational movement into axial deformation of the switching feature is sometimes also designated as a wishbone or toggle mechanism component. Rotational movement of the first member 1780 (not explicitly shown) moves the ends 1815 from a position where they each engage a ratchet pocket closer to each other (along the respective ratchet tooth). This results in an axial displacement of the portion 1812 of the switching feature 1810.

This axial displacement may be used to trigger the use signal. FIG. 28 shows two configurations of the switching feature 1810. One configuration, labeled as 1810*a*, which the switching feature has before rotation of the first member is commenced and the second configuration 1810*b* where the portion 1812 has been axially displaced relative to the ratchet and/or the ends 1815. In the configuration 1810*b* the portion 1812 may contact a switch 1857, such as a microswitch, which, when triggered, may cause generation of the use signal with an according wake-up process for the motion sensing unit or the electronic system. The switch 1857 may be mounted on a conductor carrier, e.g. a circuit board, which may be provided within the user interface member, e.g. the injection or dose knob, which may be rigidly connected to or integrally formed with the second member 1790.

Figure 29:
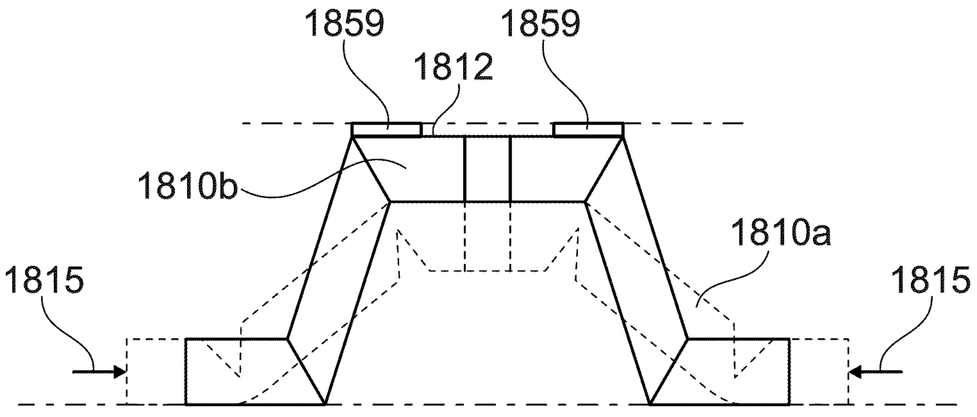
FIG. 29 illustrates another embodiment of the electronic system and particularly its use detection unit to generate the use signal.

FIG. 29 illustrates schematically another embodiment of the electronic system. Essentially, the electronic system corresponds to the one described in conjunction with the previous embodiment shown in FIG. 28. However, as opposed to having a switch 1857 which is contacted or triggered by portion 1812, here portion 1812 bridges the region between two electrically separated contacts, e.g. contact pads. The portion 1812 on its side facing the contacts 1859 is expediently conductive such that, by way of the portion 1812, which is axially displaceable relative to the ratchet teeth (not explicitly shown) an electrically conductive connection can be established between contacts 1859. This electrically conductive connection may trigger generation of the use signal, e.g. via current flowing from one contact to the other contact through electrically conductive portion 1812 or an electrically conductive layer provided on portion 1812 which, then, may be electrically insulating. As opposed to using the switch 1857, this embodiment may facilitate meeting tighter tolerances.

Figure 30:
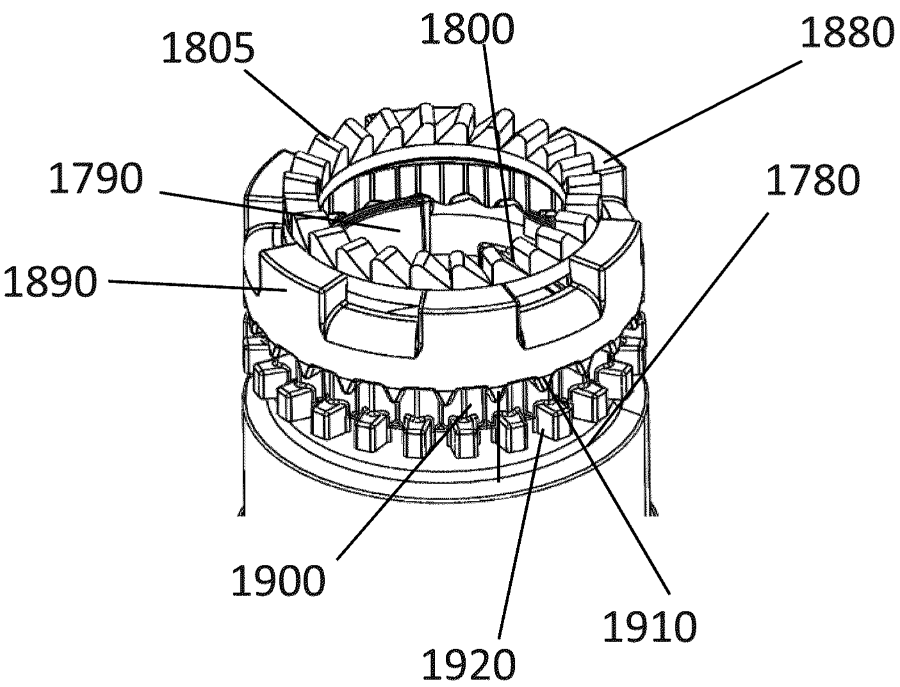
FIG. 30 illustrates another embodiment of the electronic system and particularly its use detection unit to generate the use signal.

FIG. 30 illustrates another embodiment of the electronic system. As in the previously described embodiments, a use signal generation interface member 1880 is provided. This member 1880 comprises ratchet pockets 1800 and the ratchet teeth 1805 which define the incremented interface which generates use signals in cooperation with the switching feature 1810 as discussed previously already. Adjacent teeth may be separated by an angle corresponding to one unit setting increment. Thus, the unit setting increment may be equal to the use signal generation increment as has been discussed further above. Therefore, the unit setting increment is used as reference below for some angles. However, it should be noted that the use signal generation increment could be used as well, in case it is different from the unit setting increment.

The use signal generation interface member 1880 is expediently rotationally secured to the first member 1780 and axially secured relative to the second member 1790 as has been discussed already further above. The interface which rotationally secures the member 1880 to the first member 1780 is realized by spline features 1900, e.g. axially oriented ribs. The spline features 1900 may be provided on the first member 1780. Corresponding features on the use signal generation interface member 1880 may be arranged to engage the spline features 1900. Of course, the position of the spline features and the corresponding features which engage the spline features could also be reversed such that the spline features are provided on member 1880 and the corresponding features provided on the first member 1780. The use signal generation interface member may engage the first member 1780 in a proximal end region thereof. The proximal end region of the first member 1780 may be received within the use signal generation interface member 1880.

The use signal generation interface member 1880 is axially movable relative to the first member 1780 between a first position and a second position, where the first position is shown in FIG. 30. The member 1880 may be rotationally locked relative to the first member 1780 in both positions or in just one of these positions. The second position may be distally offset relative to the first position, where the distal direction, in FIG. 30 is the downward direction. In the second position, axially oriented engagement features 1910 of the use signal generation interface member may engage corresponding features 1920, e.g. slots, in the first member 1780. The engagement may either establish the rotational lock between the first member and the use signal generation interface member or may stabilize the relative angular position between the first member 1780 and the use signal generation interface member 1880. This may increase the accuracy of the motion sensing and/or the determination of the delivered dose as the rotational orientation between the first member, which rotates in the dose delivery operation and of which rotation should be monitored or measured via the motion sensing unit, and the use signal generation interface member 1880, which may carry the detection regions 1890, which are used to monitor the rotational or angular position of the first member in the dose delivery operation, is stabilized. The interface formed during the movement of the use signal generation interface member 1880 from the first position into the second position may be self-centering, which may be achieved by slanted surfaces of one of the engagement features 1910 and 1920. In the depicted embodiment, the features 1910, which may be pointed teeth, have slanted surfaces.

The angular distribution of the engagement features 1910 and/or 1920 may have a pitch which is determined by the angle corresponding to one use signal generation increment and/or one unit setting increment, where, as already discussed, the angles corresponding to one use signal generation increment and one unit setting increment may be identical. The distance by which the use signal generation interface member is moved axially relative to the first member 1780 may be determined by the clutch release distance, e.g. $d_c$, which has been discussed further above already.

In the depicted embodiment the use signal generation interface member 1880 provides the use signal generation interface by ratchet teeth and ratchet pockets and also the detection regions 1890 for determining the amount of relative rotation during dose delivery. This is advantageous from a manufacturing perspective as a structure for generating the use signal as well as a structure for monitoring movement can be integrated into one component, which can be integrated into a device more easily than separate components. The detection regions 1890 may be provided on an outer surface and the use signal generation interface may be provided on the inner surface of the member 1880.

Of course, this embodiment could be combined with any one of the remaining embodiments set forth in this disclosure.

FIGS. 31A through 31E illustrate another embodiment of the electronic system. Both figures show a schematic sectional view during different stages of operation of the electronic system. This embodiment is similar to the ones which are previously described, which is why this description focuses on the differences. Also, features which are disclosed herein may be applied for the other embodiments.

Figure 31A:
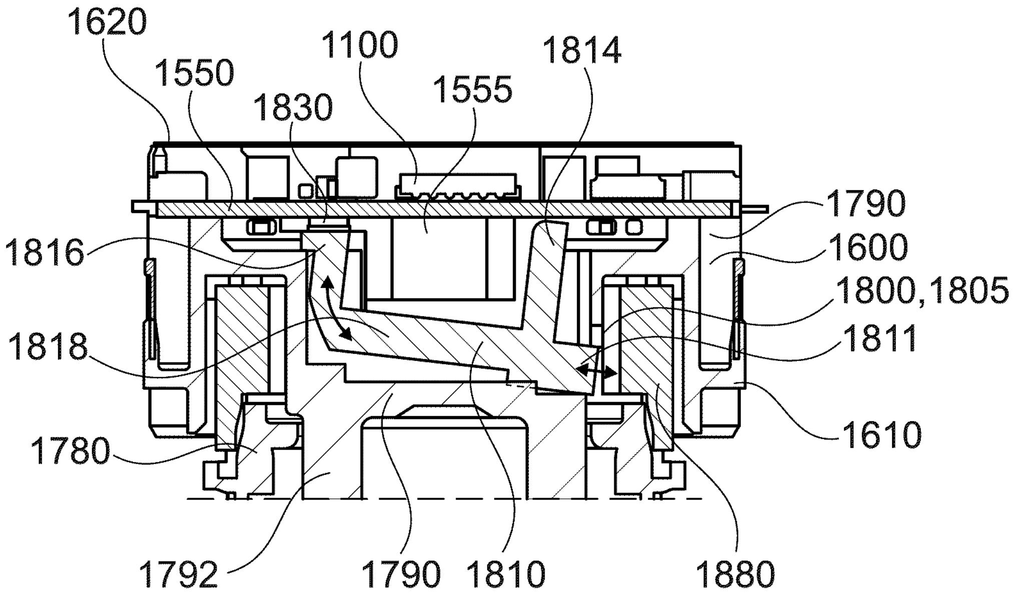
FIGS. 31A to 31E illustrate embodiments of the electronic system and particularly its use detection unit to generate the use signal.

FIG. 31A shows the first member 1780 and the second member 1790. As in the previous embodiment, the first member is rotatable relative to the second member during dose delivery. Both members co-rotate for the dose setting operation. The second member may be rotationally locked relative to the housing during the dose delivery operation. As opposed to the embodiments which have been described previously, the second member 1790 is shown in more detail in these figures. The second member 1790 and a user interface member 1600, e.g. a dose or injection knob, may be integrated into a common component or rigidly secured to one another. However, the second member and the user interface member 1600 may also be separate components, which may be movably or immovably connected to each other. Again, the user interface member for interacting with the user for dose setting may be different from the one during dose delivery. In the present embodiment, the user interface member 1600 provides a surface which is contacted by the user for the dose setting operation, i.e. a setting surface 1610. The setting surface may be a side surface of the user interface member 1600 and/or face in the radial direction. Alternatively or additionally, the user interface member provides a delivery surface 1620. The delivery surface may be a surface facing in the axial direction, e.g. proximally. The delivery surface 1620 may be contacted by the user for initiating the dose delivery operation, after the dose has been set. The second member 1790 may have an interaction portion 1792, e.g. a hollow or sleeve like portion, which is provided to receive and/or interact with, e.g. engage, particularly threadedly engage, a piston rod which is arranged to be driven by the second member during the dose delivery operation. The setting surface 1610 may be radially outwardly offset relative to the interaction portion 1792.

The use signal generation interface member 1880 is operatively connected to the first member 1780, e.g. rotationally locked to the first member and may be axially movable or fixed relative to the first member as has been discussed previously, e.g. in connection with FIG. 30. The use signal generation interface member, expediently comprises the ratchet, e.g. ratchet teeth and ratchet pockets 1800, 1805, respectively as has been discussed previously.

The electronic system also comprises a switching feature 1810. The switching feature 1810 has an interaction portion 1811 which engages the ratchet as described previously. As the ratchet is radially oriented, the cooperation with the ratchet results in a radial force transferred to the switching feature 1810 as in the previous embodiments. However, in this embodiment, the switching feature is mounted in the electronic system in a manner such that it is pivotable. Specifically, the switching feature 1810 is mounted to the first member 1790 and/or the user interface member 1600, especially in the interior thereof, with a pivot portion 1814. The pivot portion 1814 is expediently axially, e.g. proximally, offset from the interface between the use signal generation interface member 1880 and the switching feature 1810. In this way, a radial force may be converted into pivoting movement, particularly involving an axial component in the proximal direction, of the switching feature, e.g. when the switching feature 1810 is displaced inwardly relative to the interface member 1880. Accordingly, the switching feature 1810 pivots relative to the first member 1780 and/or the second member 1790 during rotation of the first member 1780 and/or member 1880 relative to the second member 1790 and/or housing 10 (not explicitly shown in this embodiment).

The switching feature 1810 further comprises a use signal trigger portion 1816. The use signal trigger portion 1816 may be radially spaced apart from the pivot portion 1814. The pivot portion 1814 may be connected to the trigger portion 1816 via a connecting portion 1818. The connecting portion may be axially offset from the trigger portion 1816 and the pivot portion, e.g. distally. The pivot portion and the trigger portion may be oriented axially and radially separated. The connecting portion may extend transversely, particularly relative to the rotation axis. The pivot portion 1814, the connecting portion 1818, and the trigger portion 1816 may be part of a portion of the switching feature with a U-like cross-section. The interaction portion 1811 may extend along a main direction defined by the connecting portion 1818. The pivot portion 1814 and the trigger portion 1816 may be separated by a free space. In the depicted embodiment, the trigger portion 1816 is designed to displace a contact feature 1830 in order to trigger or generate the use signal. In the situation in FIG. 31A, the use signal may be triggered, as the contact feature 1830 may contact another contact feature on a conductor carrier 1550, such as a circuit board, e.g. a printed circuit board. Of course, aside from contacting another electrically conductive feature with the mechanical contact establishing the use signal via a conductive connection, a switch may also be provided which may be mechanically contacted by the trigger portion 1816.

The conductor carrier 1550 may be retained in the interior of the user interface member 1600 and may be conductively connected to and/or mechanically support or carry one or more electrical or electronic components of the electronic system, such as the electronic control unit 1100, e.g. a microprocessor or microcontroller, or members of the motion sensing unit. After the use signal has been generated, the switching feature 1810 may be displaced back into its initial position, e.g. on account of the resiliency of the contact feature 1830 as previously discussed already or another resilient feature implemented in the electronic system. This situation is shown in FIG. 31B. The control unit 1100 may be mounted on a side of the conductor carrier remote from the switching feature 1810.

The space defined in by the switching feature between the trigger portion 1816 and the pivot portion 1814 may be designed to receive an electrical component 1555 of the electronic system, such as a capacitor. The electrical component 1555 may be mounted on the conductor carrier 1550 on a side facing away from the electronic control unit 1100. Accordingly, the U-like cross-section of the switching feature 1810 allows for space-saving arrangement within the user interface member. The interior space of the user interface member may have an interior diameter greater than the interior diameter of the first member and/or the second member.

As compared to the switching features which have been described previously, the increase in dispense force may be particularly small for this configuration with the switching feature pivoting in the axial direction.

Figure 31B:
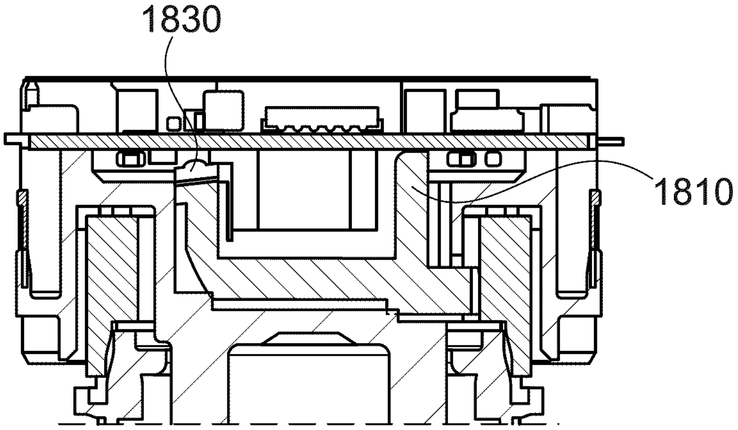
Figure 31D:
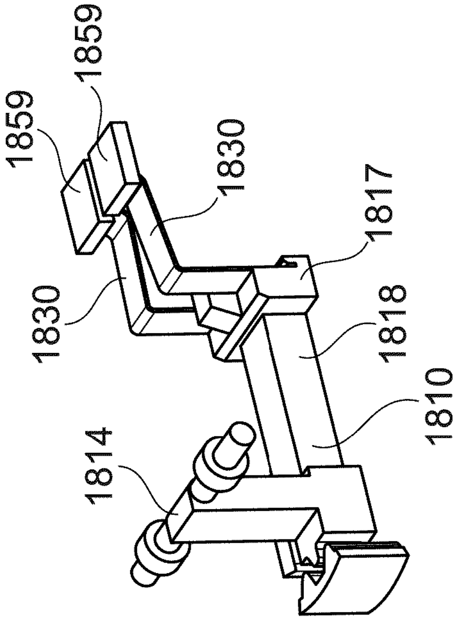
Figure 31E:
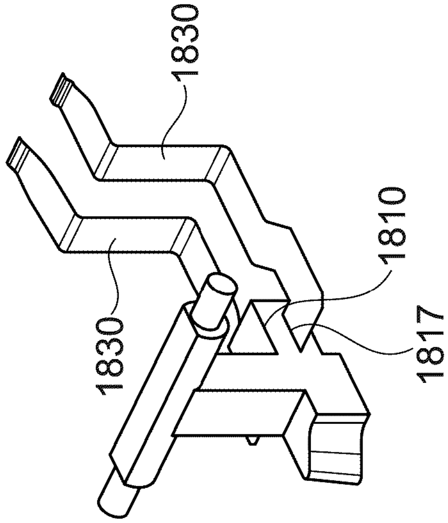
Figure 31C:
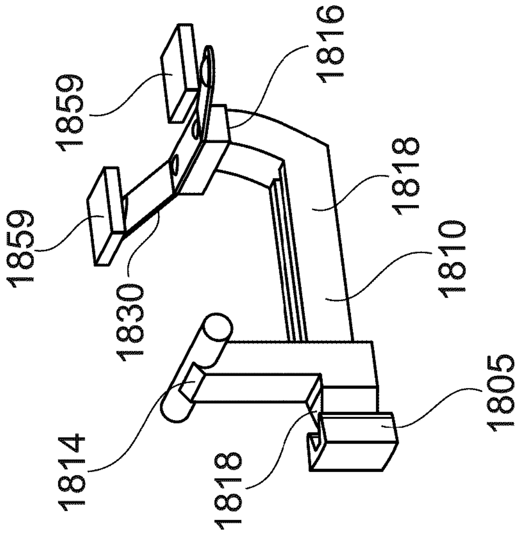

FIGS. 31C to 31E illustrate three embodiments of the switching feature which could be implemented in the embodiment discussed in conjunction with FIGS. 31A and 31B instead of the switching feature 1810 employed therein.

FIG. 31C illustrates a switching feature 1810 with the U-shaped portion provided with an electrical contact feature 1830 which is used to conductively connect two contacts 1859, e.g. on the conductor carrier (not explicitly shown). The situation depicted shows the situation before the use signal is generated. That is to say, one connection, e.g. to the right lower contact 1859, is open, where the other contact 1859 may be conductively connected to the contact feature 1830. The contact feature 1830 may be formed as a leaf-spring and be connected to the trigger portion 1816 of the switching feature 1810. The contract feature 1830 may be resilient, such that, once the conductive connection between the contacts 1859 is established by the contact feature, resiliency removes this conductive connection when the switching feature again engages a ratchet pocket. The contact feature 1830 may protrude radially from the switching feature with respect to the axis defined by the connecting portion 1818. The contact feature may have a U-like cross-section, especially as seen in a plane perpendicular to the axis defined by the connecting portion 1818. The contact feature 1830 may be connected to a tip of the trigger portion 1816.

FIG. 31D shows another embodiment of the switching feature 1810, where the contact feature 1830 is oriented along the axis defined by the connecting portion 1818 and has two different regions, each of which is provided to contact one of the contacts 1859. When both contacts 1859 are conductively connected to the contact feature 1830, the use signal is generated. The contact feature 1830 is connected to a securing portion 1817 which is provided at an end of the connecting portion remote from the pivot portion 1814. For example, the switching feature 1810 may be molded around the contact feature 1830 or the contact feature may be secured in a different manner to the switching feature, e.g. by a snap-fit.

FIG. 31E shows another embodiment of the switching feature 1810. This embodiment very much resembles the one in FIG. 31D. However, the connecting portion 1818 of the switching feature 1810 is dispensed with and replaced by a portion of the contact feature 1830. The general geometry of the structure comprising the switching feature and the associated contact feature, however, is very similar to the one depicted in FIG. 31D.

The terms “drug” or “medicament” are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient (“API”), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or “drug container” adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The scope of protection is not limited to the examples given herein above. Any invention disclosed herein is embodied with novel characteristic and combination of characteristics, including every combination of features stated in the claims, even if this feature or this combination of features is not explicitly stated in the claims or in the examples.

REFERENCE NUMERALS

1 device
2 device
10 housing
12 dosage knob
11 injection button
13 dosage window
14 container or container receptacle
15 needle
16 inner needle cap
17 outer needle cap
18 cap
27 output
28 switch
29 power supply
70 dial sleeve
70*a* segment
70*b* segment
71*a* . . . formation
205 grip
210 injection button
210*a* button part
210*b* button part
215 sensor arrangement
215*a* sensor
215*b* sensor
500 encoder system
700 controller
800 switch
900 encoder system
1000 electronic system
1100 electronic control unit
1200 motion sensing unit
1300 use detection unit
1400 communication unit
1500 power supply
1550 conductor carrier
1555 electrical component
1600 user interface member
1610 setting surface
1620 delivery surface
1780 first member
1790 second member
1792 interaction portion
1800 ratchet pockets
1805 ratchet teeth
1810 switching feature
1810*a* configuration
1810*b* configuration
1811 interaction portion
1812 portion
1814 pivot portion
1815 end
1816 use signal trigger portion
1817 securing portion
1818 connecting portion
1820 guide slot
1830 first contact feature
1832 interaction portion
1834 contact feature portion
1836 contact feature portion
1838 contact feature portion
1840 second contact feature
1842 interaction portion
1844 contact feature portion
1846 contact feature portion
1848 contact feature portion
1850 protrusion
1855 coupling member
1857 switch
1859 contact
1860 surface
1870 ramp
1880 use signal generation interface member
1890 detection region
1900 spline feature
1910 engagement feature
1920 engagement feature
$d_c$ clutch release distance

The invention claimed is:

1. An electronic system for a drug delivery device, the electronic system comprising:

a dose setting and drive mechanism configured to perform a dose setting operation for setting a dose to be delivered by the drug delivery device and a dose delivery operation for delivering the set dose, wherein the dose setting and drive mechanism comprises a first member and a second member, wherein in the dose delivery operation and/or in the dose setting operation, the first member moves relative to the second member;

an electronic control unit configured to control an operation of the electronic system; and an electrical use detection unit operatively connected to the electronic control unit, the electrical use detection unit being configured to generate a use signal in response to a relative movement between the first member and the second member, the use signal indicating that a user has commenced the dose setting operation or the dose delivery operation, wherein the electronic system has a first state and a second state, and is configured to be switched from the first state into the second state by the electronic control unit in response to the use signal, wherein the electronic system consumes more electrical power in the second state as compared to the first state, and wherein the second member is directly engaged with a piston rod to drive the dose delivery operation.

2. The electronic system of claim 1, wherein the electrical use detection unit is configured to generate the use signal in response to a relative rotational movement between the first member and the second member during the dose delivery operation.

3. The electronic system of claim 1, wherein the dose setting and drive mechanism comprises a dose member that is rotatable relative to a housing of the electronic system in the dose setting operation in whole-number multiples of a unit setting increment, wherein at least one of the first member and the second member is different from the dose member.

4. The electronic system of claim 3, further comprising a use signal generation interface configured to generate the use signal during the dose delivery operation, wherein the use signal generation interface is an incremented interface with an increment that is adjusted to the unit setting increment.

5. The electronic system of claim 3, wherein the electronic system is configured such that the use signal is generated after a rotation of the first member has been commenced and before the first member has rotated relative to the second member by more than one unit setting increment.

6. The electronic system of claim 1, wherein the electronic system further comprises a movable switching feature that is operatively coupled to one or both of the first member and the second member such that a rotation of the first member relative to the second member causes a movement of the switching feature relative to the first member and/or relative to the second member, wherein the electronic system is configured such that the movement of the switching feature is used to trigger generation of the use signal.

7. The electronic system of claim 6, wherein the movable switching feature is operatively coupled to the first member and/or to the second member such that the rotation of the first member relative to the second member is converted into the movement of the switching feature to cause generation of the use signal.

8. The electronic system of claim 6, wherein the movable switching feature is resiliently biased into engagement with a block feature before the first member is rotated relative to the second member, and wherein, when the first member is rotated relative to the second member, the block feature is removed from the switching feature such that the biasing force can drive the movement of the switching feature to cause generation of the use signal.

9. The electronic system of claim 6, wherein the switching feature is linearly guided.

10. The electronic system of claim 6, wherein the switching feature is pivotally mounted, and wherein the movement of the switching feature is a pivoting movement.

11. The electronic system of claim 6, wherein one of the first member and the second member is provided with a ratchet with circumferentially disposed ratchet teeth, and wherein the switching feature is arranged to cooperate with the ratchet.

12. The electronic system of claim 11, wherein the electronic system comprises a first switching feature and a second switching feature, wherein the first switching feature and the second switching feature are arranged to cooperate with the ratchet.

13. The electronic system of claim 12, wherein at least one of the first switching feature or the second switching feature is a deformable switching feature and is engaged with the ratchet at different locations where a rotation of the first member relative to the second member causes a portion of the deformable switching feature to be axially displaced.

14. The electronic system of claim 1, further comprising a motion sensing unit that is operational in the second state of the electronic system, and is non-operational in the first state of the electronic system, wherein the electronic control unit is configured to issue a command to render the motion sensing unit operational in response to the use signal.

15. The electronic system of claim 1, wherein the first member and the second member are configured to move during the dose setting operation and/or during the dose delivery operation relative to a housing of the electronic system or the drug delivery device.

16. A drug delivery device comprising:

a reservoir retainer for retaining a reservoir with a drug in the drug delivery device; and an electronic system comprising:

a dose setting and drive mechanism configured to perform a dose setting operation for setting a dose to be delivered by the drug delivery device and a dose delivery operation for delivering the set dose, wherein the dose setting and drive mechanism comprises a first member and a second member, wherein in the dose delivery operation and/or in the dose setting operation, the first member moves relative to the second member;

an electronic control unit configured to control an operation of the electronic system; and an electrical use detection unit operatively connected to the electronic control unit, the electrical use detection unit being configured to generate a use signal in response to a relative movement between the first member and the second member, the use signal indicating that a user has commenced the dose setting operation or the dose delivery operation, wherein the electronic system has a first state and a second state, and is configured to be switched from the first state into the second state by the electronic control unit in response to the use signal, wherein the electronic system consumes more electrical power in the second state as compared to the first state, and wherein the second member is directly engaged with a piston rod to drive the dose delivery operation.

17. The drug delivery device of claim 16, further comprising the reservoir containing the drug.

18. The drug delivery device of claim 16, wherein the first member and the second member are configured to move during the dose setting operation and/or during the dose delivery operation relative to a housing of the electronic system or the drug delivery device.

19. An electronic system for a drug delivery device, the electronic system comprising:

a dose setting and drive mechanism configured to perform a dose setting operation for setting a dose to be delivered by the drug delivery device and a dose delivery operation for delivering the set dose, wherein the dose setting and drive mechanism comprises a first member and a second member, wherein in the dose delivery operation and/or in the dose setting operation, the first member rotates relative to the second member;

an electronic control unit configured to control an operation of the electronic system; and an electrical use detection unit operatively connected to the electronic control unit, the electrical use detection unit being configured to generate a use signal in response to a relative movement between the first member and the second member, the use signal indicating that a user has commenced the dose delivery operation, wherein the electronic system has a first state and a second state, and is configured to be switched from the first state into the second state by the electronic control unit in response to the use signal, and wherein the second member is directly engaged with a piston rod to drive the dose delivery operation.

20. The electronic system of claim 19, wherein the first member and the second member are configured to move during the dose setting operation and during the dose delivery operation relative to a housing of the electronic system or the drug delivery device.

* * * * *